United States Patent
Dayan et al.

(10) Patent No.: US 10,271,907 B2
(45) Date of Patent: Apr. 30, 2019

(54) IMPLANT AND DELIVERY SYSTEM FOR NEURAL STIMULATOR

(71) Applicant: BRAINSGATE LTD., Caesarea (IL)

(72) Inventors: Avinoam Dayan, Zichron Yaakov (IL); Israel Dvorsky, Tel Aviv (IL); Malka Hugeri, Natanya (IL)

(73) Assignee: BRAINSGATE LTD., Caesarea (IL)

( * ) Notice: Subject to any disclaimer, the term of this patent is extended or adjusted under 35 U.S.C. 154(b) by 151 days.

(21) Appl. No.: 15/153,878

(22) Filed: May 13, 2016

(65) Prior Publication Data

US 2016/0331472 A1 Nov. 17, 2016

Related U.S. Application Data

(60) Provisional application No. 62/160,708, filed on May 13, 2015.

(51) Int. Cl.
*A61B 34/20* (2016.01)
*A61N 1/05* (2006.01)
(Continued)

(52) U.S. Cl.
CPC .......... *A61B 34/20* (2016.02); *A61B 17/3468* (2013.01); *A61N 1/0548* (2013.01);
(Continued)

(58) Field of Classification Search
CPC ..... A61B 34/20; A61B 17/3468; A61B 17/34; A61B 17/56; A61B 19/00; A61B 19/201;
(Continued)

(56) References Cited

U.S. PATENT DOCUMENTS

| 4,350,169 A | 9/1982 | Dutcher et al. |
| 4,666,829 A | 5/1987 | Glenner et al. |

(Continued)

FOREIGN PATENT DOCUMENTS

| CA | 2408097 | 11/2001 |
| CA | 2401098 | 1/2002 |

(Continued)

OTHER PUBLICATIONS

Delepine L, Aubineau P, "Plasma protein extravasation induced in the rat dura mater by stimulation of the parasympathetic sphenopalatine ganglion," Experimental Neurology, 147, 389-400 (1997).

(Continued)

*Primary Examiner* — Vi X Nguyen
(74) *Attorney, Agent, or Firm* — RatnerPrestia

(57) ABSTRACT

Apparatus is provided for use with an optical fiber shape-sensing system. The apparatus includes an optical fiber, optically couplable to the optical fiber shape-sensing system, and configured to change shape during advancement through a greater palatine canal of a subject. The apparatus additionally includes a delivery tool configured to be removably coupled to the optical fiber and to distally advance the optical fiber through the greater palatine canal. The apparatus further includes a neural stimulator implant, configured to apply electrical stimulation to a sphenopalatine ganglion (SPG) of the subject. The neural stimulator implant is not in contact with the optical fiber, and is shaped and sized to be delivered to the sphenopalatine ganglion (SPG) by the delivery tool. Other applications are also described.

20 Claims, 26 Drawing Sheets

(51) Int. Cl.
*A61N 1/36* (2006.01)
*A61N 1/372* (2006.01)
*A61B 17/34* (2006.01)

(52) U.S. Cl.
CPC ..... *A61N 1/36103* (2013.01); *A61N 1/37205* (2013.01); *A61B 2017/3407* (2013.01); *A61B 2034/2061* (2016.02)

(58) Field of Classification Search
CPC .......... A61N 1/04; A61N 1/05; A61N 1/0548; A61N 1/36103
See application file for complete search history.

(56) References Cited

U.S. PATENT DOCUMENTS

| | | |
|---|---|---|
| 4,708,139 A | 11/1987 | Dunbar |
| 4,866,042 A | 9/1989 | Neuwelt |
| 4,867,164 A | 9/1989 | Zabara |
| 4,874,694 A | 10/1989 | Gandy et al. |
| 4,907,602 A | 3/1990 | Sanders |
| 4,979,511 A | 12/1990 | Terry et al. |
| 5,011,472 A | 4/1991 | Aebischer et al. |
| 5,025,807 A | 6/1991 | Zabara |
| 5,031,618 A | 7/1991 | Mullett |
| 5,059,415 A | 10/1991 | Neuwelt |
| 5,154,172 A | 10/1992 | Terry et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry et al. |
| 5,215,089 A | 6/1993 | Baker, Jr. |
| 5,222,494 A | 6/1993 | Baker, Jr. |
| 5,223,254 A | 6/1993 | Paradiso et al. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,268,164 A | 12/1993 | Kozarich et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,304,632 A | 4/1994 | Vaudry et al. |
| 5,314,495 A | 5/1994 | Kovacs |
| 5,330,515 A | 7/1994 | Rutecki et al. |
| 5,335,657 A | 8/1994 | Terry, Jr. et al. |
| 5,351,394 A | 10/1994 | Weinberg |
| 5,409,462 A | 4/1995 | Ross |
| 5,453,575 A | 9/1995 | O'Donnell et al. |
| 5,514,131 A | 5/1996 | Edwards et al. |
| 5,531,778 A | 7/1996 | Maschino et al. |
| 5,540,730 A | 7/1996 | Terry, Jr. et al. |
| 5,571,150 A | 11/1996 | Wernicke et al. |
| 5,639,853 A | 6/1997 | Paradiso et al. |
| 5,697,377 A | 12/1997 | Wittkampf |
| 5,707,400 A | 1/1998 | Terry, Jr. et al. |
| 5,716,377 A | 2/1998 | Rise et al. |
| 5,725,471 A | 3/1998 | Davey et al. |
| 5,752,515 A | 5/1998 | Jolesz et al. |
| 5,756,071 A | 5/1998 | Mattern et al. |
| 5,766,605 A | 6/1998 | Sanders et al. |
| 5,792,067 A | 8/1998 | Karell |
| 5,792,100 A | 8/1998 | Shantha |
| 5,830,670 A | 11/1998 | de la Monte et al. |
| 5,833,988 A | 11/1998 | Friden |
| 5,849,600 A | 12/1998 | Nixon et al. |
| 5,928,272 A | 7/1999 | Adkins et al. |
| 5,938,689 A | 8/1999 | Fischell et al. |
| 5,938,690 A | 8/1999 | Law et al. |
| 5,978,702 A | 11/1999 | Ward et al. |
| 5,981,194 A | 11/1999 | Jefferies et al. |
| 5,985,581 A | 11/1999 | Nixon et al. |
| 6,001,331 A | 12/1999 | Caprathe et al. |
| 6,005,004 A | 12/1999 | Katz et al. |
| 6,006,124 A | 12/1999 | Fischell et al. |
| 6,016,449 A | 1/2000 | Fischell et al. |
| 6,033,411 A | 3/2000 | Preissman |
| 6,039,742 A | 3/2000 | Krettek et al. |
| 6,061,593 A | 5/2000 | Fischell et al. |
| 6,066,163 A | 5/2000 | John |
| 6,071,705 A | 6/2000 | Wands et al. |
| 6,086,525 A | 7/2000 | Davey et al. |
| 6,087,118 A | 7/2000 | Aronson et al. |
| 6,114,175 A | 9/2000 | Klunk et al. |
| 6,117,454 A | 9/2000 | Kreuter et al. |
| 6,128,538 A | 10/2000 | Fischell et al. |
| 6,130,048 A | 10/2000 | Nixon |
| 6,132,977 A | 10/2000 | Thompson et al. |
| 6,134,474 A | 10/2000 | Fischell et al. |
| 6,161,045 A | 12/2000 | Fischell et al. |
| 6,200,768 B1 | 3/2001 | Mandelkoe et al. |
| 6,205,359 B1 | 3/2001 | Boveja |
| 6,210,895 B1 | 4/2001 | Schipper et al. |
| 6,211,235 B1 | 4/2001 | Wu et al. |
| 6,230,049 B1 | 5/2001 | Fischell et al. |
| 6,232,326 B1 | 5/2001 | Nelson |
| 6,238,892 B1 | 5/2001 | Mercken et al. |
| 6,277,841 B1 | 8/2001 | Rajagopalan et al. |
| 6,287,793 B1 | 9/2001 | Schenk et al. |
| 6,322,494 B1 | 11/2001 | Bullivant et al. |
| 6,325,475 B1 | 12/2001 | Hayes et al. |
| 6,329,531 B1 | 12/2001 | Turner et al. |
| 6,338,715 B1 | 1/2002 | Hayes et al. |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,358,681 B2 | 3/2002 | Ginsberg et al. |
| 6,360,122 B1 | 3/2002 | Fischell et al. |
| 6,405,079 B1 | 6/2002 | Ansarinia |
| 6,410,046 B1 | 6/2002 | Lerner |
| 6,415,184 B1 | 7/2002 | Ishikawa et al. |
| 6,427,086 B1 | 7/2002 | Fischell et al. |
| 6,432,986 B2 | 8/2002 | Levin |
| 6,459,936 B2 | 10/2002 | Fischell et al. |
| 6,466,822 B1 | 10/2002 | Pless |
| 6,470,212 B1 | 10/2002 | Weijand et al. |
| 6,473,639 B1 | 10/2002 | Fischell et al. |
| 6,473,644 B1 | 10/2002 | Terry, Jr. et al. |
| 6,480,743 B1 | 11/2002 | Kirkpatrick et al. |
| 6,491,940 B1 | 12/2002 | Levin |
| 6,526,318 B1 | 2/2003 | Ansarinia |
| 6,529,774 B1 | 3/2003 | Greene |
| 6,531,454 B1 | 3/2003 | Leary et al. |
| 6,587,719 B1 | 7/2003 | Barrett et al. |
| 6,587,724 B2 | 7/2003 | Mann |
| 6,591,137 B1 | 7/2003 | Fischell et al. |
| 6,591,138 B1 | 7/2003 | Fischell et al. |
| 6,597,953 B2 | 7/2003 | Boling |
| 6,597,954 B1 | 7/2003 | Pless et al. |
| 6,606,521 B2 | 8/2003 | Paspa et al. |
| 6,609,025 B2 | 8/2003 | Barrett et al. |
| 6,609,032 B1 | 8/2003 | Woods et al. |
| 6,609,956 B2 | 8/2003 | Margaria |
| 6,618,623 B1 | 9/2003 | Pless et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,640,137 B2 | 10/2003 | MacDonald |
| 6,647,296 B2 | 11/2003 | Fischell et al. |
| 6,662,035 B2 | 12/2003 | Sochor |
| 6,671,555 B2 | 12/2003 | Gielen et al. |
| 6,671,556 B2 | 12/2003 | Osorio et al. |
| 6,678,553 B2 | 1/2004 | Lerner et al. |
| 6,690,974 B2 | 2/2004 | Archer et al. |
| 6,735,474 B1 | 5/2004 | Loeb et al. |
| 6,735,475 B1 | 5/2004 | Whitehurst et al. |
| 6,755,837 B2 | 6/2004 | Ebner |
| 6,782,292 B2 | 8/2004 | Whitehurst |
| 6,788,975 B1 | 9/2004 | Whitehurst et al. |
| 6,793,664 B2 | 9/2004 | Mazzocchi et al. |
| 6,810,285 B2 | 10/2004 | Pless et al. |

(56) References Cited

U.S. PATENT DOCUMENTS

| | | |
|---|---|---|
| 6,811,788 B2 | 11/2004 | Yu |
| 6,853,858 B2 | 2/2005 | Shalev |
| 6,860,264 B2 | 3/2005 | Christopher |
| 6,905,827 B2 | 6/2005 | Wohlgemuth et al. |
| 6,922,590 B1 | 7/2005 | Whitehurst |
| 7,003,352 B1 | 2/2006 | Whitehurst |
| 7,117,033 B2 * | 10/2006 | Shalev ............... A61N 1/0546 607/2 |
| 7,120,489 B2 | 10/2006 | Shalev et al. |
| 7,146,209 B2 | 12/2006 | Gross et al. |
| 7,190,998 B2 | 3/2007 | Shalev et al. |
| 7,331,113 B1 | 2/2008 | Patrick et al. |
| 7,561,919 B2 | 7/2009 | Shalev et al. |
| 7,574,025 B2 | 8/2009 | Feldman |
| 7,636,597 B2 | 12/2009 | Gross et al. |
| 7,640,062 B2 | 12/2009 | Shalev |
| 7,664,347 B2 | 2/2010 | Childers et al. |
| 7,684,859 B2 | 3/2010 | Shalev et al. |
| 7,720,322 B2 | 5/2010 | Prisco |
| 7,772,541 B2 | 8/2010 | Froggatt et al. |
| 7,781,724 B2 | 8/2010 | Childers et al. |
| 7,813,599 B2 | 10/2010 | Moore |
| 7,860,569 B2 | 12/2010 | Solberg et al. |
| 7,908,000 B2 | 3/2011 | Shalev |
| 8,050,523 B2 | 11/2011 | Younge et al. |
| 8,055,347 B2 | 11/2011 | Lamensdorf et al. |
| 8,113,829 B2 | 2/2012 | Sachdeva et al. |
| 8,135,194 B2 | 3/2012 | Feldman |
| 8,229,571 B2 | 7/2012 | Lorian |
| 8,296,952 B2 | 10/2012 | Greenberg |
| 8,406,869 B2 | 3/2013 | Lamensdorf |
| 8,435,033 B2 | 5/2013 | Gross et al. |
| 8,460,236 B2 | 6/2013 | Roelle et al. |
| 8,682,043 B2 | 3/2014 | Cahill et al. |
| 8,780,339 B2 | 7/2014 | Udd |
| 8,989,528 B2 | 3/2015 | Udd |
| 9,050,131 B2 | 6/2015 | Van Vorhis et al. |
| 9,138,166 B2 | 9/2015 | Wong et al. |
| 2001/0004644 A1 | 6/2001 | Levin |
| 2001/0014670 A1 | 8/2001 | Balin et al. |
| 2001/0018191 A1 | 8/2001 | Mercken et al. |
| 2001/0020097 A1 | 9/2001 | Audia et al. |
| 2001/0026916 A1 | 10/2001 | Ginsberg et al. |
| 2001/0027309 A1 | 10/2001 | Elsberry |
| 2001/0044126 A1 | 11/2001 | Holtzman et al. |
| 2001/0047014 A1 | 11/2001 | Alanine et al. |
| 2001/0051633 A1 | 12/2001 | Bigge et al. |
| 2002/0002270 A1 | 1/2002 | Zinkowski et al. |
| 2002/0006627 A1 | 1/2002 | Reitz et al. |
| 2002/0009445 A1 | 1/2002 | Du et al. |
| 2002/0019016 A1 | 2/2002 | Vanmechelen et al. |
| 2002/0019412 A1 | 2/2002 | Andersen et al. |
| 2002/0019519 A1 | 2/2002 | Bingham et al. |
| 2002/0022242 A1 | 2/2002 | Small et al. |
| 2002/0022593 A1 | 2/2002 | Yue |
| 2002/0022621 A1 | 2/2002 | Chaturvedula et al. |
| 2002/0022650 A1 | 2/2002 | Posmantur et al. |
| 2002/0025955 A1 | 2/2002 | Han et al. |
| 2002/0026652 A1 | 2/2002 | Allen et al. |
| 2002/0028462 A1 | 3/2002 | Tanzi et al. |
| 2002/0028834 A1 | 3/2002 | Villalobos et al. |
| 2002/0035145 A1 | 3/2002 | Tsai et al. |
| 2002/0040032 A1 | 4/2002 | Glasky et al. |
| 2002/0040052 A1 | 4/2002 | Ito et al. |
| 2002/0042121 A1 | 4/2002 | Rienser et al. |
| 2002/0042420 A1 | 4/2002 | Briem et al. |
| 2002/0044919 A1 | 4/2002 | Yu |
| 2002/0052311 A1 | 5/2002 | Solomon et al. |
| 2002/0055501 A1 | 5/2002 | Olson et al. |
| 2002/0055761 A1 | 5/2002 | Mann et al. |
| 2002/0066959 A1 | 6/2002 | Joshi |
| 2002/0068080 A1 | 6/2002 | Lerner |
| 2002/0077687 A1 | 6/2002 | Ahn |
| 2002/0082583 A1 | 6/2002 | Lerner |
| 2002/0099412 A1 | 7/2002 | Fischell et al. |
| 2002/0099417 A1 | 7/2002 | Naritoku et al. |
| 2002/0123678 A1 | 9/2002 | Lerner et al. |
| 2002/0133841 A1 | 9/2002 | Leviten |
| 2002/0169307 A1 | 11/2002 | Klein |
| 2002/0169485 A1 | 11/2002 | Pless et al. |
| 2002/0183683 A1 | 12/2002 | Lerner |
| 2003/0005473 A1 | 1/2003 | Brennan et al. |
| 2003/0005477 A1 | 1/2003 | Leviten |
| 2003/0013136 A1 | 1/2003 | Balser et al. |
| 2003/0014772 A1 | 1/2003 | Allen |
| 2003/0018988 A1 | 1/2003 | Allen et al. |
| 2003/0018989 A1 | 1/2003 | Brennan et al. |
| 2003/0036781 A1 | 2/2003 | Nuttin et al. |
| 2003/0050527 A1 | 3/2003 | Fox et al. |
| 2003/0051268 A1 | 3/2003 | Allen |
| 2003/0056238 A1 | 3/2003 | Wisotzkey |
| 2003/0073917 A1 | 4/2003 | Echauz et al. |
| 2003/0074033 A1 | 4/2003 | Pless et al. |
| 2003/0079742 A1 | 5/2003 | Giroux |
| 2003/0106083 A1 | 6/2003 | Allen |
| 2003/0131367 A1 | 7/2003 | Guenther et al. |
| 2003/0133877 A1 | 7/2003 | Levin |
| 2003/0144711 A1 | 7/2003 | Pless et al. |
| 2003/0149457 A1 | 8/2003 | Tcheng et al. |
| 2003/0166099 A1 | 9/2003 | Sabbadini et al. |
| 2003/0166279 A1 | 9/2003 | Sabbadini et al. |
| 2003/0172390 A1 | 9/2003 | Wisotzkey et al. |
| 2003/0176892 A1 | 9/2003 | Shalev |
| 2003/0176898 A1 | 9/2003 | Gross et al. |
| 2003/0177514 A1 | 9/2003 | Leviten |
| 2003/0190601 A1 | 10/2003 | Sabbadini et al. |
| 2003/0190683 A1 | 10/2003 | Sabbadini et al. |
| 2003/0190749 A1 | 10/2003 | Surber et al. |
| 2003/0191426 A1 | 10/2003 | Lerner et al. |
| 2003/0194714 A1 | 10/2003 | Sabbadini et al. |
| 2003/0195588 A1 | 10/2003 | Fischell et al. |
| 2003/0195602 A1 | 10/2003 | Boling |
| 2003/0198995 A1 | 10/2003 | Sabbadini et al. |
| 2003/0198996 A1 | 10/2003 | Surber et al. |
| 2003/0199005 A1 | 10/2003 | Sabbadini et al. |
| 2003/0199088 A1 | 10/2003 | Sabbadini et al. |
| 2003/0199089 A1 | 10/2003 | Surber et al. |
| 2003/0202937 A1 | 10/2003 | Sabbadini et al. |
| 2003/0203411 A1 | 10/2003 | Sabbadini et al. |
| 2003/0203481 A1 | 10/2003 | Surber et al. |
| 2003/0207833 A1 | 11/2003 | Berkley et al. |
| 2003/0211086 A1 | 11/2003 | Berkley et al. |
| 2003/0211599 A1 | 11/2003 | Sabbadini et al. |
| 2003/0219408 A1 | 11/2003 | Sabbadini et al. |
| 2003/0219888 A1 | 11/2003 | Segall et al. |
| 2003/0224369 A1 | 12/2003 | Surber et al. |
| 2003/0224444 A1 | 12/2003 | Sabbadini et al. |
| 2003/0232335 A1 | 12/2003 | Surber et al. |
| 2004/0015068 A1 | 1/2004 | Shalev et al. |
| 2004/0033491 A1 | 2/2004 | Alsobrook et al. |
| 2004/0054297 A1 | 3/2004 | Wingeier et al. |
| 2004/0133248 A1 | 7/2004 | Frei et al. |
| 2004/0136950 A1 | 7/2004 | Ni et al. |
| 2004/0136951 A1 | 7/2004 | Ni et al. |
| 2004/0138097 A1 | 7/2004 | Guyuron |
| 2004/0153129 A1 | 8/2004 | Pless et al. |
| 2004/0210269 A1 | 10/2004 | Shalev et al. |
| 2004/0220644 A1 | 11/2004 | Shalev et al. |
| 2004/0259051 A1 | 12/2004 | Brajnovic |
| 2005/0020519 A1 | 1/2005 | Albiston et al. |
| 2005/0021106 A1 | 1/2005 | Firlik et al. |
| 2005/0054939 A1 | 3/2005 | Ben-Ari et al. |
| 2005/0065427 A1 | 3/2005 | Magill et al. |
| 2005/0074506 A1 | 4/2005 | Natan et al. |
| 2005/0112090 A9 | 5/2005 | Ni et al. |
| 2005/0113877 A1 | 5/2005 | Spinelli et al. |
| 2005/0118187 A1 | 6/2005 | Yu |
| 2005/0137646 A1 | 6/2005 | Wallance et al. |
| 2005/0137647 A1 | 6/2005 | Wallance et al. |
| 2005/0154419 A1 | 7/2005 | Whitehurst et al. |
| 2005/0159790 A1 | 7/2005 | Shalev |
| 2005/0266099 A1 | 12/2005 | Shalev |
| 2006/0013523 A1 | 1/2006 | Childers |
| 2006/0020299 A1 | 1/2006 | Shalev |

(56) References Cited

U.S. PATENT DOCUMENTS

| | | |
|---|---|---|
| 2006/0085041 A1 | 4/2006 | Hastings et al. |
| 2006/0089678 A1 | 4/2006 | Shalev |
| 2006/0154199 A1 | 7/2006 | Maxwell et al. |
| 2006/0195169 A1 | 8/2006 | Gross et al. |
| 2006/0287677 A1 | 12/2006 | Shalev et al. |
| 2006/0291968 A1 | 12/2006 | Greenberg |
| 2006/0293723 A1 | 12/2006 | Whitehurst et al. |
| 2007/0083245 A1 | 4/2007 | Lamensdorf et al. |
| 2008/0033509 A1 | 2/2008 | Shalev et al. |
| 2008/0161680 A1 | 7/2008 | Von Jako et al. |
| 2008/0172102 A1 | 7/2008 | Shalev |
| 2009/0105783 A1 | 4/2009 | Solberg et al. |
| 2009/0131739 A1 | 5/2009 | Shalev |
| 2009/0210026 A1 | 8/2009 | Solberg et al. |
| 2009/0263764 A1 | 10/2009 | Berckmans et al. |
| 2009/0299418 A1 | 12/2009 | Shalev et al. |
| 2010/0035201 A1 | 2/2010 | Beck et al. |
| 2010/0049230 A1 | 2/2010 | Benary et al. |
| 2010/0082148 A1 | 4/2010 | Cinader |
| 2010/0114184 A1* | 5/2010 | Degtyar .......... A61B 17/1659 606/86 R |
| 2010/0168513 A1 | 7/2010 | Pless et al. |
| 2010/0332248 A1 | 12/2010 | Pettersson |
| 2011/0008751 A1 | 1/2011 | Pettersson |
| 2011/0060558 A1 | 3/2011 | Pettersson et al. |
| 2011/0160731 A1 | 6/2011 | Bleich et al. |
| 2011/0275029 A1 | 11/2011 | Gao |
| 2011/0301670 A1 | 12/2011 | Gross et al. |
| 2012/0016434 A1 | 1/2012 | Lamensdorf et al. |
| 2012/0046536 A1 | 2/2012 | Cheung et al. |
| 2012/0123576 A1 | 5/2012 | Pettersson et al. |
| 2012/0191421 A1 | 7/2012 | Greenberg |
| 2012/0214121 A1 | 8/2012 | Greenberg |
| 2012/0290057 A1 | 11/2012 | Boling et al. |
| 2012/0316486 A1 | 12/2012 | Cheung et al. |
| 2013/0066393 A1 | 3/2013 | Gross et al. |
| 2013/0150732 A1 | 6/2013 | Manzke et al. |
| 2013/0184803 A1 | 7/2013 | Altman |
| 2013/0273492 A1 | 10/2013 | Suttin et al. |
| 2013/0280674 A1 | 10/2013 | Maksim |
| 2013/0281990 A1 | 10/2013 | Manzke et al. |
| 2014/0096369 A1 | 4/2014 | Matsumoto et al. |
| 2014/0120488 A1 | 5/2014 | Greenberg |
| 2014/0206988 A1 | 7/2014 | Ramachandran et al. |
| 2014/0234804 A1 | 8/2014 | Huang et al. |
| 2014/0243660 A1 | 8/2014 | Klinder et al. |
| 2015/0133956 A1 | 5/2015 | Dayan et al. |

FOREIGN PATENT DOCUMENTS

| | | |
|---|---|---|
| CA | 2433376 | 8/2002 |
| EP | 0610301 | 2/1998 |
| EP | 0726791 | 6/2000 |
| EP | 0588957 | 9/2000 |
| EP | 0613389 | 9/2001 |
| EP | 1559369 | 8/2005 |
| EP | 0814089 | 10/2005 |
| EP | 1743575 A2 | 1/2007 |
| EP | 2186474 A1 | 5/2010 |
| EP | 2878335 | 6/2015 |
| WO | 89/02935 | 4/1989 |
| WO | 93/03762 | 3/1993 |
| WO | 93/09841 | 5/1993 |
| WO | 93/25271 | 12/1993 |
| WO | 94/00185 | 1/1994 |
| WO | 94/00188 | 1/1994 |
| WO | 94/00189 | 1/1994 |
| WO | 95/14028 | 5/1995 |
| WO | 97/18855 | 5/1997 |
| WO | 98/30709 | 7/1998 |
| WO | 99/03473 | 1/1999 |
| WO | 99/56822 | 11/1999 |
| WO | 00/44432 | 8/2000 |
| WO | 00/73343 | 12/2000 |
| WO | 01/00402 | 1/2001 |
| WO | 01/26729 | 4/2001 |
| WO | 01/38581 | 5/2001 |
| WO | 01/43733 | 6/2001 |
| WO | 01/52868 | 7/2001 |
| WO | 01/53455 | 7/2001 |
| WO | 01/57190 | 8/2001 |
| WO | 01/67855 | 9/2001 |
| WO | 01/85094 | 11/2001 |
| WO | 01/88088 | 11/2001 |
| WO | 01/97905 | 12/2001 |
| WO | 01/97906 | 12/2001 |
| WO | 01/98508 | 12/2001 |
| WO | 02/04068 | 1/2002 |
| WO | 02/06339 | 1/2002 |
| WO | 02/06445 | 1/2002 |
| WO | 02/16439 | 2/2002 |
| WO | 02/32504 | 4/2002 |
| WO | 02/42735 | 5/2002 |
| WO | 02/45498 | 6/2002 |
| WO | 02/46229 | 6/2002 |
| WO | 02/46390 | 6/2002 |
| WO | 02/46409 | 6/2002 |
| WO | 02/47477 | 6/2002 |
| WO | 02/48345 | 6/2002 |
| WO | 02/057450 | 7/2002 |
| WO | 02/059315 | 8/2002 |
| WO | 02/062291 | 8/2002 |
| WO | 02/064791 | 8/2002 |
| WO | 02/066643 | 8/2002 |
| WO | 02/068029 | 9/2002 |
| WO | 02/068031 | 9/2002 |
| WO | 02/079424 | 10/2002 |
| WO | 02/079438 | 10/2002 |
| WO | 02/079439 | 10/2002 |
| WO | 02/079440 | 10/2002 |
| WO | 02/079444 | 10/2002 |
| WO | 02/081510 | 10/2002 |
| WO | 02/081658 | 10/2002 |
| WO | 02/094191 | 11/2002 |
| WO | 03/000046 | 1/2003 |
| WO | 03/000310 | 1/2003 |
| WO | 03/001883 | 1/2003 |
| WO | 03/011304 | 2/2003 |
| WO | 03/011392 | 2/2003 |
| WO | 03/011393 | 2/2003 |
| WO | 03/018107 | 3/2003 |
| WO | 03/018108 | 3/2003 |
| WO | 03/020350 | 3/2003 |
| WO | 03/026395 | 4/2003 |
| WO | 03/026401 | 4/2003 |
| WO | 03/033672 | 4/2003 |
| WO | 03/063959 | 8/2003 |
| WO | 03/072014 | 9/2003 |
| WO | 03/076008 | 9/2003 |
| WO | 03/079742 | 9/2003 |
| WO | 03/080795 | 10/2003 |
| WO | 03/084591 | 10/2003 |
| WO | 03/090599 | 11/2003 |
| WO | 03/105658 | 12/2003 |
| WO | 2004/001092 | 12/2003 |
| WO | 04/010923 | 2/2004 |
| WO | 04/043217 | 5/2004 |
| WO | 04/043218 | 5/2004 |
| WO | 04/043334 | 5/2004 |
| WO | 04/044947 | 5/2004 |
| WO | 04/045242 | 5/2004 |
| WO | 04/064918 | 8/2004 |
| WO | 04/098515 | 11/2004 |
| WO | 04/113391 | 12/2004 |
| WO | 2005/002467 | 1/2005 |
| WO | 2005/015404 | 2/2005 |
| WO | 05/030025 | 4/2005 |
| WO | 05/030118 | 4/2005 |
| WO | 05/062829 | 7/2005 |
| WO | 06/021957 | 3/2006 |
| WO | 2011/154937 | 12/2011 |
| WO | 2012/151412 A1 | 11/2012 |

(56) References Cited

FOREIGN PATENT DOCUMENTS

| WO | 2013/102783 | 7/2013 |
|---|---|---|
| WO | 2013/111137 | 8/2013 |
| WO | 2014/037524 A1 | 3/2014 |

OTHER PUBLICATIONS

Hara H, Zhang QJ, Kuroyanagi T, Kobayashi S, "Parasympathetic cerebrovascular innervation: An anterograde tracing from the sphenopalatine ganglion in the rat," Neurosurgery, 32, 822-827 (1993).

Jolliet-Riant P, Tillement JP, "Drug transfer across the blood-brain barrier and improvement of brain delivery," Fundam. Clin. Pharmacol., 13, 16-26 (1999).

Kroll RA, Neuwelt EA, "Outwitting the blood brain barrier for therapeutic purposes: Osmotic opening and other means," Neurosurgery, 42, 1083-1100 (1998).

Sanders M, Zuurmond WW, "Efficacy of sphenopalatine ganglion blockade in 66 patients suffering from cluster headache: A 12-70 month follow-up evaluation," Journal of Neurosurgery, 87, 876-880 (1997).

Seylaz J, Hara H, Pinard E, Mraovitch S, MacKenzie ET, Edvinsson L, "Effects of stimulation of the sphenopalatine ganglion on cortical blood flow in the rat," Journal of Cerebral Blood Flow and Metabolism, 8, 875-878 (1988).

Waterbeemd Van de H, Camenisch G, Folkers G, Chretien JR, Raevsky OA, "Estimation of blood brain barrier crossing of drugs using molecular size and shape and h bonding descriptors," Journal of Drug Targeting, 6, 151-165, (1998).

Suzuki N, et al. "Selective electrical stimulation of postganglionic cerebrovascular parasympathetic nerve fibers originating from the sphenopalatine ganglion enhances cortical blood flow in the rat," Journal of Cerebral Blood Flow and Metabolism, 10, 383-391 (1990).

Suzuki N, Hardebo JE, Kahrstrom J, Owman CH, "Effect on cortical blood flow of electrical stimulation of trigeminal cerebrovascular nerve fibres in the rat," Acta Physiol. Scand., 138, 307-315 (1990).

Major A, Silver W, "Odorants presented to the rat nasal cavity increase cortical blood flow," Chem. Senses, 24, 665-669 (1999).

Fusco BM, Fiore G, Gallo F, Martelletti P, Giacovazzo M, "'Capsaicin-sensitive' sensory neurons in cluster headache: pathophysiological aspects and therapeutic indications," Headache, 34, 132-137 (1994).

Lambert GA, Bogduk N, Goadsby PJ, Duckworth JW, Lance JW, "Decreased carotid arterial resistance in cats in response to trigeminal stimulation," Journal of Neurosurgery, 61, 307-315 (1984).

Silver WL, "Neural and pharmacological basis for nasal irritation," in Tucker WG, Leaderer BP, Mølhave L, Cain WS (eds), Sources of Indoor Air Contaminants, Ann. NY Acad. Sci., 641, 152-163 (1992).

Branston NM, "The physiology of the cerebrovascular parasympathetic innervation," British Journal of Neurosurgery 9:319-329 (1995).

Branston NM et al., "Contribution of cerebrovascular parasympathetic and sensory innervation to the short-term control of blood flow in rat cerebral cortex," J Cereb Blood Flow Metab 15(3):525-31 (1995).

Toda N et al., "Cerebral vasodilation induced by stimulation of the pterygopalatine ganglion and greater petrosal nerve in anesthetized monkeys," Neuroscience 96(2):393-398 (2000).

Nollet H et al., "Transcranial magnetic stimulation: review of the technique, basic principles and applications," The Veterinary Journal 166:28-42 (2003).

Van Gijn J et al., "Subarachnoid haemorrhage: diagnosis, causes and management," Brain 124:249-278 (2001).

Goadsby PJ et al., "Effect of stimulation of trigeminal ganglion on regional cerebral blood flow in cats," Am J Physiol 22:R270-R274 (1987).

Walters BB et al., "Cerebrovascular projections from the sphenopalatine and otic ganglia to the middle cerebral artery of the cat," Stroke 17:488-494 (1986).

Suzuki N et al., "Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604 (1989).

Roth BJ et al., "In vitro evaluation of a 4-leaf coil design for magnetic stimulation of peripheral nerve," Electroencephalography and Clinical Neurophysiology 93:68-74 (1994).

Zhang R et al., "A nitric oxide donor induces neurogenesis and reduces functional deficits after stroke in rats," Ann Neurol 50:602-611 (2001).

Ziche M et al., "Nitric oxide and angiogenesis," J Neurooncol 50:139-148 (2000).

Zhang ZG et al., "VEGF enhances angiogenesis and promotes blood-brain barrier leakage in the ischemic brain," J Clin Invest 106:829-838 (2000).

Sun Y et al., "Neuronal nitric oxide synthase and ischemia-induced neurogenesis," J Cereb Blood Flow Metab 25(4):485-92 (2005).

Zhang F et al., "Nitric oxide donors increase blood flow and reduce brain damage in focal ischemia: evidence that nitric oxide is beneficial in the early stages of cerebral ischemia," J Cereb Blood Flow Metab 14(2):217-26 (1994).

USPTO Advisory Action dated Apr. 9, 2009 which issued during prosecution of Applicants' U.S. Appl. No. 10/535,024 (3 pages).

Davis SM et al., "Advances in penumbra imaging with MR," Cerebrovasc Dis 17 Suppl 3:23-7 (2004).

Phan TG et al., "Salvaging the ischaemic penumbra: more than just reperfusion?" Clin Exp Pharmacol Physiol 29(1-2):1-10 (2002).

Zhang R et al., "Nitric oxide enhances angiogenesis via the synthesis of vascular endothelial growth factor and cGMP after stroke in the rat," Circ Res 21;92(3):308-13 (2003).

de la Torre JC, "Vascular basis of Alzheimer's pathogenesis," Ann NY Acad Sci 977:196-215 (2002).

Roman GC, "Cholinergic dysfunction in vascular dementia," Curr Psychiatry Rep 7(1):18-26 (2005).

Lee, Tony JF, "Nitric oxide and the cerebral vascular function," J Biomed Sci 7:16-26 (2000).

Pluta RM, "Delayed cerebral vasospasm and nitric oxide: review, new hypothesis, and proposed treatment," Pharmacol Ther 105(1):23-56 (2005).

Sandgren K et al., "Vasoactive intestinal peptide and nitric oxide promote survival of adult rat myenteric neurons in culture," J Neurosci Res 72(5):595-602 (2003).

Laude K et al., "NO produced by endothelial NO synthase is a mediator of delayed preconditioning-induced endothelial protection," Am J Physiol Heart Circ Physiol 284(6):H2053-60 (2003) (Epub Jan. 9, 2003).

Khan M et al., "S-Nitrosoglutathione reduces inflammation and protects brain against focal cerebral ischemia in a rat model of experimental stroke," J Cereb Blood Flow Metab 25(2):177-92 (2005).

Schmid-Elsaesser R et al., "A critical reevaluation of the intraluminal thread model of focal cerebral ischemia. Evidence of inadvertent premature reperfusion and subarachnoid hemorrhage in rats by laser-Doppler flowmetry," Stroke 29:2162-2170 (1998).

Zausinger VS et al., "Neurological impairment in rats after transient middle cerebral artery occlusion: a comparative study under various treatment paradigms," Brain Research 863(1-2):94-105 (2000).

Hunter AJ et al., "To what extent have functional studies of ischemia in animals been useful in the assessment of potential neuroprotective agents?" Trends Pharmacol Sci 19:59-66 (1998).

Varghese et al., "Endoscopic transnasal neurolytic sphenopalatine ganglion block for head and neck cancer pain," J Laryngol Otol 115(5):385-7 (2001).

Hotta H et al., "Effects of stimulating the nucleus basalis of Meynert on blood flow and delayed neuronal death following transient ischemia in rat cerebral cortes," Jap J Phys 52:383-393 (2002).

Reis DJ et al., "Electrical stimulation of cerebellar fastigial nucleus reduces ischemic infarction elicited by middle cerebral artery occlusion in rat," J Cereb Blood Flow Metab 11(5):810-8 (1991).

(56) References Cited

OTHER PUBLICATIONS

Matsui T et al., "The effects of cervical spinal cord stimulation (cSCS) on experimental stroke," Pacing Clin Electrophysiol 12(4 Pt 2):726-32 (1989).
Sagher O et al., "Spinal cord stimulation reducing infract volume in model of focal cerebral ischemia in rats," J Neurosurg 99(1):131-137 (2003).
G.L. Ruskell, "The Orbital Branches of the Pterygopalatine Ganglion and their Relationship with Internal Carotid Nerve Branches in Primates", J. Anat. 1970, 106, 2, pp. 323-339.
Samad TA et al., in an article entitled, "Interleukin-1beta-mediated induction of Cox-2 in the CNS contributes to inflammatory pain hypersensitivity," in Nature 410(6827):471-5 (2001).
An Office Action dated Oct. 10, 2012 which issued during the prosecution of U.S. Appl. No. 12/575,165 (8 pages).
An Office Action dated Jan. 19, 2012 which issued during the prosecution of U.S. Appl. No. 12/575,165 (15 pages).
An Office Action dated May 3, 2016 which issued during the prosecution of U.S. Appl. No. 14/536,924 (6 pages).
Ronald F. Young, "Electrical Stimulation of the Trigeminal nerve root for the Treatment of Chronic Facial Pain", J Neurosurg 83:72-78, 1995.
An Office Action dated Jul. 28, 2016 which issued during the prosecution of U.S. Appl. No. 14/536,924 (51 pages).
Widmann G et al., "Use of a surgical navigation system for CT-guided template production," J Oral Maxillofac Implants Jan. 2007;22:72-78.
N. Suzuki, et al, "Origins and Pathways of Cerebrovascular Vasoactive Intestinal Polypeptide-Positive Nerves in Rat", J Cereb Blood Flow Metab. vol. 8 No. 5, 1988.
Kanner AA et al., "Serum S100beta: a noninvasive marker of blood-brain barrier function and brain lesions," Cancer 97(11):2806-13 (2003).
Fu Yung-Hui, et al., "Improved bioavailability of orally administered drugs by Chinese herbal enhancers through modulation of P-glycoprotein", ASHP 39th Midyear Clinical Meeting and Exhibits, Dec. 5-9, 2004.
J.D. Wong, et al., "Maxillary nerve block anaesthesia via the greater palatine canal: A modified technique and case reports", Australian Dental Journal, 1991;36(1):15-21.
A Supplementary European Search Report dated Nov. 5, 2009, which issued during the prosecution Applicant's Eurpean Patent Application Number 04 77 0568 (3 pages).
U.S. Appl. No. 61/195,556, filed Oct. 7, 2008 (69 pages).
European Search Report dated Jul. 11, 2016, which issued during the prosecution of Applicant's European Patent Application No. 16169657. (5 pages).
An International Search Report dated May 26, 2006 which issued during the prosecution of Applicant's PCT/IL03/00966 (2 pages).
Branimir I. Sikic, et al., "Modulation and prevention of multidrug resistance by inhibitors of P-glycoprotein", Cancer Chemother Pharmacol (1997), 40 (Suppl):S13-S19.
A Written opinion dated Feb. 4, 2004 which issued during the prosecution of Applicant's PCT/IL03/00966 (7 pages).
U.S. Appl. No. 60/604,037, filed Aug. 23, 2004 (39 pages).
U.S. Appl. No. 60/203,172, filed May 8, 2000 (25 pages).
U.S. Appl. No. 60/364,451, filed Mar. 15, 2002 (40 pages).
U.S. Appl. No. 60/368,657, filed Mar. 28, 2002 (41 pages).
U.S. Appl. No. 60/376,048, filed Apr. 25, 2002 (49 pages).
U.S. Appl. No. 60/388,931, filed Jun. 14, 2002 (97 pages).
U.S. Appl. No. 60/400,167, filed Jul. 31, 2002 (66 pages).
U.S. Appl. No. 60/426,180, filed Nov. 14, 2002 (28 pages).
U.S. Appl. No. 60/426,182, filed Nov. 14, 2002 (28 pages).
Devoghel JC, "Cluster headache and sphenopalatine block," Acta Anaesthesiol Belg., 32(1):101-7 (1981).
U.S. Appl. No. 60/426,181, filed Nov. 14, 2002 (47 pages).
U.S. Appl. No. 60/448,807, filed Feb. 20, 2003 (84 pages).
U.S. Appl. No. 60/461,232, filed Apr. 8, 2003 (85 pages).
U.S. Appl. No. 60/506,165, filed Sep. 26, 2003 (67 pages).
U.S. Appl. No. 60/709,734, filed Aug. 19, 2005 (84 pages).
U.S. Appl. No. 60/531,224, filed Dec. 19, 2003 (30 pages).
U.S. Appl. No. 60/265,008, filed Jan. 30, 2001 (24 pages).
U.S. Appl. No. 60/383,317, filed May 24, 2002 (29 pages).
U.S. Appl. No. 60/505,831, filed Sep. 25, 2003 (28 pages).
Schwartz-Arad et al., "Maxillary nerve block—A new approach using a computer-controlled anesthetic delivery system for maxillary sinus elevation procedure. A prospective study," Quintessence International 2004; 35:477-480.
An Office Action dated Oct. 4, 2005 which issued during the prosecution of U.S. Appl. No. 10/294,310 (8 pages).
An Office Action dated Jan. 15, 2013 which issued during the prosecution of U.S. Appl. No. 13/348,731 (7 pages).
An Office Action dated Nov. 15, 2011 which issued during the prosecution of U.S. Appl. No. 12/612,993 (6 pages).
An Office Action dated Jun. 27, 2008 which issued during the prosecution of U.S. Appl. No. 10/518,322 (7 pages).
Nissen et al., "Effect of very high-intensity statin therapy on regression of coronary atherosclerosis: The ASTEROID Trial," JAMA 2006, 295(13):1556-1565.
An Office Action dated Jun. 12, 2008 which issued during the prosecution of U.S. Appl. No. 10/535,024 (8 pages).
An Office Action dated Nov. 20, 2008 which issued during the prosecution of U.S. Appl. No. 10/535,024 (5 pages).
An Office Action dated Aug. 6, 2009 which issued during the prosecution of U.S. Appl. No. 10/535,024 (4 pages).
An Office Action dated Dec. 16, 2005 which issued during the prosecution of U.S. Appl. No. 10/753,882 (7 pages).
J. MORITA MFG. CORP., "Root ZX® II—Endodontic Predictability Apex Locator with Low Speed Handpiece," 2008 (Morita Brochure) (12 pages).
An Office Action dated Mar. 29, 2006 which issued during the prosecution of U.S. Appl. No. 10/783,113 (6 pages).
An Office Action dated Jun. 13, 2006 which issued during the prosecution of U.S. Appl. No. 10/783,113 (4 pages).
An Office Action dated Jul. 16, 2008 which issued during the prosecution of U.S. Appl. No. 11/349,020 (9 pages).
An Office Action dated Mar. 23, 2009 which issued during the prosecution of U.S. Appl. No. 11/349,020 (4 pages).
An Office Action dated Dec. 12, 2013 which issued during the prosecution of Applicant's European App No. 03775767 (6 pages).
European Search Report dated Dec. 20, 2006 which issued during the prosecution of Applicant's European App No. 06017239 (8 pages).
European Search Report dated Jan. 4, 2011 which issued during the prosecition of Applicant's European App No. 03775767 (3 pages).
An Office Action dated Aug. 23, 2010 which issued during the prosecution of U.S. Appl No. 11/928,024 (19 pages).
Kawamata T et al., "Intracisternal basic fibroblast growth factor (bFGF) enhances behavioral recovery following focal cerebral infarction in the rat," J Cereb Blood Flow Metab 16:542-547 (1996).
An Office Action dated Feb. 17, 2009 which issued during the prosecution of U.S. Appl. No. 11/668,305 (6 pages).
J.M. Gallo, et al., "The effect of P-glycoprotein on Paclitaxel Brain and Brain Tumor Distribution in Mice" Cancer Research 63, 5114-5117, Aug. 2003.
Notice of Allowance dated Nov. 15, 2010 which issued during the prosecution of U.S. Appl. No. 11/931,154 (4 pages).
An Office Action dated Jun. 9, 2010 which issued during the prosecution of U.S. Appl. No. 11/931,154 (7 pages).
An Office Action dated Apr. 26, 2012 which issued during the prosecution of U.S. Appl. No. 12/612,993 (5 pages).
An Office Action dated Dec. 19, 2005 which issued during the prosecution of U.S. Appl. No. 10/783,113 (5 pages).
An Office Action dated Oct. 28, 2011, which issued during the prosecution of U.S. Appl. No. 12/575,165 (9 pages).
Jung RE et al., "Computer technology applications in surgical implant dentistry: a systematic review," J Oral Maxillofac Implants Jan. 2009;24(Suppl):92-109.
Jones, PE, "Creating Surgical Guides Using CBCT and Intraoral Scanning," Guidewelldental.com, dowloaded Nov. 7, 2014 (10 pages).
Almog DM et al., "CT-Based dental imaging for implant planning and surgical guidance: a case report," NYSDJ, Jan. 2007 (3 pages).

(56) References Cited

OTHER PUBLICATIONS

European Search Report dated Sep. 21, 2015 which issued during the prosecution of Applicant's European App No. 14192536 (9 pages).
Supplementary European Search Report dated May 4, 2015, which issued during the prosecition of Applicant's European App No. 14192536 (6 pages).
European Search Report dated Mar. 9, 2015 which issued during the prosecution of Applicant's European App No. 04770568.6 (5 pages).
U.S. Appl. No. 62/160/708, filed May 13, 2015 (63 pages).
Partial European Search Report dated Apr. 11, 2018, which issued during the prosecution of Applicant's European Patent Application No. 17201924.2, 15 pages.
Intention to Grant issued in European Patent Application No. 16 169 657.0 dated May 28, 2018, 63 pages.
Extended European Search Report dated Oct. 24, 2016, which issued during the prosecution of Applicant's European Patent Application No. 16 169 657.0 (4 pages).
European Search Report dated Aug. 6, 2018, which issued during the prosecution of Applicant's European Patent Application No. 17201924.2, 12 pages.

* cited by examiner

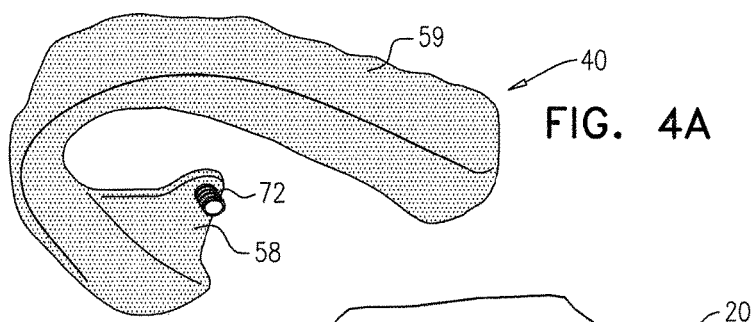
FIG. 4A
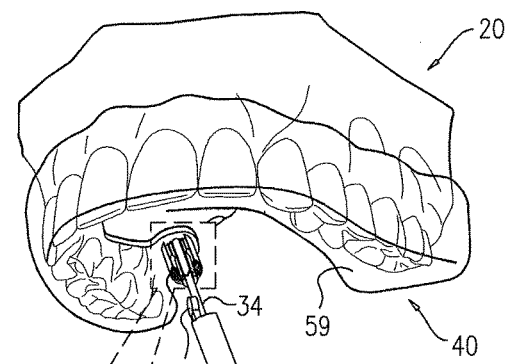
FIG. 4B
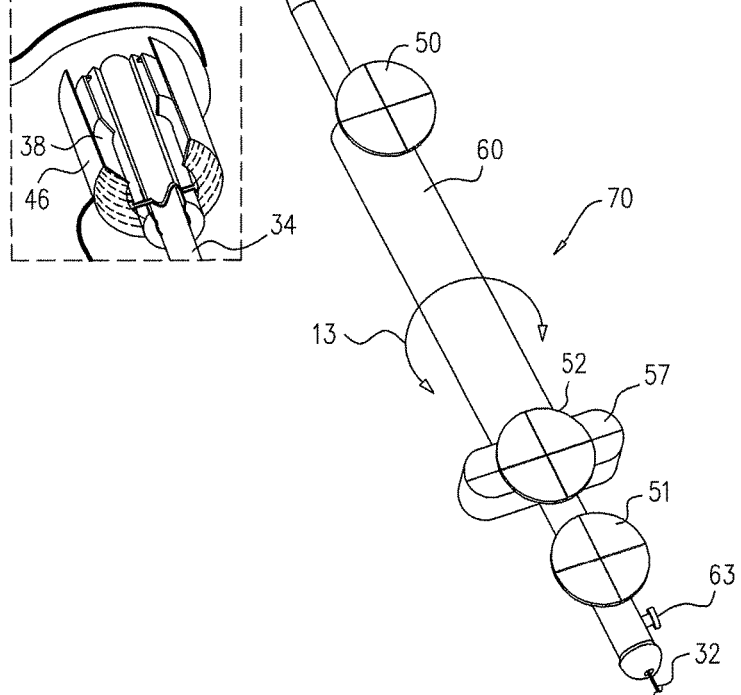

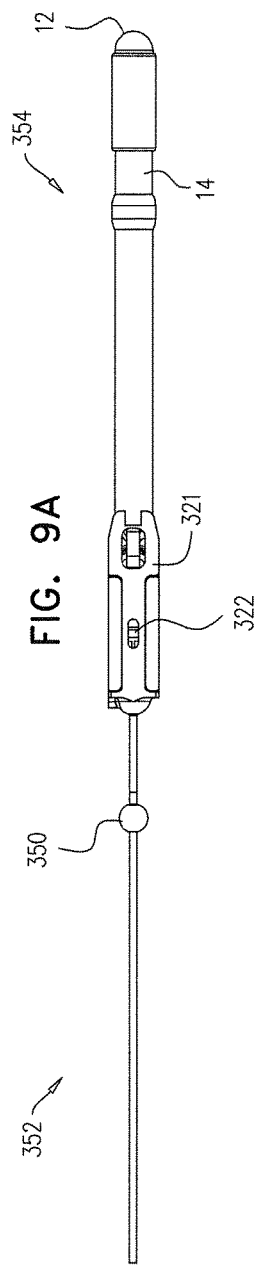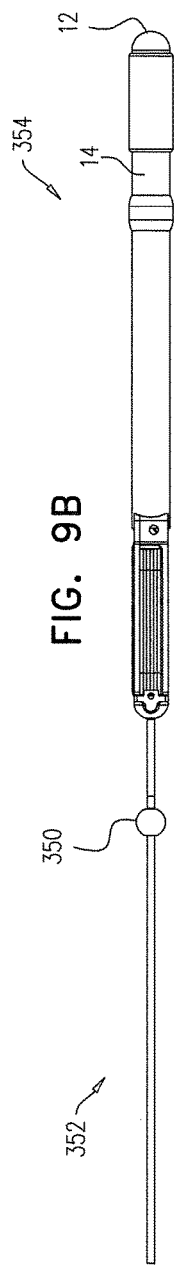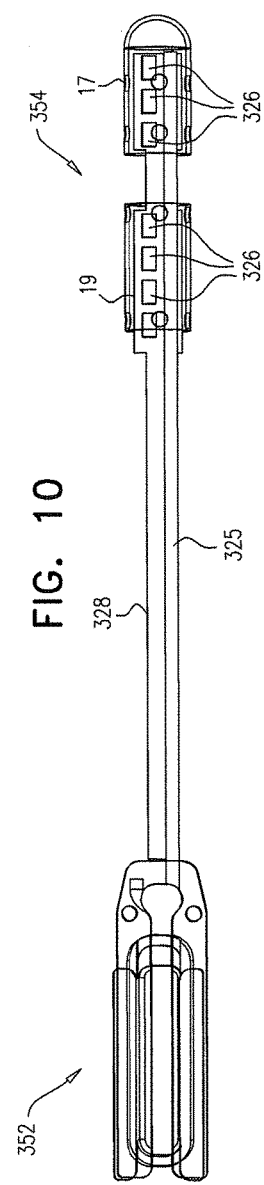

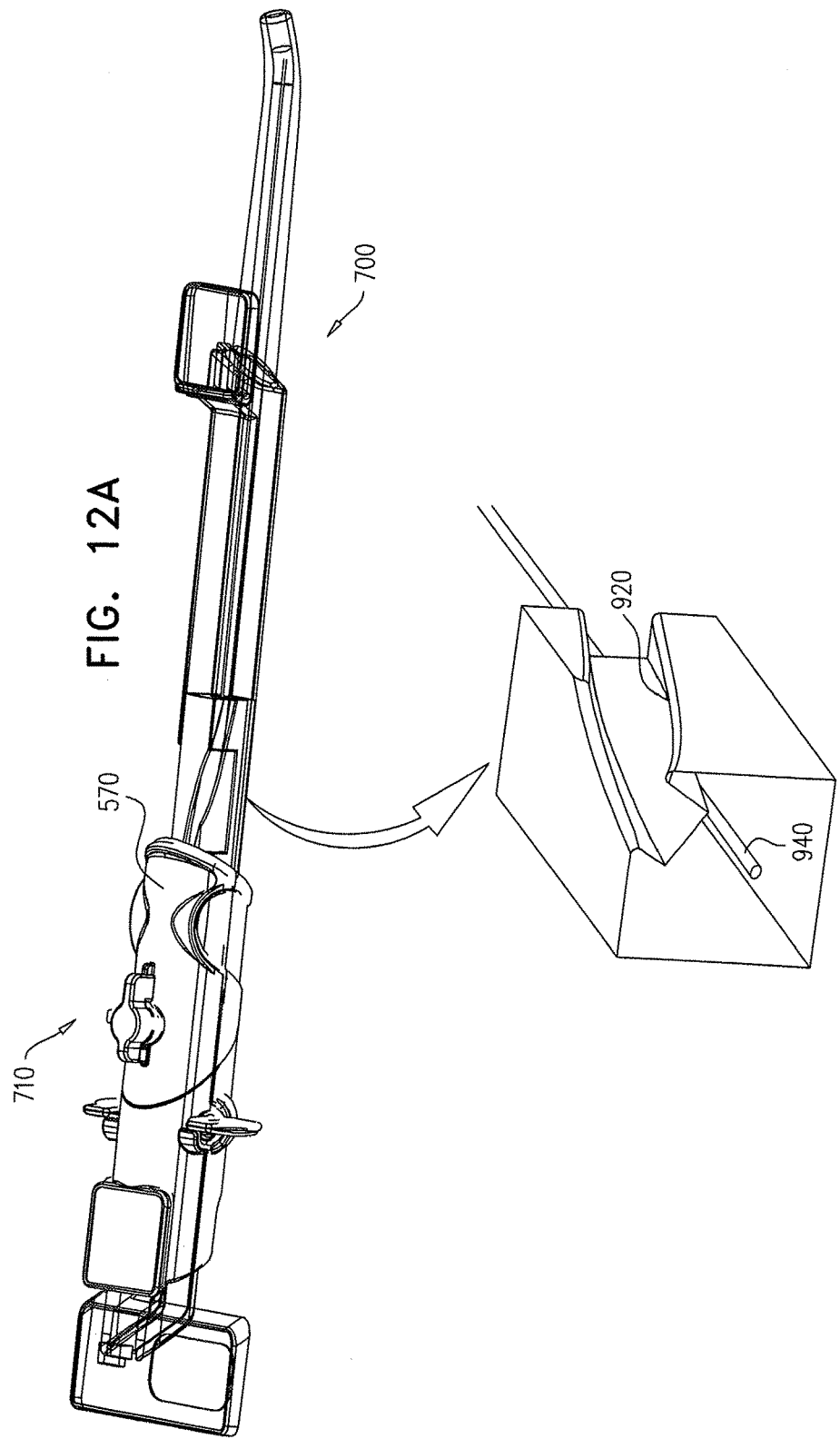

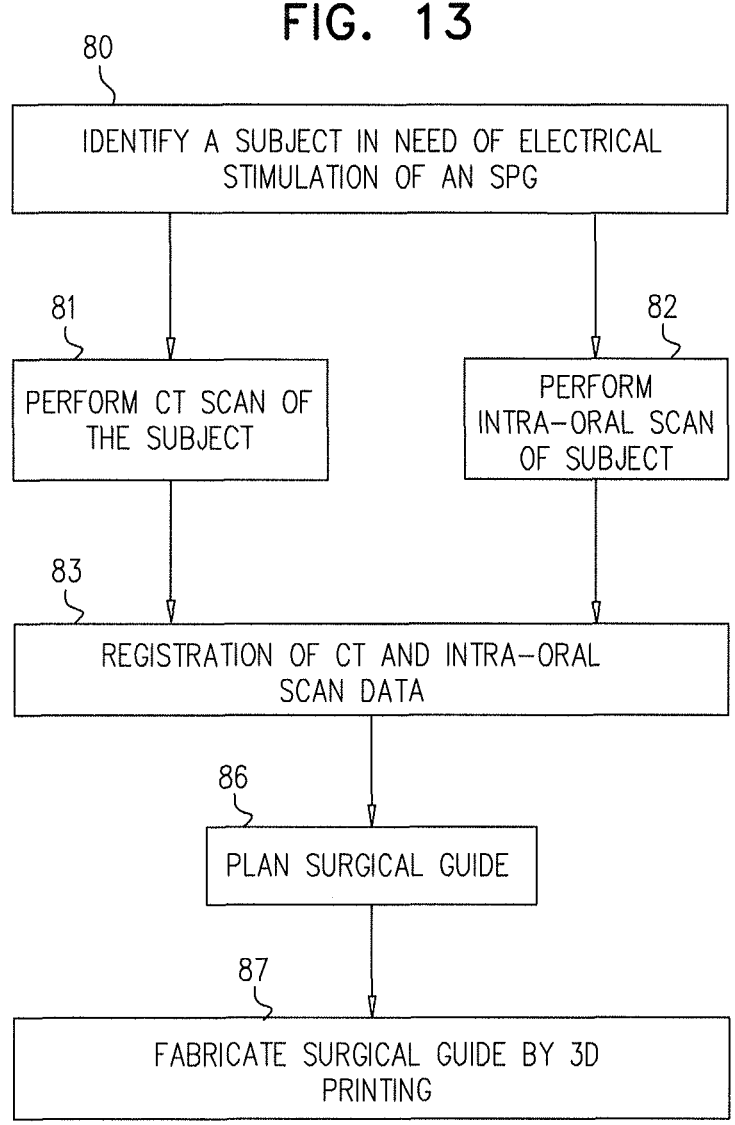

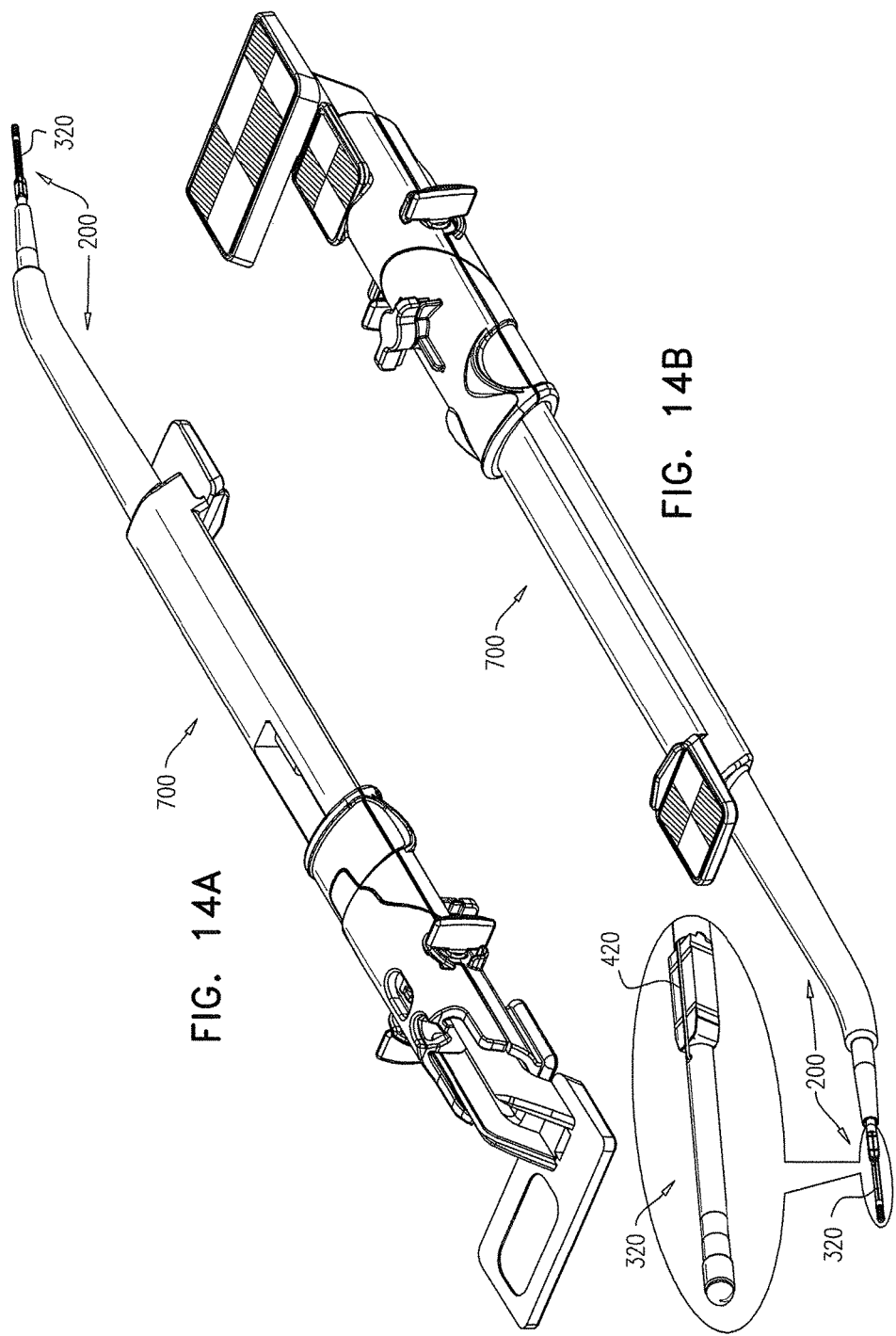

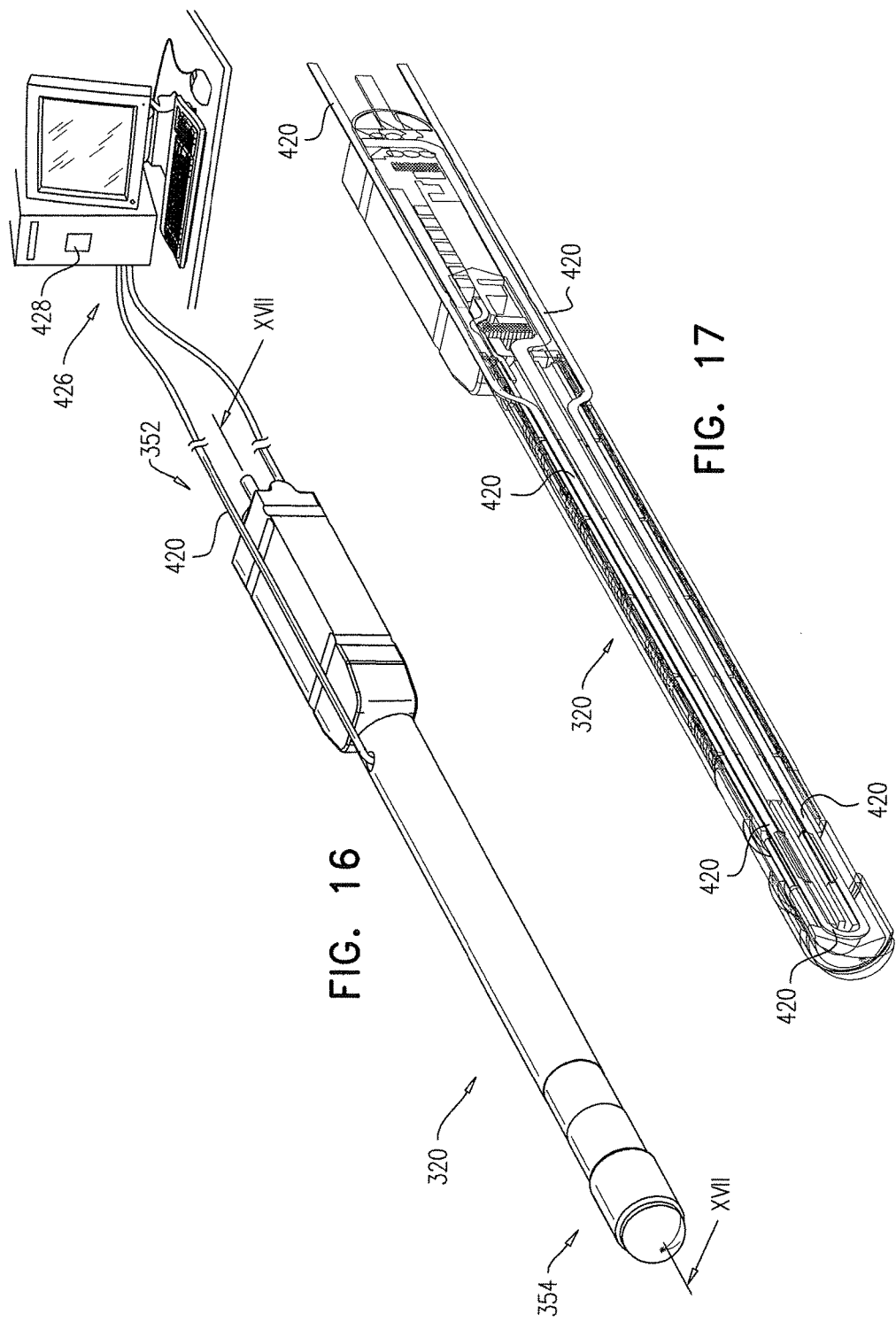

IMPLANT AND DELIVERY SYSTEM FOR NEURAL STIMULATOR

CROSS-REFERENCES TO RELATED APPLICATIONS

The present application claims priority from:

U.S. Provisional Application 62/160,708 to Dayan et al., entitled "Implant and delivery system for neural stimulator," filed May 13, 2015.

The present application is related to:

(a) U.S. application Ser. No. 14/536,924 to Dayan et al., entitled "Implant and delivery system for neural stimulator," filed Nov. 10, 2014, now U.S. Pat. No. 9,675,796;

(b) EP Application 14192536.2 to Dayan et al., entitled "Implant and delivery system for neural stimulator," filed Nov. 10, 2014 and published as EP2878335; and (c) Israel Patent Application No. 229345 to Dayan et al., entitled "Implant and delivery system for neural stimulator," filed Nov. 10, 2013; and (d) EP Application 14192536.2 to Dayan et al., filed Nov. 10, 2014, entitled "Implant and delivery system for neural stimulator,"

each of which is incorporated herein by reference.

FIELD OF THE APPLICATION

Some applications of the invention relate generally to medical procedures and implantable devices. More specifically, some applications of the invention relate to the use of electrical devices for implantation in the head.

BACKGROUND

Surgical guides are typically generated based on computed tomography (CT) image data, and provide a dentist with guidance as to an optimal location for drilling into a jaw bone of a subject during implantation of dental implants.

U.S. Pat. No. 7,120,489 to Shalev and Gross, which is assigned to the assignee of the present patent application and is incorporated herein by reference, describes apparatus for modifying a property of a brain of a patient, including electrodes applied to a sphenopalatine ganglion (SPG) or a neural tract originating in or leading to the SPG. A control unit drives the electrodes to apply a current capable of inducing (a) an increase in permeability of a blood-brain barrier (BBB) of the patient, (b) a change in cerebral blood flow of the patient, and/or (c) an inhibition of parasympathetic activity of the SPG.

U.S. Pat. No. 7,117,033 to Shalev et al., describes a method for treating a subject, comprising positioning at least one electrode at least one site of the subject for less than about 3 hours, applying an electrical current to the site of the subject, and configuring the current to increase cerebral blood flow (CBF) of the subject, so as to treat a condition of the subject. The site is selected from the list consisting of: a sphenopalatine ganglion (SPG) of the subject, a greater palatine nerve of the subject, a lesser palatine nerve of the subject, a sphenopalatine nerve of the subject, a communicating branch between a maxillary nerve and an SPG of the subject, an otic ganglion of the subject, an afferent fiber going into the otic ganglion of the subject, an efferent fiber going out of the otic ganglion of the subject, an infraorbital nerve of the subject, a vidian nerve of the subject, a greater superficial petrosal nerve of the subject, and a lesser deep petrosal nerve of the subject.

U.S. Pat. No. 7,561,919 to Shalev et al., describes apparatus for application to a subject, including an elongated support element having a length of between 1.8 cm and 4 cm, and having proximal and distal ends; and one or more electrodes fixed to the support element in a vicinity of the distal end thereof, and adapted to apply an electrical current to a sphenopalatine ganglion (SPG) of the subject. The apparatus further includes a receiver, fixed to the support element, and electrically coupled to the electrodes; and a wireless transmitter, adapted to be placed in an oral cavity of the subject, and to be wirelessly coupled to the receiver. Other embodiments are also described.

U.S. Pat. No. 7,772,541 to Froggatt et al., and US Patent Application Publication 2006-0013523 to Childlers et al., are each incorporated herein by reference.

SUMMARY OF APPLICATIONS

In some applications, a system is provided for delivery of a neural stimulator implant for electrical stimulation of a sphenopalatine ganglion (SPG) of a subject. Stimulation of the SPG typically treats various acute brain hypoperfusion states, such as occur during acute ischemic stroke. Typically, the system includes apparatus comprising an implantable neural stimulator, a steerable delivery guide, and an oral surgical guide.

The neural stimulator implant is configured to be passed through a greater palatine foramen of a palate of an oral cavity of a subject into a greater palatine canal, such that the neural stimulator implant is brought into a vicinity of a sphenopalatine ganglion (SPG), for example, into contact with the SPG. For some applications, the implant is a flexible implant configured to conform to the anatomical structure of the greater palatine canal, to facilitate advancement therethrough. For some applications, the implant comprises at least one electrode for stimulation of the SPG.

The neural stimulator implant is typically coupled to the steerable delivery guide. For some applications, a distal end of the steerable delivery guide is configured to puncture oral mucosa of the subject, allowing the neural stimulator implant to be passed through the palate in a minimally-invasive procedure, without requiring a prior surgical incision in the mucosa. Typically, the distal end of the steerable delivery guide is also configured to be passed through the greater palatine foramen into the greater palatine canal. The delivery guide is steered in the canal in order to deliver the neural stimulator implant to the SPG.

Typically, the surgical guide is generated based on CT data obtained by imaging the subject. Based on the CT data, the surgical guide is formed to provide a guide hole for locating the entrance to the greater palatine canal, such that the implantable neural stimulator may be passed through the guide hole and then into the greater palatine canal. In particular, the surgical guide is typically configured for placement on the subject's dental arch, such that an extension portion of the surgical guide extending away from the dental arch contacts the roof of the oral cavity of the subject, and the guide hole is thereby automatically placed over the entrance to the greater palatine foramen of the subject.

For some applications, the surgical guide is generated based on data from both a CT scan and an intra-oral scan. For such applications, an intra-oral scan of the upper palate, teeth, and/or gums of the subject is performed in addition to the CT scan, and the data from both scans are registered for preparation of the surgical guide. Alternatively, the surgical guide is initially generated based on data from an intra-oral scan only, and subsequently CT data are used for preparing the guide hole in the surgical guide.

Thus, in accordance with some applications of the present invention, the surgical guide is configured to guide an operating physician to the location of the greater palatine foramen of the subject, to facilitate advancement of the neural stimulator implant therethrough by injecting the implant into the canal. Additionally, the guide hole in the surgical guide facilitates penetration of the mucosa at an appropriate angle for entrance into the greater palatine foramen at an angle suitable for advancement of the neural stimulator implant through the canal. Further additionally, the CT data in combination with the surgical guide provides the operating physician with information regarding the anatomical structure of the greater palatine canal, thereby facilitating navigation and advancement of the implantable neural stimulator coupled to the steerable delivery guide through the canal. Thus, in accordance with some applications, the surgical guide in combination with the CT data, guides the passing through oral mucosa of the subject and navigation of the neural stimulator implant within a complex anatomical structure. Additionally, but not necessarily, the surgical guide provides guidance for drilling at a predetermined depth into the jaw bone.

The surgical guide typically allows for use of the neural stimulator implant by facilitating precise and safe implant deployment at the SPG, even by a less-skilled surgeon. Similarly, in general, the surgical guide allows a less-skilled surgeon to access the SPG in a safe and precise manner (even in the absence of implanting a neural stimulator implant).

For some applications, the delivery guide is configured to facilitate delivery of the neural stimulator to the SPG site without the need for the physician to consider a navigation map of the greater palatine canal. For some such applications, CT data regarding the anatomical structure of the greater palatine canal is used to create (typically by 3D printing) a curved guide groove surface on a portion of the delivery guide. When the neural stimulator is mounted on a distal end of the delivery guide, it is advanced distally in the canal by advancement of a slide-bar of the delivery guide. At the same time, a guiding pin which is disposed within the curved guide groove is advanced within the groove, causing rotation of the slide-bar with respect to the delivery guide, thereby steering the neural stimulator in the greater palatine canal.

For some applications, a shape-sensing optical fiber optically couplable to an optical fiber shape-sensing system is provided. The shape-sensing optical fiber typically is advanced by a delivery tool, e.g., a trocar, through the palatine canal and a shape of the canal is assessed using the shape-sensing optical fiber. The shape-sensing optical fiber is then removed from the canal. Subsequently, the neural stimulator implant is advanced and navigated through the palatine canal based on the assessing of the shape of the canal by the shape-sensing optical fiber.

For other applications, the neural stimulator implant additionally comprises the shape-sensing optical fiber optically couplable to an optical fiber shape-sensing system. The shape-sensing optical fiber is configured to change shape during delivery of the implant to the SPG through the greater palatine canal, to facilitate advancement and navigation of the implant through the canal.

There is therefore provided, in accordance with an application of the present invention, apparatus, including:

an oral surgical guide including:
an arch portion configured to be placed on a dental arch of a subject; and
an extension portion extending from the arch portion, and shaped to define a guide hole.

For some applications, the extension portion extends from the arch portion in a superior and lingual direction with respect to the arch.

For some applications, the apparatus includes:
a steerable implantable neural stimulator configured to apply electrical stimulation to a sphenopalatine ganglion (SPG) of the subject,
the guide hole is configured to guide the stimulator through a greater palatine foramen of a palate of an oral cavity of the subject and into a greater palatine canal of the subject.

For some applications, the guide hole is configured to guide the stimulator through the greater palatine foramen at an angle that is suitable for entering the greater palatine canal.

For some applications, the surgical guide is generated by using CT scan data of the subject and intra-oral scan data of the subject, and the guide hole corresponds to a location of a greater palatine foramen of the subject.

For some applications, a portion of the surgical guide corresponding to a surface of gum tissue of the subject is shaped in a curved manner that matches curvature of the gum tissue.

For some applications, the surgical guide is generated by using CT scan data of the subject and not using intra-oral scan data of the subject, and the guide hole corresponds to a location of a greater palatine foramen of the subject.

For some applications, the implant is shaped to define proximal and distal portions, and the distal portion of the implant is configured to puncture oral mucosa of the subject.

For some applications, the implant is shaped to define proximal and distal portions, and the distal portion of the implant includes at least one electrode configured to apply electrical stimulation to a sphenopalatine ganglion (SPG) of the subject.

For some applications, the surgical guide is formed by a three-dimensional printing process.

For some applications, the surgical guide is shaped by shaping a pliable material on the dental arch of the subject.

For some applications, the pliable material includes a thermoplastic material.

There is further provided, in accordance with an application of the present invention, a method including:

using an oral surgical guide generated using CT data to determine a location of a greater palatine foramen of a palate of an oral cavity of a subject;
inserting a steerable implantable neural stimulator into the greater palatine foramen of the subject, through a hole in the surgical guide; and advancing the stimulator through a greater palatine canal of the subject to a sphenopalatine ganglion (SPG) of the subject.

For some applications, using the oral surgical guide generated using CT data further includes using the oral surgical guide to determine a suitable angle for entering of the greater palatine canal, and inserting the stimulator into the greater palatine foramen includes inserting the stimulator at the suitable angle.

For some applications, the method includes creating an opening in mucosa of the subject using the stimulator, and inserting the stimulator includes stimulator through the opening.

For some applications, the method includes coupling a tool, in which the stimulator is disposed, to the hole in the surgical guide, and creating the opening includes creating the opening while the tool is coupled to the hole in the surgical guide.

For some applications, inserting the stimulator includes inserting the stimulator using a tool, and the method further includes, following the advancing of the stimulator, allowing the tool to be withdrawn from the greater palatine canal without dislodging the stimulator by disengaging a locking element of the stimulator from the tool.

For some applications, the locking element is shaped as a ball, and disengaging the locking element includes disengaging the ball-shaped locking element from the tool.

There is further provided, in accordance with an application of the present invention, apparatus for use with a tool, the apparatus including:
 an oral surgical guide including:
  an arch portion configured to be placed on a dental arch of a subject; and
  an extension portion from the arch portion, and shaped to define (a) a guide hole, and (b) a protruding portion including a first coupling element configured to lockingly couple to the tool.

For some applications, the protruding portion is shaped to define a screw thread.

There is further provided, in accordance with an application of the present invention, a method including:
 using a processor, receiving CT data of an oral cavity of a subject acquired while (a) a surgical guide and (b) one or more markers, were in the oral cavity;
 using the processor, identifying a position of one or more markers on a drill with respect to respective sites on the surgical guide corresponding to the markers in the oral cavity; and
 using the processor and the identified position, guiding drilling of a hole in the surgical guide, by the drill, at a site on the surgical guide corresponding to a greater palatine foramen of the subject.

For some applications, the one or more markers are on the surgical guide, and receiving the CT data using the processor includes receiving the CT data using the processor, the CT data having been acquired while the surgical guide having the one or more markers thereon was in the oral cavity.

For some applications, the one or more markers in the oral cavity are one or more teeth of the subject.

For some applications, the surgical guide includes a thermoplastic material and guiding drilling of a hole in the surgical guide includes drilling a hole in the thermoplastic material.

There is further provided, in accordance with an application of the present invention, a method, including:
 providing a flexible, elongate implant having electrodes thereon and an unconstrained shape having a bend at least at a distal end portion of the implant;
 subsequently, advancing the implant through a greater palatine canal of a subject; and
 utilizing the bend at the distal end portion of the implant to facilitate steering of the implant during the advancing of the implant.

For some applications, the implant includes a nitinol portion which provides the bend, and providing the implant includes providing the implant having the nitinol portion.

For some applications, the method includes, following the advancing of the implant, leaving the implant in the greater palatine canal of the subject while the distal end portion of the implant is constrained and not bent as it was prior to the advancing of the implant.

There is further provided, in accordance with an application of the present invention, apparatus, including:
 a flexible, elongate implant, the implant having an unconstrained shape having a bend at least at a distal end portion of the implant, the implant including:
  two or more electrodes;
  a flexible portion disposed at least between the two electrodes; and
  a receiving coil configured to receive energy for powering driving of the electrodes.

There is further provided, in accordance with an application of the present invention, apparatus including:
 an elongated implantable neural stimulator having proximal and distal sites and configured to apply electrical stimulation to a sphenopalatine ganglion (SPG) of a subject; and
 electronic circuitry having first and second portions and coupled respectively to the proximal and distal sites of the implantable neural stimulator, the electronic circuitry in the first portion being flexibly coupled to the electronic circuitry in the second portion.

For some applications, the apparatus includes a flexible connecting element coupled to the first and second portions of the electronic circuitry.

There is further provided, in accordance with an application of the present invention, apparatus for delivery of an implantable neural stimulator to a sphenopalatine ganglion (SPG) of a subject, including:
 a tool having a distal portion coupled to the implantable neural stimulator and a proximal portion; and
 a slide-bar at the proximal portion of the tool, the slide-bar including a distal portion and a proximal portion, the proximal portion of the slide-bar being coupled to the stimulator such that distal advancement of the proximal portion of the slide-bar produces distal advancement of the stimulator, the proximal and distal portions of the slide-bar each including a respective magnetic element, the magnetic elements being configured to couple the proximal and distal portions of the slide-bar to each other unless a distally-directed force applied to the distal portion of the slide-bar exceeds a threshold.

There is yet further provided, in accordance with an application of the present invention, a method including:
 using an oral surgical guide generated using scan data selected from the group consisting of: intra-oral scan data and CT scan data, to determine a location of a greater palatine foramen of a palate of an oral cavity of a subject;
 inserting a steerable implantable neural stimulator into the greater palatine foramen of the subject, through a hole in the surgical guide; and
 advancing the stimulator through a greater palatine canal of the subject to a sphenopalatine ganglion (SPG) of the subject.

For some applications, using scan data selected from the group consisting of intra-oral scan data and CT scan data, includes using CT scan data and not intra-oral scan data.

For some applications, using scan data selected from the group consisting of intra-oral scan data and CT scan data, includes using intra-oral scan data and not CT scan data.

For some applications, using scan data selected from the group consisting of intra-oral scan data and CT scan data, includes using intra-oral scan data and CT scan data.

For some applications, using the oral surgical guide generated using the scan data includes using the oral surgical guide generated using the CT scan data, and using the oral surgical guide generated using the CT scan data further includes using the oral surgical guide to determine a suitable angle for entering of the greater palatine canal, and inserting the stimulator into the greater palatine foramen includes inserting the stimulator at the suitable angle.

For some applications, the method includes creating an opening in mucosa of the subject using the stimulator, inserting the stimulator includes inserting the stimulator through the opening.

For some applications, the method includes coupling a tool, in which the stimulator is disposed, to the hole in the surgical guide, and creating the opening includes creating the opening while the tool is coupled to the hole in the surgical guide.

For some applications, inserting the stimulator includes inserting the stimulator using a tool, and the method further includes, following the advancing of the stimulator, allowing the tool to be withdrawn from the greater palatine canal without dislodging the stimulator by disengaging a locking element of the stimulator from the tool.

For some applications, the locking element is shaped as a ball, and disengaging the locking element includes disengaging the ball-shaped locking element from the tool.

There is yet further provided, in accordance with an application of the present invention, a method including:

receiving CT scan data and intra-oral scan data of a subject; and using the CT and intra-oral scan data, generating an oral surgical guide shaped to define a hole, the hole being placeable against a location of a greater palatine foramen of the subject.

For some applications, generating the oral surgical guide includes:

generating the oral surgical guide without the hole, using the intra-oral scan data;

subsequently, performing the step of receiving the CT scan data; and subsequently, generating the oral surgical guide with the hole by creating the hole using the CT scan data.

There is yet further provided, in accordance with an application of the present invention, apparatus for delivery of an implant to an anatomical site of a subject, the apparatus including:

a delivery tool having a proximal portion, and having a distal portion that is coupled to the implant;

a surface at the proximal portion, the surface shaped to define a curved guide groove based on data obtained by imaging the anatomical site of the subject;

a slide-bar slidably coupled to the proximal portion; and a guiding pin disposed within the curved guide groove and configured such that distal advancement of the slide-bar with respect to the proximal portion produces (1) relative motion of the guiding pin with respect to the curved guide groove, and (2) rotation of the slide-bar with respect to a longitudinal axis of the delivery tool.

For some applications, the surface shaped to define the curved guide groove is a surface of the delivery tool, and the guiding pin is fixedly coupled to the slide-bar.

For some applications, the surface shaped to define the curved guide groove is a surface of the slide-bar, and the guiding pin is fixedly coupled to the delivery tool.

There is still provided, in accordance with an application of the present invention, a system including:

a CT scanning device configured to image a subject;

an intra-oral scanning device configured to image the subject; and a three-dimensional printing device configured to generate, based on the CT and intra-oral scanning of the subject, a surgical guide that is shaped to define a guide hole for locating a greater palatine foramen of a palate of an oral cavity of the subject.

There is further provided, in accordance with an application of the present invention, apparatus for use with an optical fiber shape-sensing system, the apparatus including:

an implant including (a) a neural stimulator configured to apply electrical stimulation to a sphenopalatine ganglion (SPG) of a subject, and (b) an optical fiber fixed to the neural stimulator, optically couplable to the optical fiber shape-sensing system, and configured to change shape during delivery of the implant to the SPG through a greater palatine canal of the subject; and a delivery tool configured (a) to be removably coupled to the implant, (b) to deliver the implant to the SPG through the greater palatine canal, and (c) to detach from the implant once the implant is delivered to the SPG.

For some applications, the optical fiber shape-sensing system includes optical fiber shape-sensing circuitry and the optical fiber is optically couplable to the optical fiber shape-sensing circuitry.

For some applications, the delivery tool includes a detachment mechanism configured to detach the delivery tool from the implant.

For some applications, the detachment mechanism includes a cutting tool, and the cutting tool is configured to cut the optical fiber.

For some applications, the detachment mechanism includes a cutting tool, and the detachment mechanism is configured to detach the delivery tool from the implant by cutting the optical fiber.

For some applications, a portion of the optical fiber (a) is disposed in the delivery tool, and (b) is shaped within the delivery tool such that relative motion between the implant and the delivery tool causes a change in the shape of the portion of the optical fiber.

For some applications, the portion of the optical fiber in the delivery tool is shaped to define a loop, such that distancing of the delivery tool from the implant causes a reduction in a diameter of the loop.

For some applications, the portion of the optical fiber in the delivery tool is shaped to define a curve, such that distancing of the delivery tool from the implant causes a straightening of the curve.

For some applications the apparatus further includes, a proximity sensor configured to indicate that the delivery tool is detached from the implant by generating a signal that varies in response to relative motion between the delivery tool and the implant.

For some applications, the proximity sensor includes at least one radiofrequency (RF) coil coupled to the implant and at least one RF coil coupled to the delivery tool.

For some applications, the proximity sensor includes at least one magnetic element coupled to the implant and at least one magnetic element coupled to the delivery tool.

For some applications, the neural stimulator has a proximal portion, a distal portion and a middle portion between the proximal and distal portions, and the proximal portion is more rigid than the middle portion.

For some applications, the distal portion is more rigid than the middle portion.

There is further provided in accordance with an application of the present invention, a method including:

using a delivery tool, distally advancing, through a greater palatine canal of a subject, an optical fiber and a neural stimulator that is configured to apply electrical stimulation to a sphenopalatine ganglion (SPG) of the subject, the optical fiber being configured to change shape during advancement of the neural stimulator through the greater palatine canal; and assessing a shape of the palatine canal using an optical fiber shape-sensing system, based on a shape of the optical fiber during advancement.

For some applications, the optical fiber is coupled to the neural stimulator, and distally advancing includes distally advancing the optical fiber coupled to the neural stimulator.

For some applications, the optical fiber is coupled to the delivery tool, and distally advancing includes distally advancing the optical fiber coupled to the delivery tool.

For some applications, the optical fiber contacts the neural stimulator during the step of distal advancing using the delivery tool.

For some applications, the optical fiber is wrapped around a portion of the neural stimulator during the step of distal advancing using the delivery tool.

For some applications, the method includes:

deploying the neural stimulator in a vicinity of the SPG; and decoupling the optical fiber from the neural stimulator by pulling a proximal end of the optical fiber, while maintaining the neural stimulator in the vicinity of the SPG using a pusher.

For some applications, the optical fiber shape-sensing system includes optical fiber shape-sensing circuitry and assessing includes assessing a shape of the palatine canal using the optical fiber shape-sensing circuitry.

For some applications, assessing further includes assessing an orientation of the neural stimulator within the greater palatine canal using the optical fiber shape-sensing system, based on a shape of the optical fiber during advancement.

For some applications, assessing further includes assessing a location of the neural stimulator within the greater palatine canal using the optical fiber shape-sensing system, based on a shape of the optical fiber during advancement.

For some applications, the method further includes navigating the neural stimulator in the palatine canal based on the assessing of the shape of the palatine canal.

There is additionally provided in accordance with an application of the present invention apparatus for use with an optical fiber shape-sensing system, the apparatus including:

an implant including (a) a neural stimulator configured to apply electrical stimulation to a sphenopalatine ganglion (SPG) of a subject, and (b) an optical fiber in contact with the neural stimulator, and optically couplable to the optical fiber shape-sensing system, and configured to change shape during delivery of the implant to the SPG through a greater palatine canal of the subject; and a delivery tool configured (a) to be removably coupled to the implant, (b) to deliver the implant to the SPG through the greater palatine canal, and (c) to detach from the implant once the implant is delivered to the SPG.

For some applications, a portion of the optical fiber is wrapped around a portion of the neural stimulator.

For some applications, the optical fiber is configured to be decoupled from the neural stimulator by pulling a proximal end of the optical fiber.

For some applications, the neural stimulator has a proximal portion, a distal portion and a middle portion between the proximal and distal portions, and the proximal portion is more rigid than the middle portion.

For some applications, the distal portion is more rigid than the middle portion.

For some applications, a portion of the optical fiber (a) is disposed in the delivery tool, and (b) is shaped within the delivery tool such that relative motion between the implant and the delivery tool causes a change in the shape of the portion of the optical fiber.

For some applications, the portion of the optical fiber in the delivery tool is shaped to define a loop, such that distancing of the delivery tool from the implant causes a reduction in a diameter of the loop.

For some applications, the portion of the optical fiber in the delivery tool is shaped to define a curve, such that distancing of the delivery tool from the implant causes a straightening of the curve.

For some applications the apparatus further includes a proximity sensor configured to indicate that the delivery tool is detached from the implant by generating a signal that varies in response to relative motion between the delivery tool and the implant.

For some applications the proximity sensor includes at least one radiofrequency (RF) coil coupled to the implant and at least one RF coil coupled to the delivery tool.

For some applications the proximity sensor includes at least one magnetic element coupled to the implant and at least one magnetic element coupled to the delivery tool.

There is further provided in accordance with an application of the present invention, a method including:

using an optical fiber shape-sensing system, assessing a travel path of a neural stimulator advanced in a greater palatine canal toward a sphenopalatine ganglion (SPG) of a subject, based on shape changes of an optical fiber advanced toward the SPG along with the neural stimulator;

using a navigation system, assessing a travel path of the neural stimulator in the canal based on movement of an optical marker attached to a delivery tool used for advancing the neural stimulator;

generating an indication that there is an error in the travel path assessed using the navigation system if (a) the travel path detected using the optical fiber shape-sensing system matches a pre-operatively determined shape of the canal and (b) the travel path assessed using the navigation system indicates that the neural stimulator has passed out of the canal.

For some applications, the method further includes the step of recalibrating the navigation system by performing registration of the optical marker, following generating the indication that there is an error in the travel path.

There is further provided in accordance with an application of the present invention, a method including:

using an optical fiber shape-sensing system, assessing a travel path of a neural stimulator in a greater palatine canal advanced toward a sphenopalatine ganglion (SPG) of a subject, based on shape changes of an optical fiber advanced toward the SPG along with the neural stimulator;

using a navigation system, assessing a travel path of the neural stimulator in the canal based on movement of an optical marker attached to a delivery tool used for advancing the neural stimulator;

generating an indication that there is an error in the travel path assessed using at least one of the systems if (a) the travel path assessed using the navigation system matches pre-operative registration data of the optical marker, and (b) the travel path detected using the optical fiber shape-sensing system indicates that the neural stimulator has passed out of the canal; and recalibrating the navigation system by performing registration of the optical marker.

There is further provided in accordance with an application of the present invention, a method including:

advancing an optical fiber through a bony canal of a subject, the optical fiber (a) being configured to change shape during advancement through the bony canal and (b) being optically coupled to optical fiber shape-sensing system;

using the optical fiber shape-sensing system, assessing a shape of the optical fiber during advancement through the bony canal; and assessing a shape of the bony canal based on the assessing of the shape of the optical fiber.

There is further provided in accordance with an application of the present invention, apparatus including:

an implant including a neural stimulator configured to apply electrical stimulation to a sphenopalatine ganglion (SPG) of a subject, the implant having a maximum length of 4 cm and a maximum diameter of 3 mm;

a delivery tool configured (a) to be removably coupled to the implant, (b) to deliver the implant to the SPG through a greater palatine canal, and (c) to detach from the implant once the implant is delivered to the SPG; and a proximity sensor configured to indicate that the delivery tool is detached from the implant by generating a signal in response to relative motion between the delivery tool and the implant.

There is further provided in accordance with an application of the present invention, apparatus including:

an oral surgical guide having a non-patient-customized portion and a patient-customized portion, the oral surgical guide including:

an arch portion configured to be placed on a dental arch of a subject; and an extension portion extending from the arch portion, and shaped to define a guide hole.

There is further provided in accordance with an application of the present invention, a method including:

using an oral surgical guide generated using CT data to determine a location of a greater palatine foramen of a palate of an oral cavity of a subject;

inserting a steerable implantable neural stimulator mounted on a delivery guide into the greater palatine foramen of the subject, through a hole in the surgical guide;

advancing the stimulator through a greater palatine canal of the subject to a sphenopalatine ganglion (SPG) of the subject; and terminating the advancing of the stimulator based on contact of a portion of the delivery guide with a portion of the surgical guide that has a length corresponding to a location of the SPG.

There is further provided in accordance with an application of the present invention, apparatus for use with an optical fiber shape-sensing system, the apparatus including:

an optical fiber, optically couplable to the optical fiber shape-sensing system, and configured to change shape during advancement through a greater palatine canal of a subject;

a delivery tool configured to be removably coupled to the optical fiber and to distally advance the optical fiber through the greater palatine canal; and a neural stimulator implant, configured to apply electrical stimulation to a sphenopalatine ganglion (SPG) of the subject, and (i) not in contact with the optical fiber, and (ii) shaped and sized to be delivered to the sphenopalatine ganglion (SPG) by the delivery tool.

For some applications, the neural stimulator implant is not disposed within the delivery tool.

For some applications, the optical fiber has a sensing length of 4-6 cm.

For some applications, the optical fiber has fiber Bragg gratings that are positioned 2-5 mm apart from each other.

For some applications, the optical fiber shape-sensing system includes optical fiber shape-sensing circuitry and the optical fiber is optically couplable to the optical fiber shape-sensing circuitry.

For some applications, the apparatus further includes a proximity sensor configured to indicate that the delivery tool is detached from the implant by generating a signal that varies in response to relative motion between the delivery tool and the implant.

For some applications, the neural stimulator has a proximal portion, a distal portion and a middle portion between the proximal and distal portions, and the proximal portion is more rigid than the middle portion.

For some applications, the distal portion is more rigid than the middle portion.

There is further provided in accordance with an application of the present invention, a method including:

using a delivery tool, distally advancing, through a greater palatine canal of a subject, an optical fiber being configured to change shape during advancement through the greater palatine canal;

assessing a shape of the palatine canal using an optical fiber shape-sensing system, based on a shape of the optical fiber during advancement;

removing the optical fiber from the greater palatine canal; and subsequently to removing the optical fiber, distally advancing through the greater palatine canal a neural stimulator that is configured to apply electrical stimulation to a sphenopalatine ganglion (SPG) of the subject.

For some applications, distally advancing the neural stimulator includes navigating the neural stimulator in the palatine canal based on the assessing of the shape of the palatine canal.

For some applications, using the delivery tool includes navigating the delivery tool in the palatine canal based on the assessing of the shape of the palatine canal.

For some applications, assessing the shape of the palatine canal using the optical fiber shape-sensing system, includes mapping the palatine canal based on a shape of the optical fiber during advancement.

For some applications, the method further includes implanting the neural stimulator in a vicinity of the SPG.

For some applications, the optical fiber shape-sensing system includes optical fiber shape-sensing circuitry and wherein assessing includes assessing a shape of the palatine canal using the optical fiber shape-sensing circuitry.

For some applications the method further includes, using the delivery tool during the distal advancing thereof, widening the palatine canal in preparation for advancing of the neural stimulator.

There is further provided in accordance with an application of the present invention, a method including:

using a delivery tool, advancing an optical fiber through a bony canal of a subject, the optical fiber (i) being configured to change shape during advancement through the bony canal and (ii) being optically coupled to optical fiber shape-sensing system;

using the optical fiber shape-sensing system, assessing a shape of the optical fiber during advancement through the bony canal;

assessing a shape of the bony canal based on the assessing of the shape of the optical fiber;

removing the optical fiber from the bony canal; and subsequently to the removing, navigating an implant through the bony canal.

For some applications, navigating the implant includes navigating the implant in the bony canal based on the assessing of the shape of the bony canal.

There is further provided in accordance with an application of the present invention apparatus for use with an optical fiber shape-sensing system, the apparatus including:

an optical fiber, (i) optically couplable to the optical fiber shape-sensing system, (ii) configured to change shape during advancement through a greater palatine canal of the subject, and (iii) shaped to define a predetermined breaking point of the optical fiber between a distal portion of the optical fiber and a proximal portion of the optical fiber, such that application of force to the predetermined breaking point causes breaking of the optical fiber at the predetermined breaking point;

a delivery tool configured (a) to be removably coupled to the optical fiber, and (b) to distally advance the optical fiber through the greater palatine canal of the subject.

For some applications, the optical fiber is shaped to define a narrow portion which defines the predetermined breaking point.

For some applications, the apparatus further includes a sheath, and the predetermined breaking point is disposed in the sheath.

For some applications, a length of the sheath is 2 mm-15 mm.

For some applications, the apparatus further includes a neural stimulator fixed to the optical fiber and configured to apply electrical stimulation to a sphenopalatine ganglion (SPG) of a subject.

There is further provided in accordance with an application of the present invention, a method including:

using a delivery tool, distally advancing, through a greater palatine canal of a subject, an optical fiber, the optical fiber being configured to change shape during advancement of the neural stimulator through the greater palatine canal;

assessing a shape of the palatine canal using an optical fiber shape-sensing system, based on a shape of the optical fiber during advancement;

separating a distal portion of the optical fiber from a proximal portion of the optical fiber by applying force to a predetermined breaking point in the optical fiber; and removing the proximal portion of the optical fiber from the palatine canal.

For some applications, a portion of the optical fiber including the predetermined breaking point is disposed within a sheath during the applying of the force to the predetermined breaking point.

There is further provided in accordance with an application of the present invention apparatus, including:

an oral surgical guide including:
an arch portion configured to be placed on a dental arch of a subject;
an extension portion extending from the arch portion in a superior and lingual direction with respect to the arch, and shaped to define a guide hole; and
a support element extending from a left side of the arch portion to a right side of the arch portion, posterior to a canine region of the oral surgical guide.

The present invention will be more fully understood from the following detailed description of embodiments thereof, taken together with the drawings, in which:

BRIEF DESCRIPTION OF THE DRAWINGS

FIGS. 4A, 4B, 4C, and 4D are schematic illustrations of the system for delivery of a neural stimulator implant for electrical stimulation of a sphenopalatine ganglion (SPG) of a subject, in accordance with some applications of the present invention;

FIGS. 9A and 9B are schematic illustrations of the neural stimulator implant, in accordance with some applications of the present invention;

FIG. 10 is a schematic illustration of the neural stimulator implant, in accordance with some applications of the present invention;

FIGS. 12A, 12B and 12C are schematic illustrations of a tool comprising a guiding groove for facilitating delivery of a neural stimulator implant for electrical stimulation of a sphenopalatine ganglion (SPG) of a subject, in accordance with some applications of the present invention;

FIG. 13 is a block diagram showing steps for preparation of a surgical guide, in accordance with some applications of the present invention;

FIGS. 14A and 14B are schematic illustrations of a neural stimulator implant and an optical fiber, mounted onto a delivery tool for facilitating delivery of the implant, for electrical stimulation of a sphenopalatine ganglion (SPG) of a subject, in accordance with some applications of the present invention;

FIGS. 15A, 15B, 16 and 17 are schematic illustrations of a neural stimulator implant and an optical fiber, in accordance with some applications of the present invention;

DETAILED DESCRIPTION OF APPLICATIONS

Figure 1:
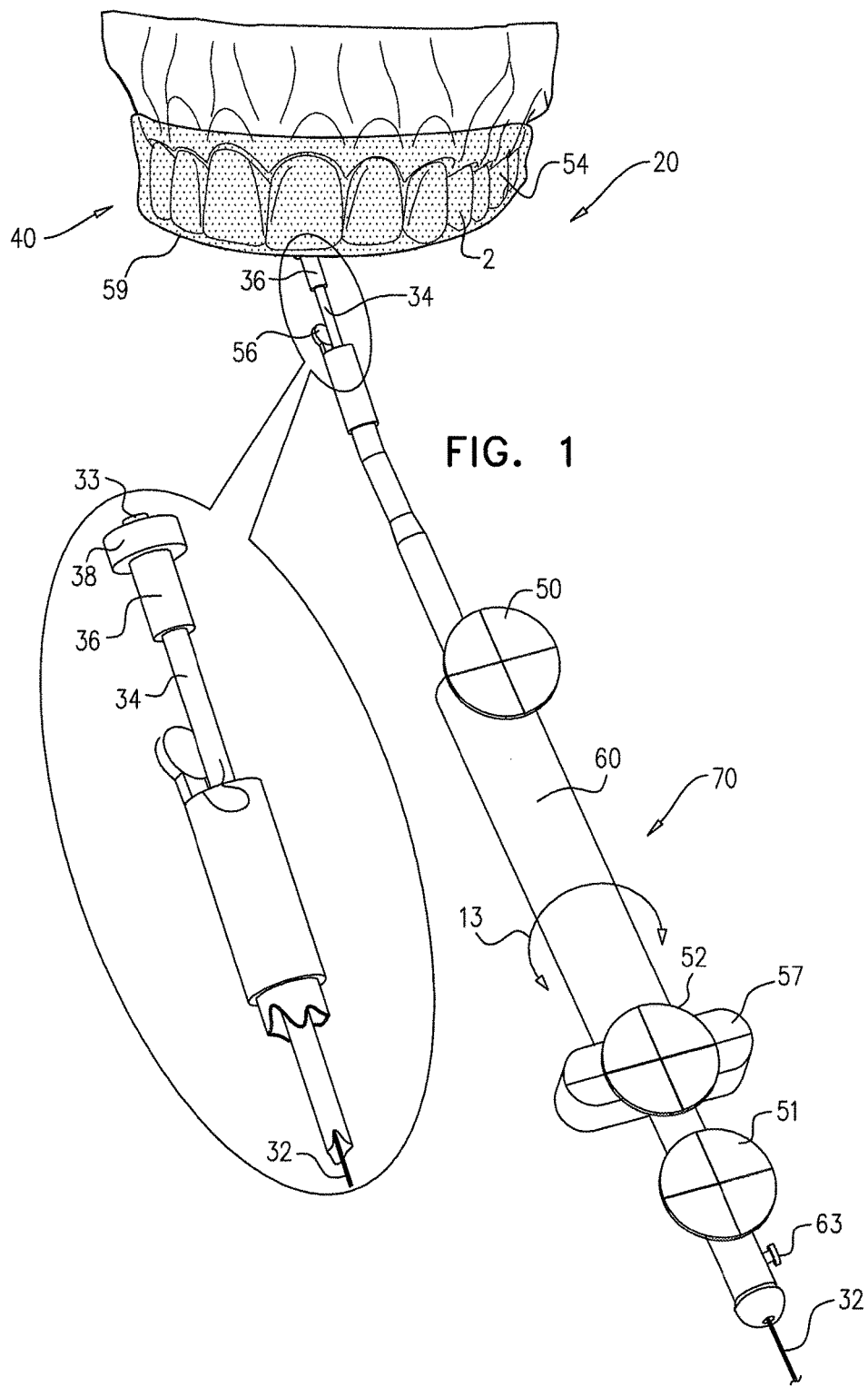
FIG. 1 shows a system for delivery of a neural stimulator implant for electrical stimulation of a sphenopalatine ganglion (SPG) of a subject, in accordance with some applications of the present invention.

Reference is made to FIG. 1, which is a schematic illustration of a system 20 for delivery of a neural stimulator implant 32 for electrical stimulation of a sphenopalatine ganglion (SPG) of a subject, in accordance with some applications of the present invention. Typically, system 20 includes neural stimulator implant 32, steerable delivery guide 34, and an oral surgical guide 40.

Typically, neural stimulator implant 32 is configured to be passed through a greater palatine foramen of the hard palate of the oral cavity of the subject, into a greater palatine canal, such that the neural stimulator implant is brought into a vicinity of a sphenopalatine ganglion (SPG). For some applications, the implant is an elongated, flexible implant having an unconstrained shape and configured to conform to the anatomical structure of the greater palatine canal, for advancement therethrough. For some applications, the implant comprises at least one electrode, e.g., a wire electrode, for stimulation of the SPG. Typically, implant 32 is shaped to define a curved or bent distal end, which facilitates steering of the implant during the advancing of the implant in the canal. (For the purposes of the specification and claims of the present patent application, the terms "curved" or "bent" with respect to the distal end of the implant are to be understood as interchangeable.) Typically, following the advancing of the implant and deployment thereof in the vicinity of the SPG, for some subjects, the distal end of the implant is constrained and substantially not curved due to the anatomy of the canal, which is generally straight in the vicinity of the SPG in these subjects. For other subjects, the canal is curved in the vicinity of the SPG, and thus the distal end of the implant is curved at its implantation site in the vicinity of the SPG.

For some applications, neural stimulator implant 32 is coupled to steerable delivery guide 34. Implant 32 is configured to be passed through guide 34, such that both implant 32 and guide 34 are advanced through the greater palatine foramen into the greater palatine canal, and implant 32 is brought into a vicinity of a sphenopalatine ganglion (SPG). Steerable delivery guide 34 is retracted after placement of implant 32.

FIG. 1 shows an exploded view of neural stimulator implant 32 passed through delivery guide 34. Delivery guide 34 is typically less flexible than neural stimulator implant 32, and thereby facilitates smooth passage of the implant through the greater palatine canal and proper delivery of implant 32 to the SPG.

For some applications, a distal end 33 of steerable delivery guide 34 is configured to puncture oral mucosa of the subject, allowing neural stimulator implant 32 to be passed through the palate in a minimally-invasive procedure, without requiring a prior surgical incision in the mucosa. Typically, the distal end of the steerable delivery guide is also configured to be passed through the greater palatine foramen into the greater palatine canal. The delivery guide is steered in the canal in order to deliver the neural stimulator implant to the SPG. For some applications, neural stimulator implant 32 is configured to puncture or otherwise create an opening in the oral mucosa of the subject. Following insertion of implant 32 into the mucosa, the surgeon may optionally seal the puncture site by applying pressure to the puncture site in order to facilitate self-healing of the hole, e.g., by keeping a finger on the puncture site.

FIG. 1 additionally shows surgical guide 40 (represented by the dotted structure) placed on teeth 2 of a dental arch 54 of the subject. (It is to be understood that for subjects without teeth, guide 40 is placed on the gums.) Surgical guide 40 is generated based on CT data of the subject and typically serves as a guide for locating the entrance to the greater palatine canal through the greater palatine foramen of the hard palate. Surgical guide 40 comprises an arch portion 59 configured for placement on dental arch 54, and an extension portion 58 (shown in FIGS. 2-3) that extends away from the arch portion. The extension portion is shaped to define a guide hole 6 (shown in FIGS. 2-3), which provides an operating physician with the location and preferred entry angle to the greater palatine foramen. Typically the location and angle of the entrance to the canal, as well as the length of the canal, varies among the population. Therefore, surgical guide 40 allows safe and accurate entry into the canal, and navigation therethrough, in accordance with the subject's anatomy, based on the CT data. Surgical guide 40 additionally inhibits excessive insertion of implant 32 into the canal.

For some applications, a distal end 38 of an angular guide 36 is placed on extension portion 58 of surgical guide 40 to facilitate advancement of delivery guide 34 through guide hole 6 in surgical guide 40. Typically, distal end 38 plugs into hole 6, such that angular guide 36 facilitates advancement of delivery guide 34 into hole 6 at the preferred angle, based on the CT data. When angular guide 36 is locked properly in place with respect to surgical guide 40, delivery guide 34 is released by turning knob 63 in order to allow advancement of guide 34 through guide hole 6. A tool 70 is configured to direct advancement of guide 34 through guide hole 6 and subsequently through the greater palatine foramen into the greater palatine canal. Handle 60 of tool 70 is steered and/or advanced, in order to direct motion of steerable delivery guide 34.

Typically, the passage of implant 32 and delivery guide 34 into the greater palatine canal is facilitated by image-guided surgical techniques, e.g., using optical fiducial markers 50, 51 and 52 on tool 70 (and/or fiducial markers on guide 34). For some applications, an image-guided surgery processor utilizes location data derived from markers 50, 51 and 52, in combination with fiducial markers on the subject (e.g., placed on the teeth, face or a head of the subject) in order to register the pre-operative CT data with the current position of the tool and thereby facilitate steering and advancement of steerable delivery guide 34 through the greater palatine canal. Alternatively or additionally, the image-guided surgery processor utilizes location data derived from markers 50, 51 and 52 in combination with registration data obtained by (a) contacting a tool with a fiducial marker to multiple spots on the subject's head that can also be identified in the pre-operative CT image, and/or (b) visualizing markers 50, 51, and/or 52 when angular guide 36 is locked in place, for example, by plugging distal end 38 into guide hole 6 or by a locking mechanism (as described herein below with reference to FIGS. 4A-C). For some applications, handle 60 comprises a linear and/or an angular encoder configured to facilitate recording of location data indicative of the current position and orientation of neural stimulator implant 32. It is noted that the fiducial markers described herein can be used both in order to identify locations in the subject's anatomy, and also as a reference marker, in order to continually allow the image-guided surgery processor to identify a current position of the subject's head, which can move.

Additionally, slide-bar 57 on tool 70 facilitates advancement of delivery guide 34 distally through guide hole 6. Typically, slide-bar 57 provides steering functionality for facilitating advancement of guide 34 into the greater palatine canal. Bar 57 is typically slidable with respect to handle 60. Advancement of slide-bar 57 with respect to handle 60 advances delivery guide 34 through the greater palatine canal. Additionally or alternatively, marker 50 comprises steering functionality and is rotated around a center thereof in order to steer guide 34 and neural stimulator implant 32 within the canal in order to deliver the neural stimulator implant to the SPG. Further additionally or alternatively, handle 60 is rotated as indicated by arrow 13, in order to advance and orientate steerable delivery guide 34 within the greater palatine canal.

For some applications, additional steering options are employed to allow control of the advancement of implant 32 within the canal. For example, using a joystick allows steering the implant in a left/right and up/down direction, as well as rotation around an axis.

Typically, the greater palatine canal is curved and multiple openings are naturally formed along the greater palatine canal. Therefore, proper steering of guide 34 within the canal generally ensures delivery of guide 34 and neural stimulator implant 32 to the SPG.

For some applications, surgical guide 40 is coupled to or used in association with a second arch portion (not shown). The second arch portion is typically configured for placement on a lower dental arch of the subject. The second arch portion typically stabilizes upper arch portion 59, by pressing portion 59 against the upper teeth and palate. Additionally or alternatively, a stabilizing element 90 is placed between the lower and upper dental arches of the subject, and facilitates the squeezing of arch portion 59 against the upper teeth and palate.

Figure 2:
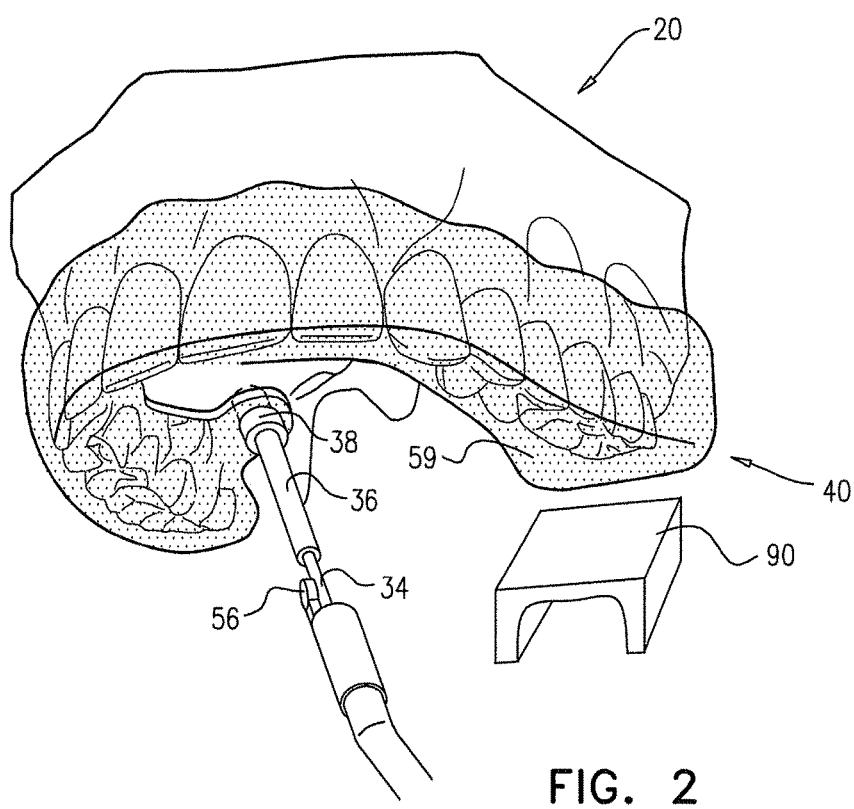
FIG. 2 is a schematic illustration of a delivery guide being advanced through a guide hole of an oral surgical guide, in accordance with some applications of the present invention.

Reference is made to FIG. 2, which is a schematic illustration of steerable delivery guide 34 being steered and advanced through guide hole 6 of surgical guide 40, in accordance with some applications of the present invention. Surgical guide 40 comprises arch portion 59 configured for placement on dental arch 54 and extension portion 58 which is shaped to define guide hole 6. Extension portion 58 contacts the roof of the oral cavity of the subject, and guide hole 6 is thereby automatically placed over the entrance to the greater palatine foramen of the subject.

Thus, in accordance with some applications of the present invention, surgical guide 40 is configured to guide an operating physician to the location of the greater palatine foramen of the subject, to facilitate advancement of guide 34 therethrough. Additionally, guide hole 6 in the surgical guide facilitates penetration of the mucosa at an appropriate angle for entrance into the greater palatine foramen at an angle suitable for advancement of guide 34 through the canal. Further additionally, the CT data in combination with the surgical guide provide the operating physician with information regarding the anatomical structure of the greater palatine canal, thereby facilitating navigation and advancement of neural stimulator implant 32 coupled to steerable delivery guide 34 through the canal.

For some applications, a length of a portion (e.g., a protrusion) of surgical guide 40 controls the degree to which neural stimulator implant 32 may be inserted into the canal. In other words, the length of the portion (e.g., protrusion) inhibits excessive insertion of implant 32 into the canal, and is designed such that the length of the portion controls the distance to which neural stimulator implant 32 is advanced in the canal. Thus, advancement of implant 32 is terminated based on contact of a portion of the delivery guide with the portion of the surgical guide that has a length corresponding to the location of the SPG. The location of the SPG and the shape of the canal are assessed by a pre-operative CT scan, and surgical guide 40 is typically configured to facilitate insertion of neural stimulator implant 32 to the location of the SPG based on the CT scan data. The shorter the length of the portion (e.g., the protrusion) of surgical guide 40, the farther neural stimulator implant 32 is advanced in the canal.

Figure 3A:
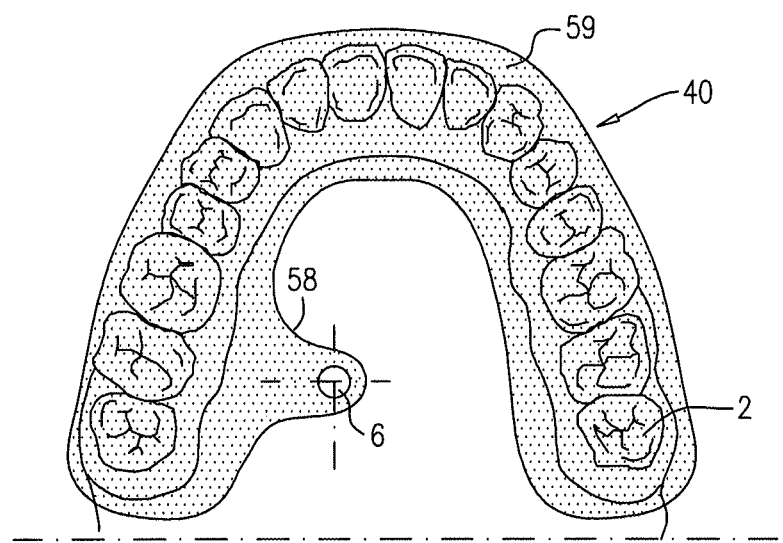
FIGS. 3A, 3B, 3C, 3D, 3E, 3F, 3G and 3H are schematic illustrations of various configurations of the surgical guide shaped to define a guide hole for locating the entrance to the greater palatine canal, in accordance with some applications of the present invention.
Figure 3B:
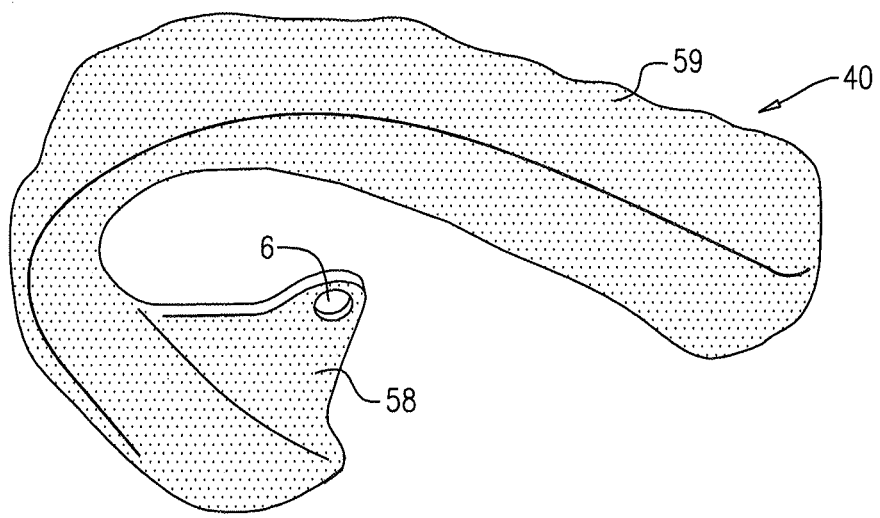

FIGS. 3A-B are schematic illustrations of surgical guide 40 comprising arch portion 59 configured for placement on teeth 2 of a subject, or on gums of the subject, in accordance with some applications of the present invention. Extension portion 58 extends, lingually and in a superior direction, away from arch portion 59 and is placed in contact with the roof of the oral cavity of the subject. Extension portion 58 is shaped to define guide hole 6, which is automatically placed over the entrance to the greater palatine foramen when surgical guide 40 is placed on teeth 2, or gums, of the subject. For some applications, an adhesive, e.g., glue, is used to secure guide 40 to the teeth or gums of the subject.

Typically the location of the greater palatine foramen varies among the population. For example, in some subjects the greater palatine foramen is associated with the upper third molar tooth. In other subjects, the greater palatine foramen is associated with the second molar or between the second and third molar. It is noted that the location of guide hole 6 is shown in the figures by way of illustration and not limitation. It is understood that the location of guide hole 6 is set based on the location of the greater palatine foramen of each particular subject. Surgical guide 40 is typically custom-made based on a CT scan of the subject, such that guide hole 6 is placed over the greater palatine foramen of each individual subject, in order to guide the physician to the correct location.

Figure 3C:
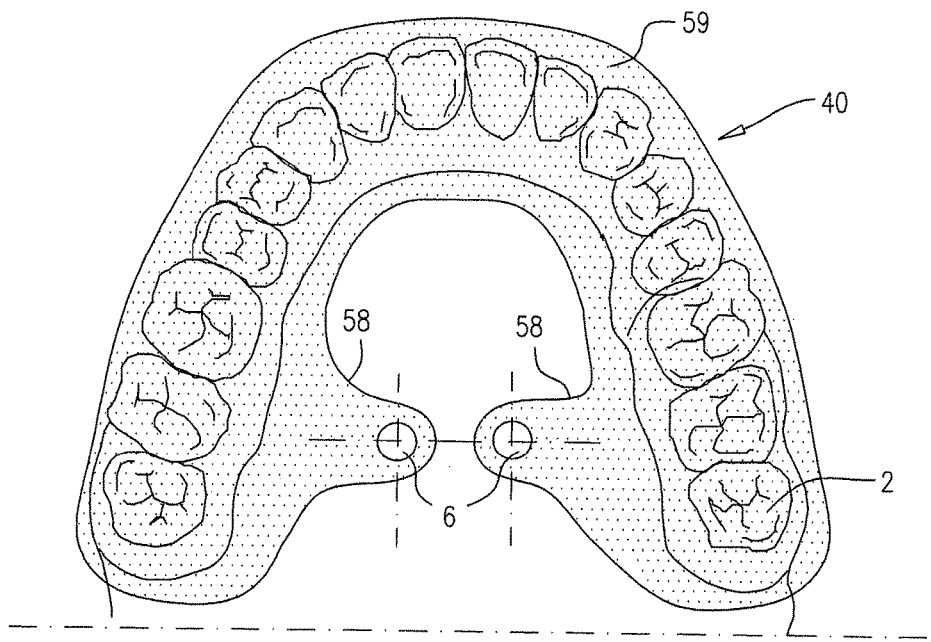

Reference is now made to FIG. 3C. For some applications, surgical guide 40 comprises a second extension portion 58 located contralateral to extension portion 58, for bilateral electrical stimulation of the right and left SPG (e.g., for treatment of vascular dementia).

For some applications, surgical guide 40 is fabricated by three-dimensional (3D) printing. For some applications, for example in order to reduce fabrication time of guide 40, guide 40 comprises a non-patient-customized portion (e.g., made of metal, molded plastic, a generic part made of a 3D-printed material, and/or a combination of materials (e.g., a combination of plastic and metal), and a patient-customized portion (e.g., produced by 3D printing especially for the patient).

Alternatively, surgical guide 40 is manufactured by molding a pliable material, such as a thermoplastic sheet, and drilling guide hole 6 with a drill. (After the molding, a suitable process is used to make the pliable material generally rigid, e.g., by heat treatment or ultraviolet curing.)

Typically, the drill has markers (e.g., RF coils, or optical markers) in order to ensure drilling of guide hole 6 in a proper location corresponding to the greater palatine foramen. Typically, prior to drilling of the hole, the unfinished surgical guide is placed on teeth or gums of the subject and CT data of the oral cavity is acquired. Subsequently, the surgical guide is removed from the subject's mouth. Using a processor, the CT data of the oral cavity with the surgical guide is received and is used to determine a desired position of the drill. Directional and orientational guidance for performing the drilling is generated using the one or more markers on the drill. Subsequently, the processor guides drilling of the hole in the surgical guide at a site on the surgical guide which corresponds to the greater palatine foramen of the subject.

Figure 3D:
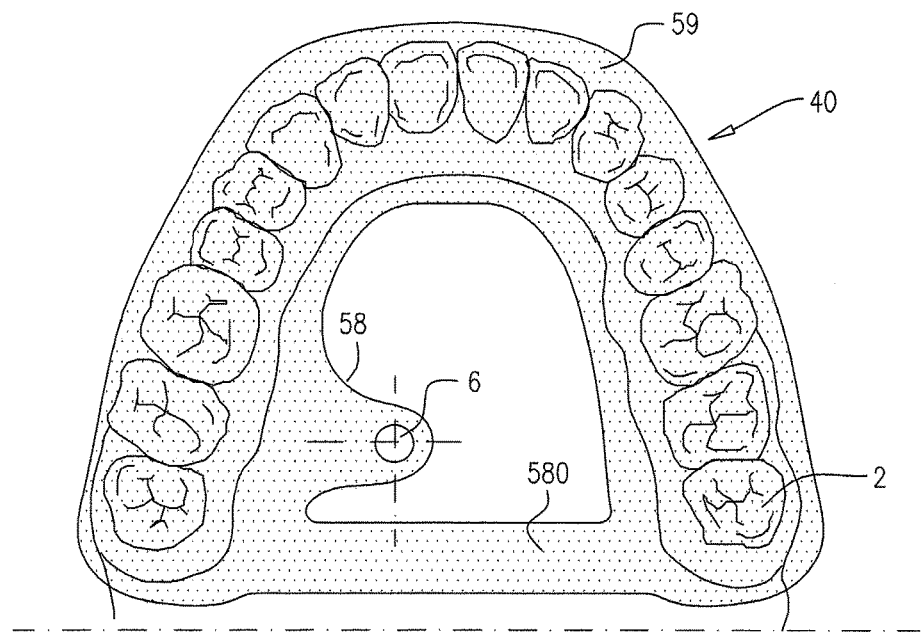

Reference is now made to FIG. 3D. For some applications, surgical guide 40 additionally comprises a support element 580. Support element 580 typically extends from a first side of surgical guide 40 to a second side of guide 40 (e.g., an opposite side, e.g., extending from the left to the right side). Support element 580 typically extends from a left side of arch portion 59 to a right side of arch portion 59, posterior to a canine region of oral surgical guide 40. Support element 580 typically enhances rigidity of guide 40 and inhibits movement of surgical guide 40 when pressure is applied to guide 40 during insertion of angular guide 36 through hole 6. Additionally or alternatively, surgical guide 40 is thickened in order to add to rigidity thereto, optionally in the absence of support element 580.

Figure 3E:
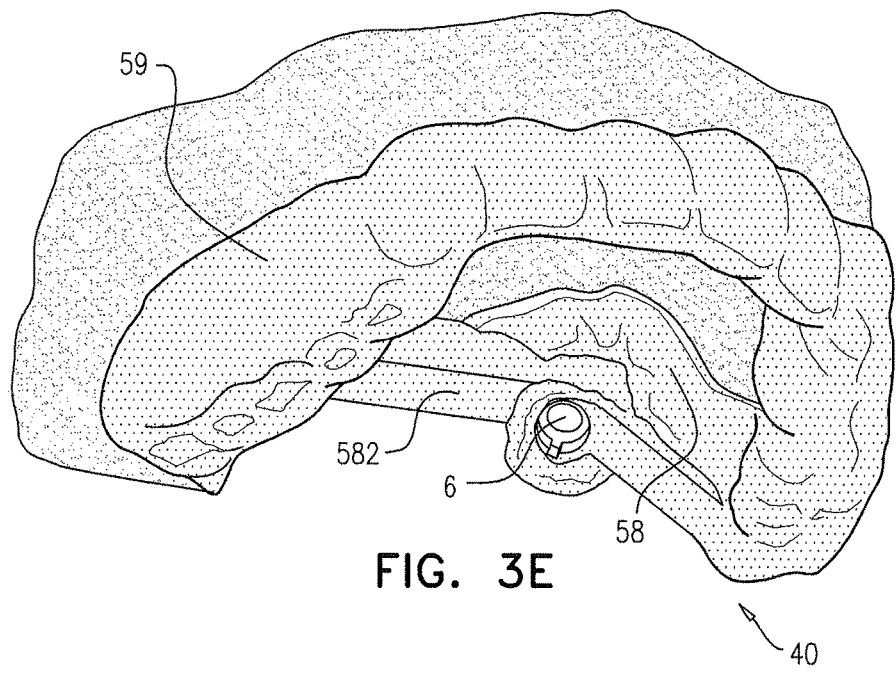
Figure 3F:
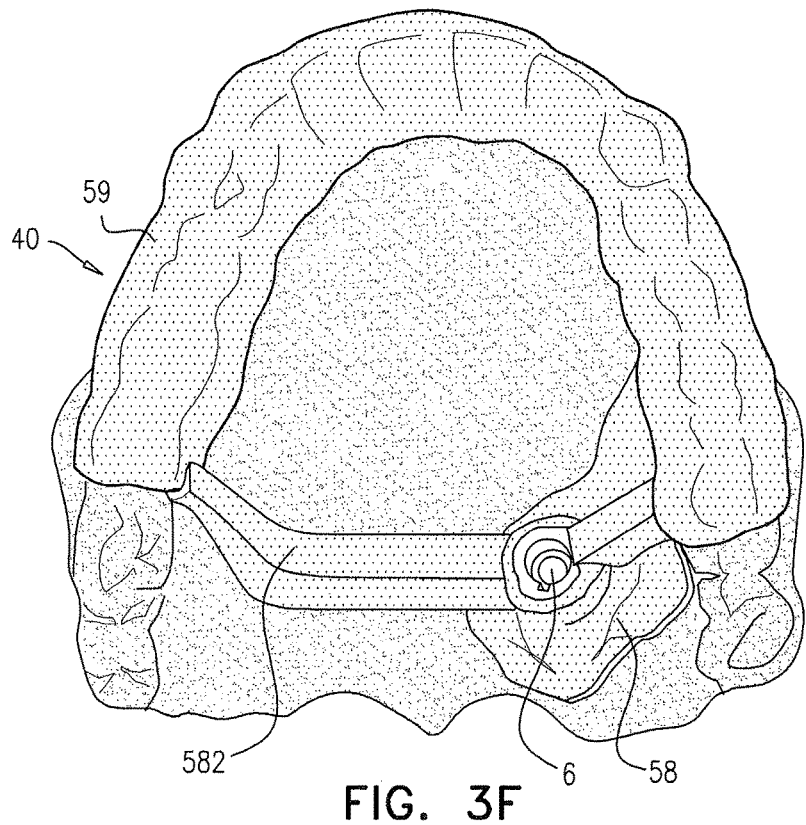

Reference is now made to FIGS. 3E and 3F. For some applications, surgical guide 40 comprises a support element 582. Support element 582 typically extends from extension portion 58 to a right side of arch portion 59, posterior to a canine region of oral surgical guide 40. Support element 582 is generally the same as support element 580 and enhances rigidity of guide 40 and inhibits movement of surgical guide 40 when pressure is applied to guide 40 during insertion of (for example) angular guide 36 through hole 6.

Figure 3G:
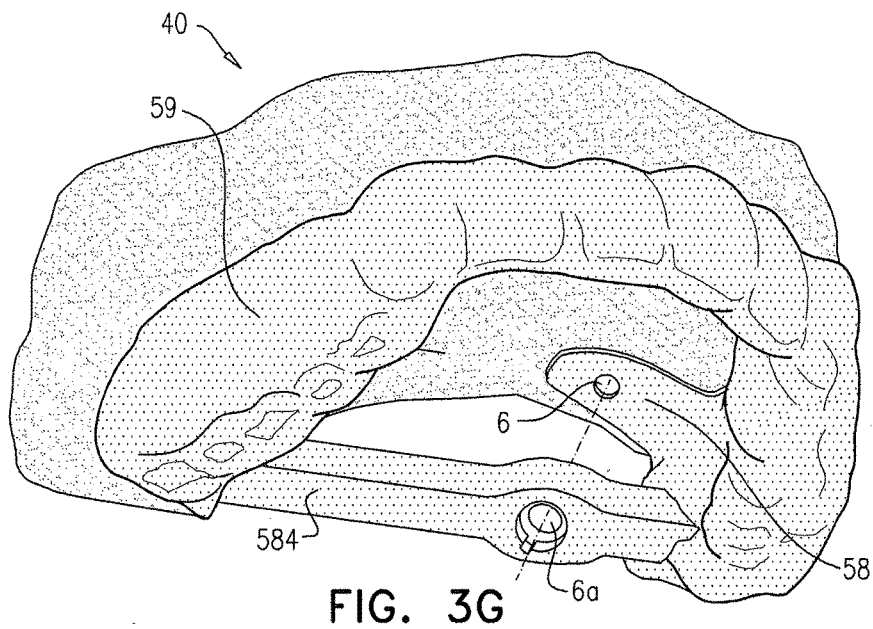
Figure 3H:
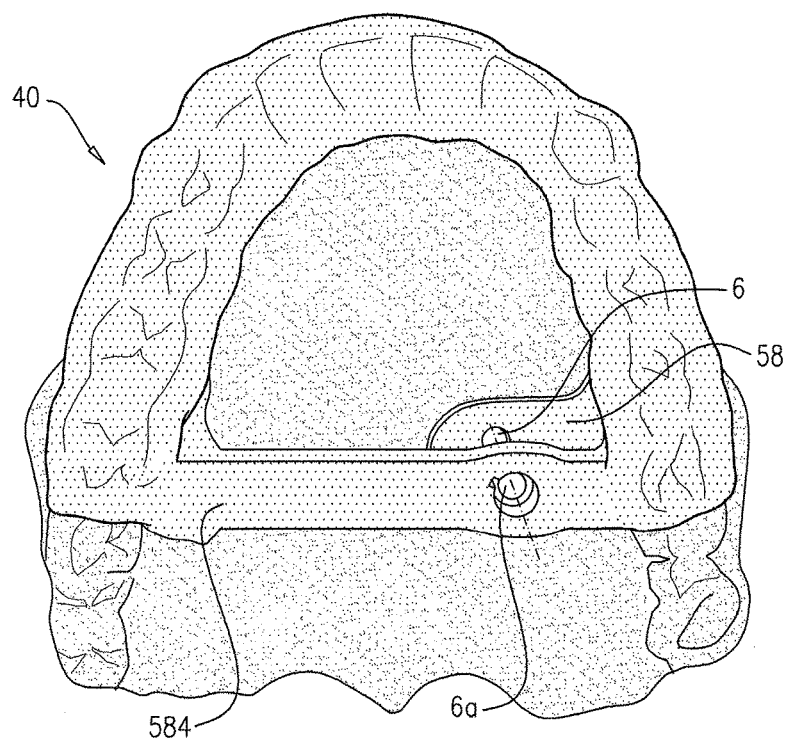

Reference is now made to FIGS. 3G and 3H. For some applications, surgical guide 40 comprises a support element 584. Support element 584 typically extends from a left side of arch portion 59 to a right side of arch portion 59, posterior to a canine region of oral surgical guide 40 and inferior and in a lingual direction with respect to arch 59 (i.e., more at the level of the teeth than at the level of the palate). For such applications, support element 584 is shaped to define a guide hole 6a which is aligned with guide hole 6 in extension portion 58, allowing access to guide hole 6 through guide hole 6a. Optionally but not necessarily hole 6a is shaped to define a funnel. Support element 584 enhances rigidity of guide 40 and inhibits movement of surgical guide 40 when pressure is applied to guide 40 during insertion of angular guide 36 through hole 6.

Figure 4C:
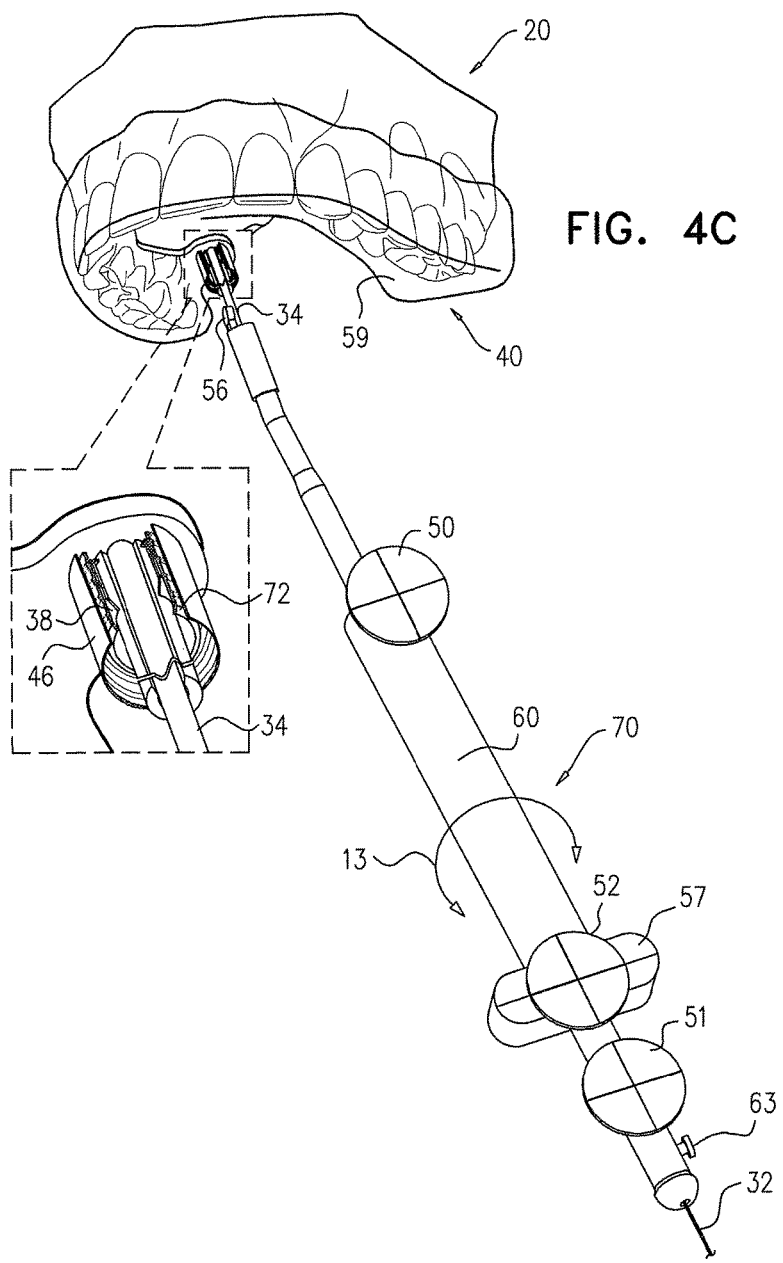
Figure 4D:
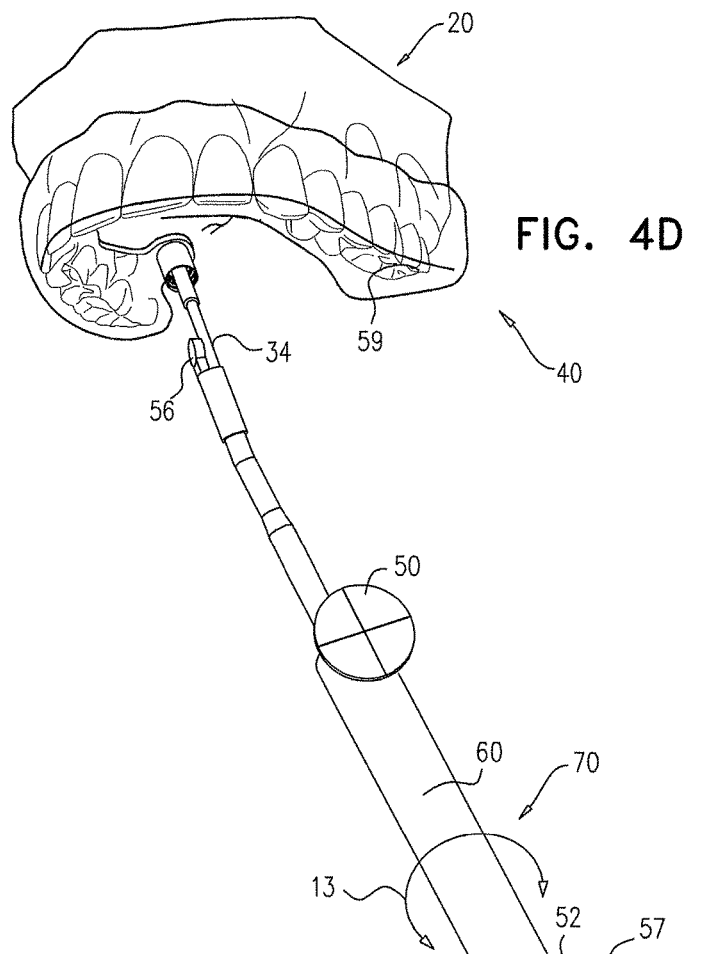

Reference is made to FIGS. 4A-C, which are schematic illustrations of dental arch portion 59, comprising a locking mechanism 94, in accordance with some applications of the present invention. Locking mechanism 94 is configured to lock tool 70 and angular guide 36 in place with respect to surgical guide 40, such that delivery guide 34 and implant 32 are advanced accurately through guide hole 6. Generally, locking mechanism 94 comprises (a) a projecting portion of surgical guide 40 which is typically shaped to provide a screw thread on an outer surface of projection 72, and (b) a screw thread on an inner surface of the locking portion on tool 70. The screw threads on projection 72 and on tool 70 engage each other, thereby locking the projection to the tool.

FIG. 4A shows surgical guide 40 comprising arch portion 59 and extension portion 58. For some applications, extension portion 58 further comprises projection 72, which protrudes away from extension portion 58. Projection 72 is typically shaped to define the screw thread profile described hereinabove, on an outer surface of the protrusion (as shown). (Alternatively, the screw-thread is on the inner surface of the projection.)

Reference is made to FIG. 4B. For some applications, angular guide 36, which is mounted to tool 70, comprises locking portion 46 which is shaped to define a screw thread (described hereinabove), configured to engage projection 72 on surgical guide 40. Locking portion 46 is typically rotated in order to lock locking portion 46 to projection 72, thereby restricting motion of delivery guide 34.

FIG. 4C shows locking mechanism 94 in a locked state thereof. It is to be noted that surgical guide 40 is shaped to define a screw-shaped projection 72 by way of illustration and not limitation. In general, surgical guide 40 may comprise a first coupling, and guide 36 and/or tool 70 may comprise a second coupling. The first coupling may comprise a male coupling while the second coupling may comprise a female coupling, or vice versa.

It is noted that locking mechanism 94 is described by way of illustration and not limitation. For some applications, tool 70 and angular guide 36 are locked in place with respect to surgical guide 40 by plugging distal end 38 into guide hole 6. For example, locking of tool 70 with respect to surgical guide 40 is allowed when angular guide 36 is plugged into guide hole 6 at an appropriate angle and/or a particular orientation (e.g., via a fin extending at 12 o'clock that fits into a corresponding slot on surgical guide 40).

Figure 5:
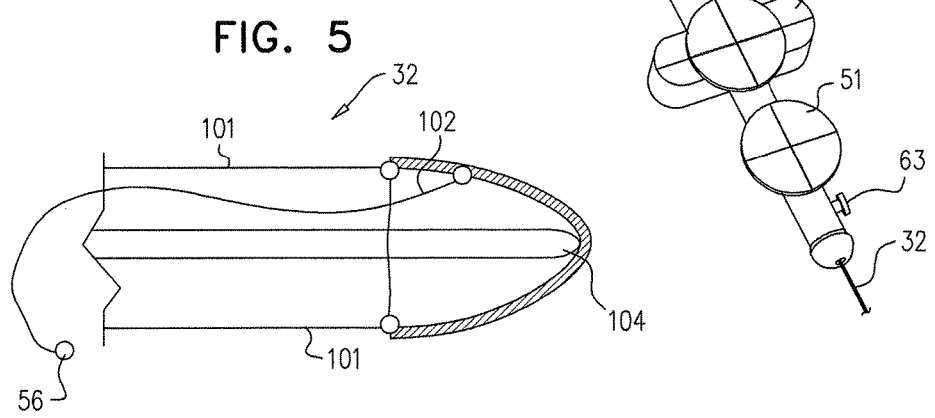
FIG. 5 is a schematic illustration of the neural stimulator implant for electrical stimulation of a sphenopalatine ganglion (SPG) of a subject, in accordance with some applications of the present invention.

Reference is made to FIG. 5, which is a schematic illustration of an example of neural stimulator implant 32 for electrical stimulation of a sphenopalatine ganglion (SPG) of the subject, in accordance with some applications of the present invention.

Neural stimulator implant 32 is typically 0.5-1.5 mm in diameter, e.g., 1 mm. Thus, advancement of implant 32 typically does not require dilation of the greater palatine canal. Alternatively, placement of implant 32 includes pre-dilation of the greater palatine canal.

For some applications, neural stimulator implant 32 is electrically coupled to circuitry 56 which is adapted to be placed outside the greater palatine canal, e.g., the circuitry may be positioned submucosally in the oral cavity. For other applications, circuitry 56 is adapted for insertion into the oral mucosa of the subject. Following insertion of electronic circuitry 56 into the mucosa, the surgeon may seal the puncture site by applying pressure to the puncture site in order to facilitate self-healing of the hole, e.g., by keeping a finger on the puncture site. Typically, neural stimulator implant 32 itself is configured for puncturing the oral mucosa.

For some applications, electronic circuitry 56 is advanced along an exterior of delivery guide 34 (as shown), until circuitry 56 is inserted into the mucosa.

As shown in FIG. 5, implant 32 typically comprises at least two steering wires 101 configured to facilitate steering of implant 32 within the greater palatine canal. Additionally, implant 32 comprises a stimulation wire 102 coupled to an electrode 106, for electrical stimulation of the sphenopalatine ganglion (SPG) of the subject, once implant 32 is delivered to the vicinity of the SPG.

Typically, the delivery apparatus comprises a pusher 104 disposed within delivery guide 34 (FIG. 1), which is configured to advance implant 32 within the greater palatine canal, e.g., by pushing an inner surface of electrode 106.

Figure 6:
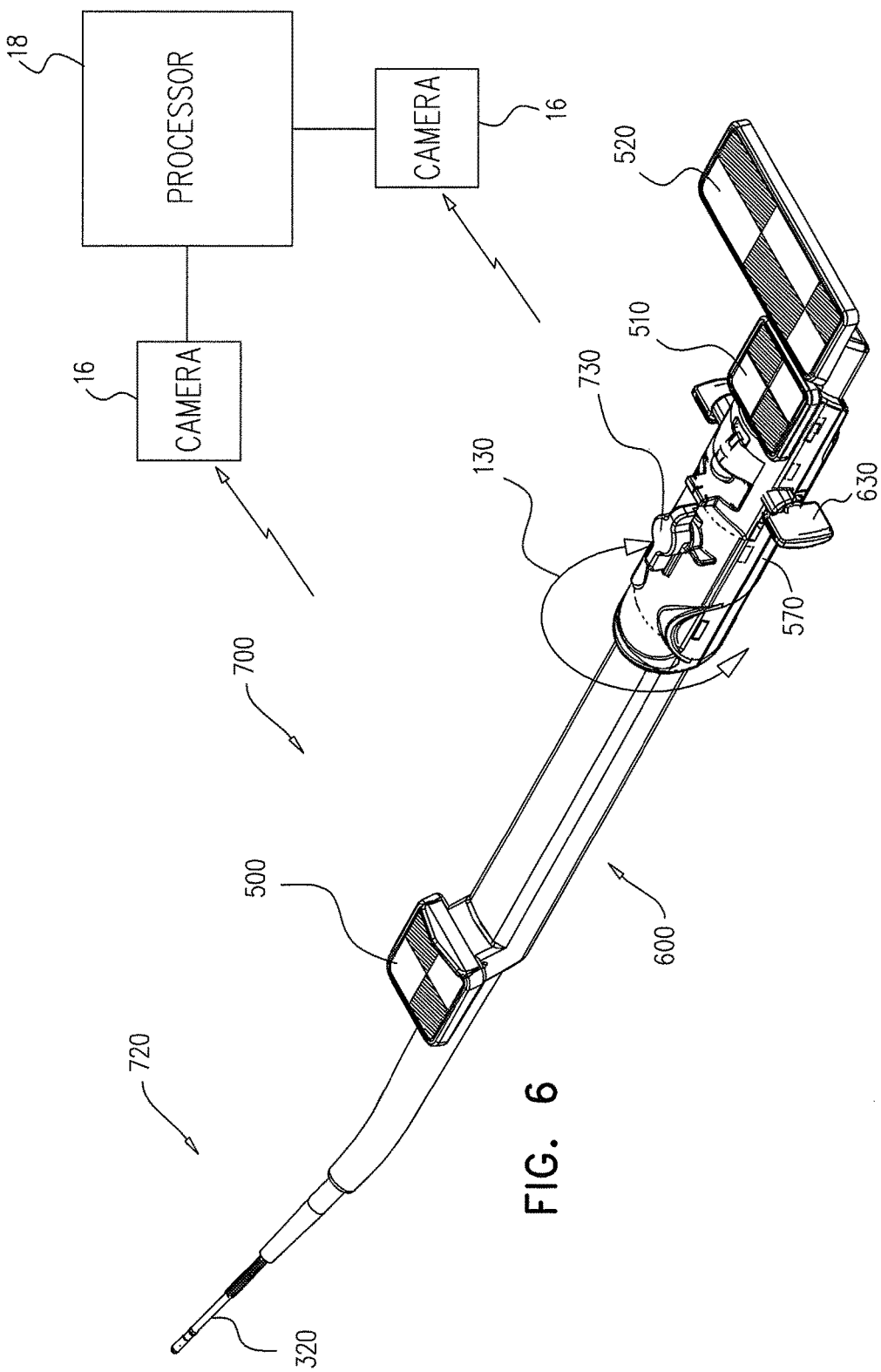
FIG. 6 is a schematic illustration of a tool for facilitating delivery of a neural stimulator implant for electrical stimulation of a sphenopalatine ganglion (SPG) of a subject, in accordance with some applications of the present invention.

Reference is made to FIG. 6, which is a schematic illustration of a delivery tool 700 for facilitating delivery of a neural stimulator implant 320 (described hereinbelow with reference to FIGS. 9A-B and 10) to a sphenopalatine ganglion (SPG) of a subject, for electrical stimulation of the SPG, in accordance with some applications of the present invention.

Tool 700 is typically used in combination with surgical guide 40 (described herein with reference to FIGS. 3A-C) and directs advancement of the neural stimulator implant through guide hole 6 in surgical guide 40 and subsequently through the greater palatine foramen into the greater palatine canal.

Tool 700 typically comprises a handle 600 and a distal tip portion 720. In general, prior to use, the neural stimulator implant is mounted in distal tip portion 720. FIG. 6 shows the implant partially protruding from tip portion 720, as it appears after it has been initially advanced into the greater palatine canal. (For clarity of illustration, surgical guide 40 and anatomy are not shown.) Overall, tool 700 facilitates advancement of the implant toward the sphenopalatine ganglion (SPG) of a subject.

Typically, distal tip portion 720 plugs into surgical guide 40 to facilitate accurate advancement of neural stimulator implant 320 through guide hole 6 in surgical guide 40. Handle 600 comprises a slide-bar 570, which is slidable with respect to handle 600. Slide-bar 570 is typically locked in place, until it is released by a release mechanism 730 (e.g., by turning a knob on handle 600), in order to allow advancement of the neural stimulator implant through the guide hole and into the greater palatine canal.

An operating physician typically slides slide-bar 570 along handle 600 in order to advance implant 320 out of tool 700 and distally through guide hole 6. Additionally, slide-bar 570 provides steering functionality for facilitating orientation of the implant in the greater palatine canal. Advancement of slide-bar 570 with respect to handle 600 advances the implant through the canal.

For some applications, slide-bar 570 is rotated as indicated by arrow 130, in order to orient implant 320 within the greater palatine canal. Typically, a distal-most portion of implant 320 is oriented at a non-zero angle with respect to a longitudinal axis of the implant, such that the implant may be steered in the palatine canal in an analogous fashion to that in which a steerable guidewire is steered in the vasculature of a subject.

For some applications, the passage of implant 320 into the greater palatine canal is facilitated by image-guided surgical techniques, e.g., using optical fiducial markers 500, 510 and 520 on tool 700. Two or more cameras 16 are used to image markers 500, 510, and 520. An image-guided surgery processor 18 coupled to receive the image data from the cameras utilizes location data derived from markers 500, 510 and 520, in combination with fiducial markers on the subject (e.g., placed on surgical guide 40, or the teeth, face or a head of the subject) to register pre-operative CT data (showing bony structures in general and the greater palatine canal in particular) with the current position of the tool and thereby facilitate steering and advancement of implant 320 through the greater palatine canal.

Alternatively or additionally, the image-guided surgery processor utilizes location data derived from markers 500, 510 and 520 in combination with registration data obtained by (a) contacting a tool with a fiducial marker to multiple spots on the subject's head that can also be identified in the pre-operative CT image, and/or (b) visualizing markers 500, 510, and/or 520 when distal tip portion 720 is secured to surgical guide 40.

For some applications (in addition to or instead of using markers 500, 510, and 520), handle 600 comprises a linear and/or an angular encoder configured to facilitate recording of location data indicative of the current position and orientation of neural stimulator implant 320.

It is noted that processor 18 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. Such program code and/or data, when provided to the processor, produce a machine or special-purpose computer, configured to perform the tasks described herein.

Figure 7:
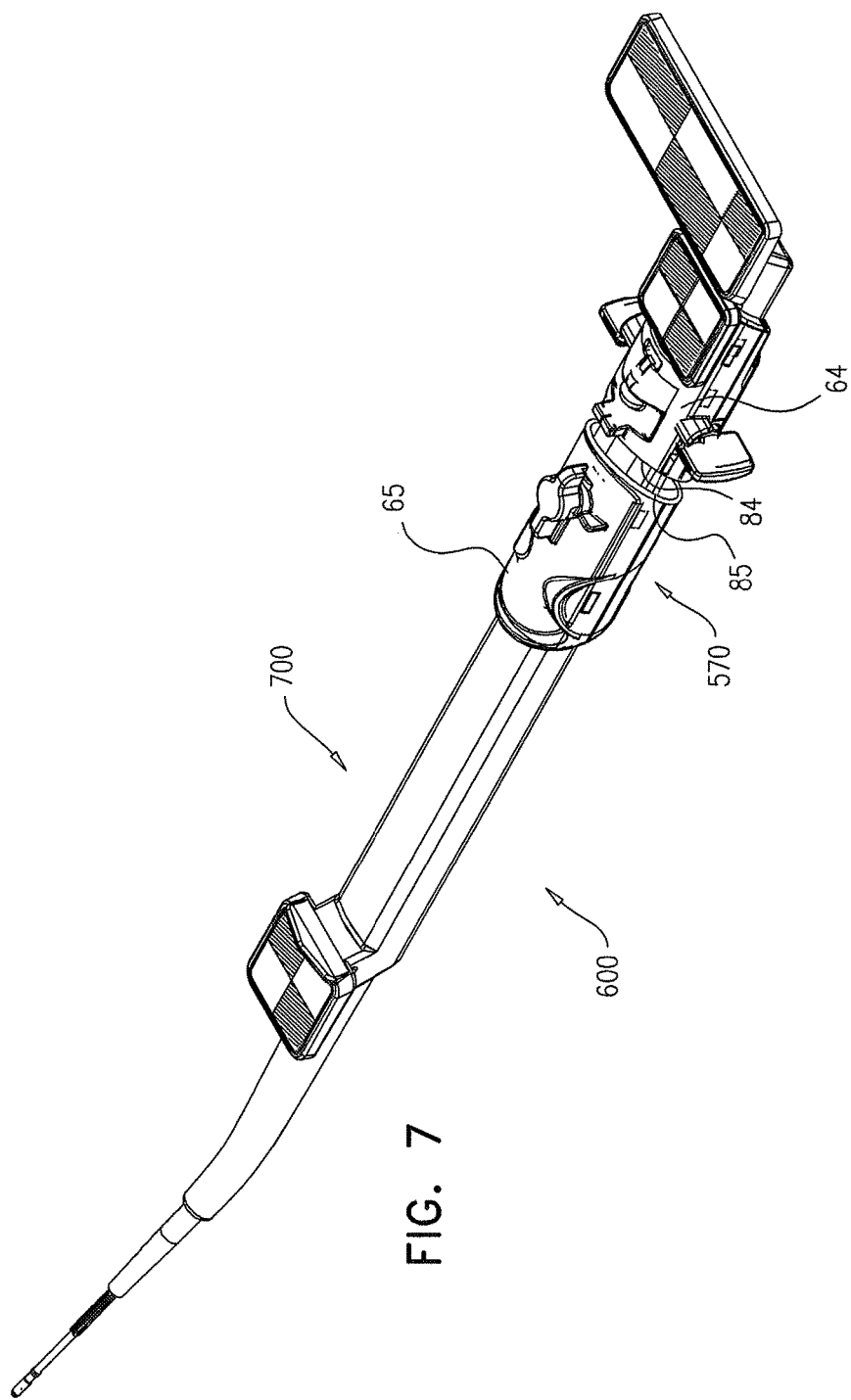
FIG. 7 is a schematic illustration of a tool for facilitating delivery of a neural stimulator implant for electrical stimulation of a sphenopalatine ganglion (SPG) of a subject, in accordance with some applications of the present invention.

Reference is made to FIG. 7, which is a schematic illustration of delivery tool 700, generally as described herein with reference to FIG. 6. For some applications, slide-bar 570 of handle 600 comprises a distal portion 65 and a proximal portion 64, which are held connected to each other by first and second magnetic elements 85 and 84 coupled to the proximal and distal portion of slide-bar 570 and magnetically coupled to each other. Proximal portion 64 of slide-bar 570 is coupled to implant 320 such that distal advancement of proximal portion 64 of the slide-bar produces distal advancement of the implant. Typically, the physician advances the slide-bar by gripping distal portion 65 and applying a distally-directed force thereto, such that the magnetic coupling causes proximal portion 64 to advance distally, and thereby cause distal advancement of implant 320. If the force applied to distal portion 65 of slide-bar 570 in a distal direction exceeds a threshold (e.g., due to advancement of the implant being impeded), this typically breaks the coupling between the first and second magnetic elements, thereby discontinuing advancement of implant 320 and alerting the operating physician to an issue relating to the proper placement of implant 320.

Figure 8:
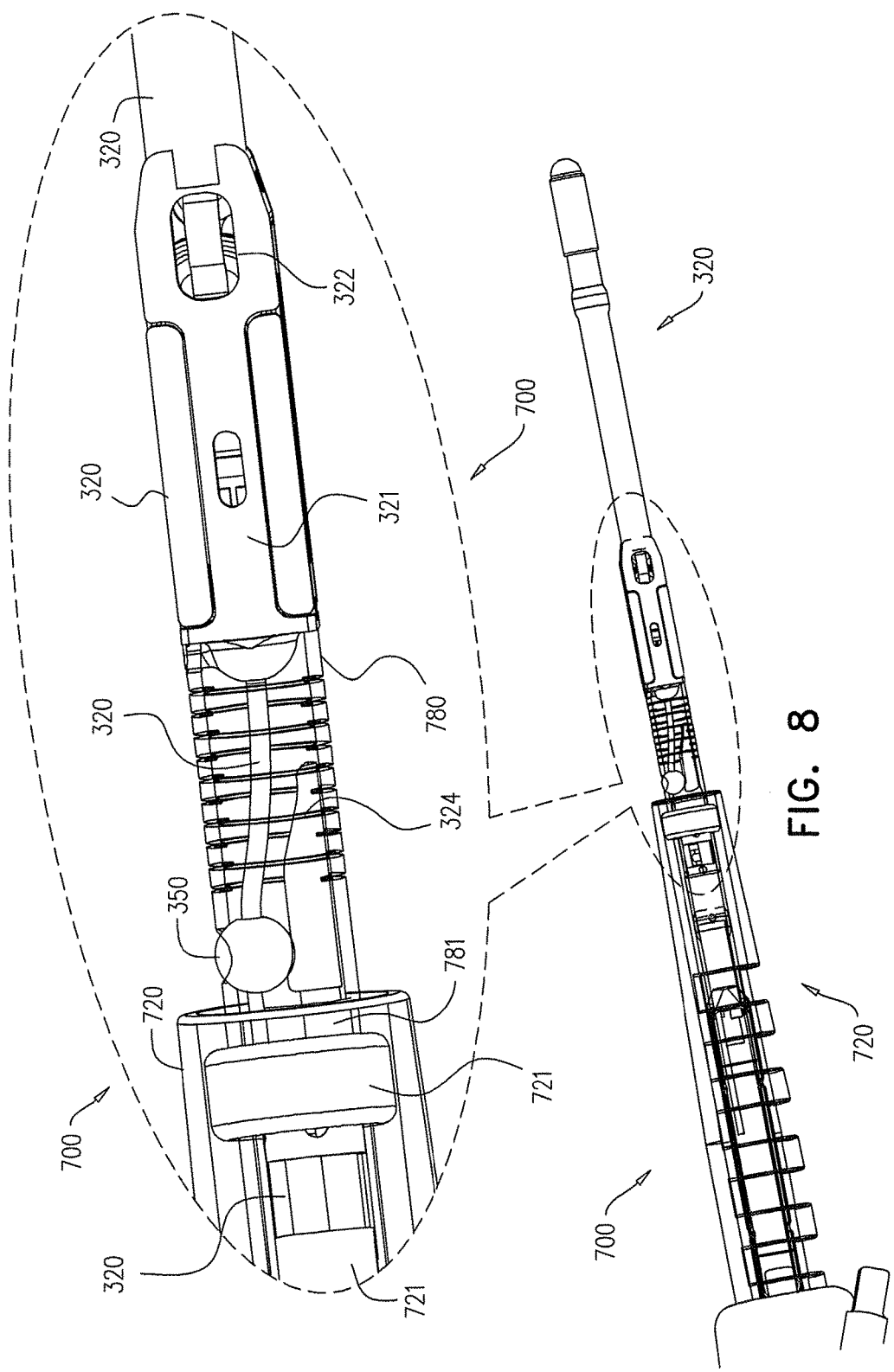
FIG. 8 is a schematic illustration of a neural stimulator implant mounted onto a tool for facilitating delivery thereof for electrical stimulation of a sphenopalatine ganglion (SPG) of a subject, in accordance with some applications of the present invention.

Reference is made to FIG. 8, which is a schematic illustration of neural stimulator implant 320 extending from distal tip portion 720 of tool 700, in accordance with some applications of the present invention. (Other components of tool 700 are labeled 721 in FIG. 8). For some applications, tool 700 comprises at a distal portion thereof, a stainless steel tube 780 configured to engage a locking element 350 of implant 320. An engaging element 781 is configured to engage locking element 350 of implant 320 (shown in FIG. 8 as a ball by way of illustration and not limitation). Typically, activation of an implant-release mechanism 630 (e.g., by turning a knob as shown in FIG. 6) causes engaging element 781 to disengage from locking element 350, allowing all implantation apparatus in the greater palatine canal to be withdrawn, generally without dislodging implant 320 from its implantation location near the SPG.

Typically, tube 780 is shaped to define a series of slits 324 longitudinally aligned along tool 700, each slit disposed at an angular offset (e.g., a 180 degree offset as shown in FIG. 8, or alternatively at a 90 degree offset, not shown) from an adjacent one of the slits. The slits permit tube 780 to bend in a range of directions, e.g., in any direction, to facilitate advancement of the implant through the greater palatine canal.

Implant 320 is generally flexible but typically also comprises a rigid portion 321 which houses a receiving coil 322 configured to receive power from a remote power source to power implant 320.

Reference is now made to FIGS. 9A-11, which are different views of implant 320, in accordance with some applications of the present invention. As shown, implant 320 comprises proximal 352 and distal 354 portions. Implant 320 is a generally flexible, elongate implant having electrodes (e.g. a dome electrode 12 and a second electrode 14) at the distal portion thereof and an unconstrained shape that is curved, i.e., bent, in a vicinity of the distal portion (e.g., proximal to electrode 14, or between electrodes 12 and 14).

FIGS. 9A-B and 10 show implant 320 in a straight configuration. Typically, following the advancing of the implant and deployment thereof in the vicinity of the SPG, distal portion 354 of the implant is constrained and shaped differently due to the anatomy of the canal compared to its unconstrained shape. For example, distal portion 354 may be generally straight in the vicinity of the SPG, based on the anatomy of some subjects, or distal portion 354 may be curved at its implantation site in the vicinity of the SPG.

Implant 320, in particular distal portion 354, is typically configured to puncture oral mucosa of the subject in order to allow advancement of implant 320 into the greater palatine canal. For some applications, implant 320 is not configured to puncture the oral mucosa, but instead a distal portion of tool 700 is configured to puncture oral mucosa.

It is noted that for some applications, implant 320 comprises two or more portions of electronic circuitry comprising multiple circuitry units 326, at discrete longitudinal sites along implant 320 (shown in FIG. 10). Typically, the electronic circuitry is divided into first and second portions 17 and 19, which are coupled respectively to proximal and distal sites of neural stimulator implant 320 that are flexibly coupled to each other. Division of the electronic circuitry into two or more portions typically facilitates smooth advancement of the implant in the canal.

For some applications, a flexible, connecting element 328 (e.g., a flexible printed circuit board) extends along implant 320 and connects first and second portions 17 and 19 of the electronic circuitry. Alternatively or additionally, a structural element 325 able to withstand compressive forces associated with the implantation is used to convey distally-directed forces toward the distal end of implant 320. For example, this structural element may comprise nitinol (and for some applications is not used to convey electrical signals between the first and second portions of the electronic circuitry). Structural element 325 comprising nitinol typically has a trained natural curve, which enables steering of implant 320 by rotating the handle 600 of tool 700 (FIG. 6). The curve in element 325 could be as shown in FIG. 11, or between the two electrodes on distal portion 354, or within 15 mm of the very distal tip.

Figure 11:
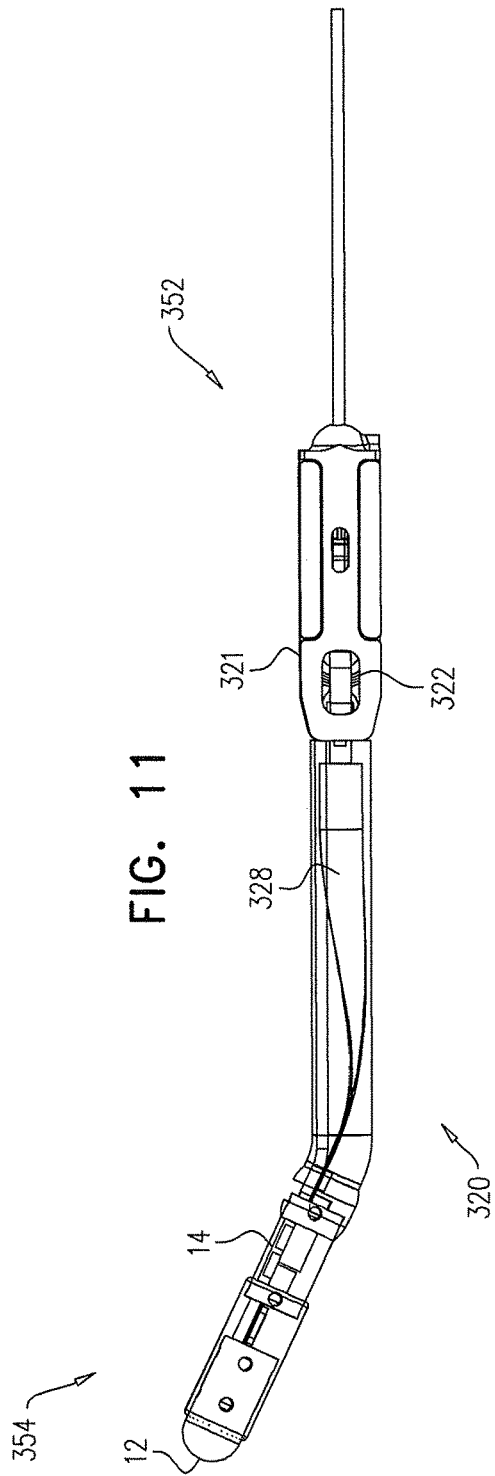
FIG. 11 is a schematic illustration of the neural stimulator implant having a bent distal end, in accordance with some applications of the present invention.

FIG. 11 shows neural stimulator implant 320 having a curved or bent distal end, as described hereinabove, in accordance with some applications of the present invention.

Reference is made to FIGS. 1-12C and FIGS. 14A-18C. For some applications, a surface shaped to define a guiding groove is generated (typically by a 3D printing process) based on CT data obtained by imaging the subject. Based on the CT data, the guiding groove is shaped in accordance with the subject's anatomy in order to guide the implant to the desired anatomical site, e.g., to guide steering of neural stimulator implants 32 and/or 320 through the greater palatine canal to the vicinity of the sphenopalatine ganglion (SPG).

Figure 12B:
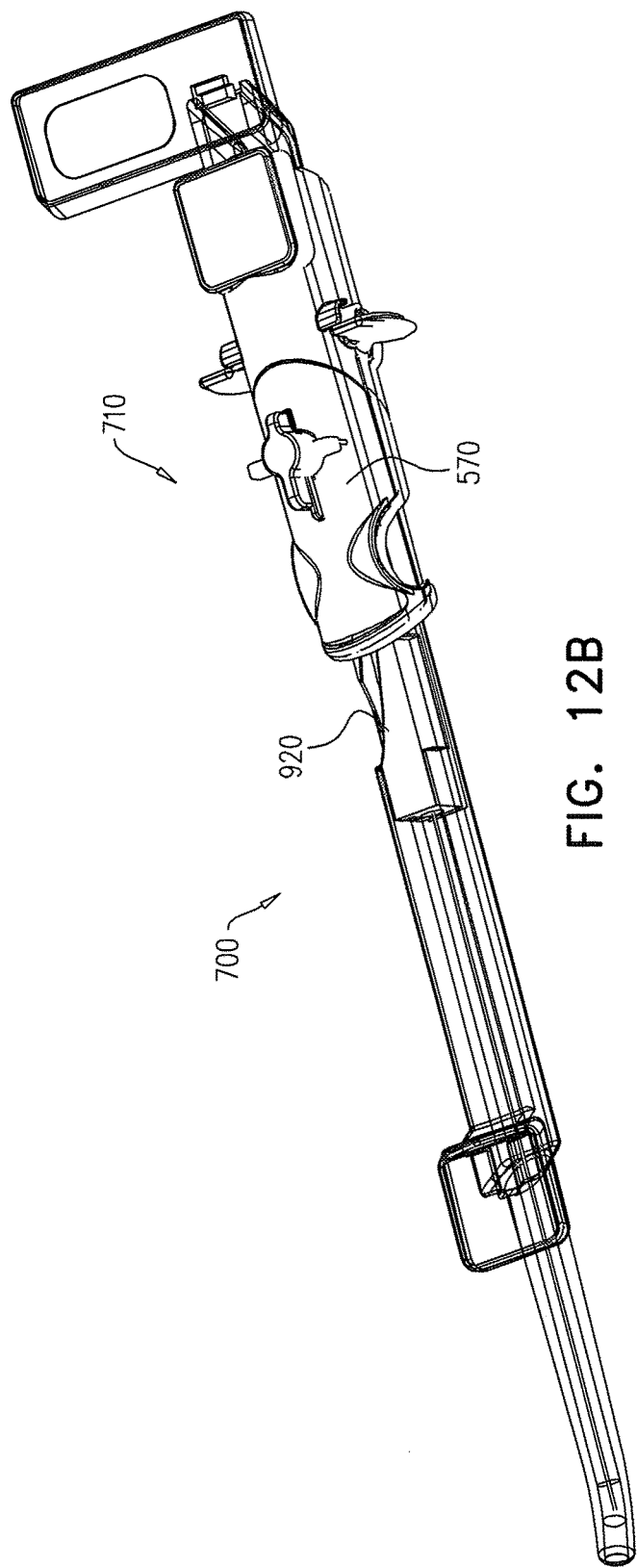
Figure 12C:
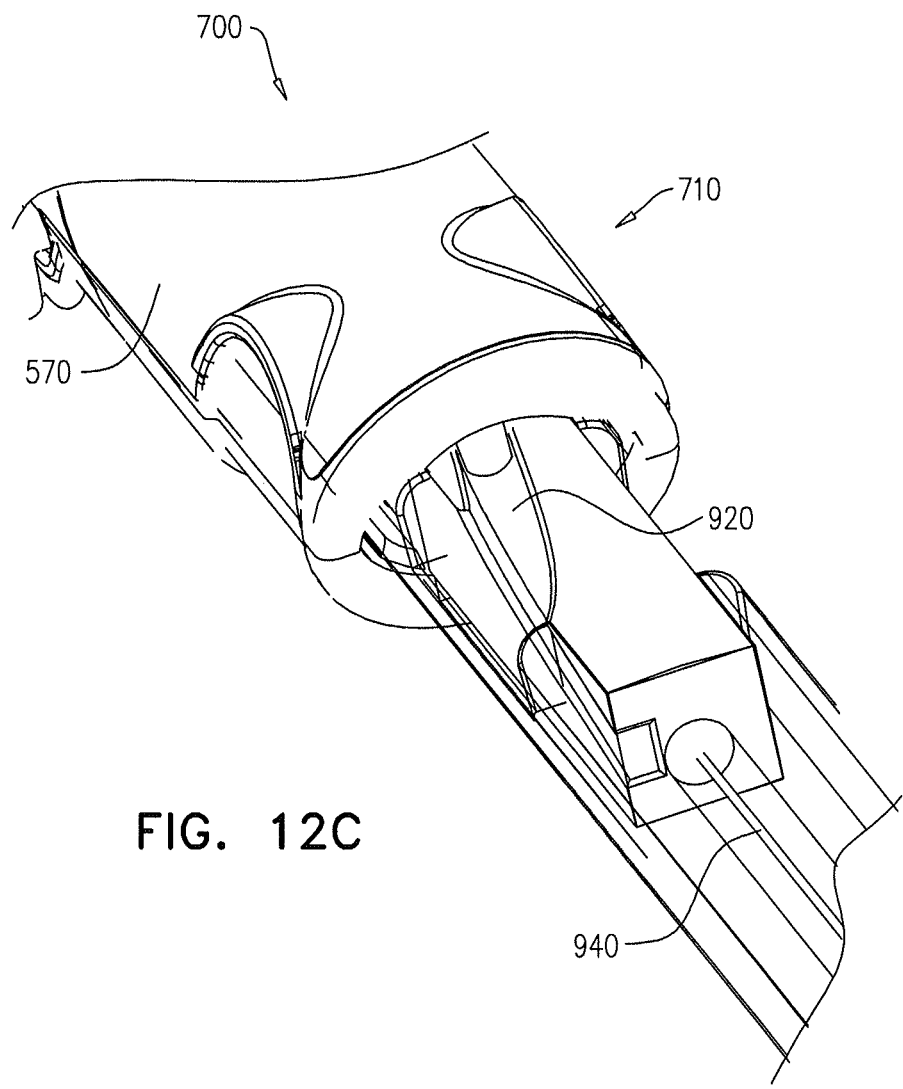

As shown in FIG. 12, a delivery tool, e.g., implantation tool 700, comprises a surface shaped to define a curved guide groove 920 at a proximal portion 710 of the delivery tool. Curved guide groove 920 is generated based on data obtained by imaging the anatomy of the subject, e.g., the greater palatine canal. A guiding pin 940 is typically disposed within curved guide groove 920, and is configured such that advancement of slide-bar 570 with respect to proximal portion 710 produces (1) relative motion of guiding pin 940 with respect to curved guide groove 920, and (2) rotation of slide-bar 570 with respect to a longitudinal axis of tool 700.

Typically, as the operating physician slides slide-bar 570 along handle 600, guide groove 920 correctly guides the pin, thereby steering the implant in the canal (i.e., by causing rotation of slide-bar 570 as indicated by arrow 130 in FIG. 6, at the correct point in the longitudinal advancement of slide-bar 570 to cause a corresponding steering of implants 32 and/or 320).

For some applications, guiding pin 940 is attached to delivery tool 700, e.g., guiding pin 940 is fixedly coupled to slide-bar 570 of tool 700. For such applications, the surface shaped to define curved guide groove 920 is a surface of tool 700. For other applications, guiding pin 940 is attached to tool 700 (e.g., to handle 600 and not to the slide-bar) and slide-bar 570 is shaped to define the surface with curved guide groove 920.

It is noted that these applications using the guiding groove may, but typically do not, utilize optical markers 500, 510, or 520, or many other electronic surgical guidance techniques known in the art. For some applications, the techniques described in this paragraph may be used for advancement of other tools, in sites other than the greater palatine canal (e.g., to facilitate endoscopic sinus surgery, or vascular catheterizations).

Reference is made to FIGS. 3A-B and FIG. 13. For some applications, surgical guide 40 is generated based on data from both a CT scan and an intra-oral scan. For such applications, an intra-oral scan of the upper palate of the subject is performed in addition to the CT scan, and the data from both scans are registered for preparation of surgical guide 40.

An intra-oral scan typically contributes to fabrication of a better-fitting surgical guide 40 by providing high-resolution data of the upper palate including mapping of soft-tissue anatomy such as oral mucosa. For example, a portion of surgical guide 40 that corresponds to a surface of gum tissue of the subject is typically shaped in a curved manner that matches curvature of the gum tissue.

Thus, hole 6 is properly placed over the soft tissue that covers the greater palatine foramen. Having the surgical guide fit better over the oral mucosa typically facilitates optimal puncturing and penetration of the greater palatine foramen.

As described hereinabove, data obtained from the CT scan regarding bone and hard tissue of the subject, are typically used to determine the location and angle of implant insertion as well as guiding advancement of the implant to the SPG. Combining the data from both the CT scan and the intra-oral scan typically results in an enhanced surgical guide 40 in which both bone structure and the shape of soft tissue of the oral cavity are both reflected in surgical guide 40.

FIG. 13 is a block diagram showing steps of obtaining both CT scan data and intra-oral scan data for preparation of a surgical guide, in accordance with some applications of the present invention. Typically, in step 80, a subject in need of electrical stimulation of the SPG is identified. A CT scan and an intra-oral scan are then performed, as shown in steps 81 and 82. In step 83 the data from the CT and intra-oral scans are registered, and subsequently the surgical guide is planned and fabricated using the data from both the CT and intra-oral scanning (steps 86 and 87). As described hereinabove, surgical guide 40 is typically fabricated by three-dimensional printing techniques.

It is however noted that for some applications, surgical guide 40 is generated based on CT data only. Alternatively, for some applications, surgical guide 40 is generated based on intra-oral scan data only.

For some applications in which surgical guide 40 is generated based on intra-oral scan data only, a CT scan is performed after surgical guide 40 is generated. For example, CT data of the subject may be acquired while surgical guide 40 is disposed within the oral cavity, and registration of surgical guide 40 with respect to hard tissue of the anatomy may be performed using one or more markers affixed to surgical guide 40, and/or using features of the anatomy (e.g., teeth) that are imaged in the CT scan and in the intra-oral scan. The CT data typically guide the surgeon to drill a hole in surgical guide 40 at a site on the surgical guide that corresponds to the greater palatine foramen of the subject. For example, this drilling may be facilitated by markers on the drill, as described hereinabove. Subsequently, to drilling the hole, surgical guide 40 may be placed in the mouth and used to facilitate a procedure, as described hereinabove.

Reference is now made to FIGS. 14A-B, which are schematic illustrations of apparatus 200 comprising neural stimulator implant 320 mounted onto delivery tool 700, in accordance with some applications of the present invention.

For applications shown in FIGS. 14A-17, neural stimulator implant 320 additionally comprises a shape-sensing optical fiber 420. Optical fiber 420 is optically couplable to an optical fiber shape-sensing system 426 (FIG. 16, not to scale), and is configured to change shape during delivery of implant 320 to the SPG through the greater palatine canal of the subject.

In accordance with shape-sensing optical fiber technology, optical fiber 420 is typically used to monitor a dynamic three-dimensional shape of a structure to which it conforms. In the context of the present application, optical fiber 420 is typically used to assess a three-dimensional shape of the greater palatine canal and monitor advancement and navigation of implant 320 distally in the canal by monitoring changes in the shape of optical fiber 420 during advancement.

Additionally or alternatively, optical fiber 420 is used to assess a position of neural stimulator implant 320 within the greater palatine canal based on a shape of the optical fiber during advancement. Typically, use of optical fiber 420 facilitates verifying orientation and location of implant 320 during and following deployment of the implant in the vicinity of the SPG, such that a post-operative CT scan is in many cases not necessary.

As noted hereinabove, optical fiber 420 is optically couplable to optical fiber shape-sensing system 426. The optical fiber shape-sensing system typically comprises fiber shape-sensing circuitry configured to process the optical signal from the optical fiber and generate an output indicative of the dynamic shape of optical fiber 420. (Typically the optical fiber shape-sensing circuitry 428 comprises a circuitry unit intended for multiple uses.) It will be appreciated that circuitry 428 may be standard circuitry of a multi-purpose computer, which performs the desired shape sensing operations due to software running on the computer.

Figure 15A:
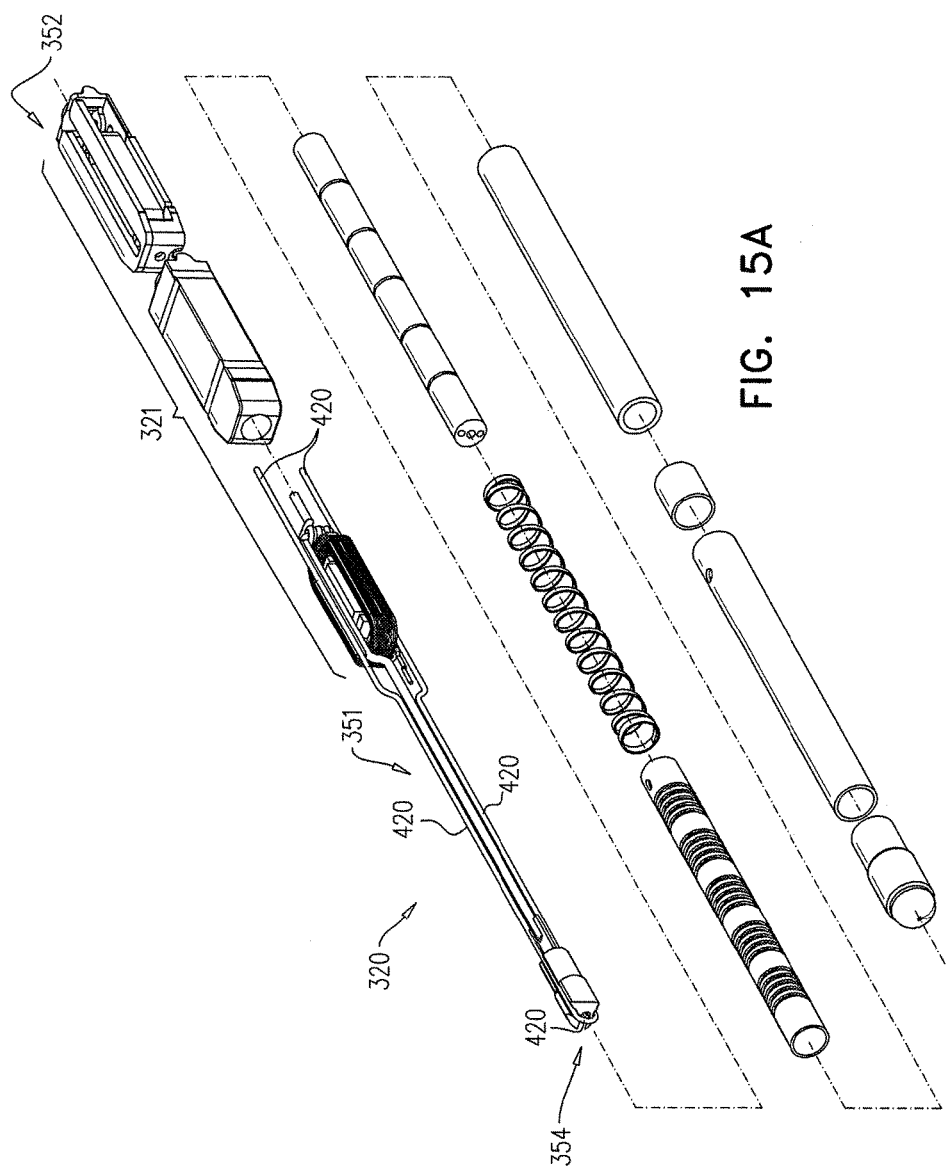

FIG. 15A is a schematic illustration of implant 320 and optical fiber 420. Typically optical fiber 420 contacts implant 320. For example, optical fiber 420 may be wrapped around a portion of neural stimulator implant 320, e.g., wrapped around distal portion 354 of the implant.

For some applications, optical fiber 420 is fixed to neural stimulator implant 320, and can only be separated from the implant by permanently changing a component (e.g., by cutting the fiber). In these applications, at least a portion of optical fiber 420 remains implanted at the SPG. For some applications, optical fiber 420 is shaped to define a predetermined breaking point 490 of optical fiber 420 between a distal portion 494 of optical fiber 420 and a proximal portion 492 of optical fiber 420, such that application of force to predetermined breaking point 490 causes breaking of optical fiber 420 at predetermined breaking point 490. For some applications, predetermined breaking point 490 is shaped to define a narrow portion of optical fiber 420. Breaking of optical fiber 420 at predetermined breaking point 490 typically facilitates separating of proximal portion 492 from distal portion 494 (e.g., by pulling), and subsequent removal of proximal portion 492 from the palatine canal. Distal portion 494 typically remains implanted at the SPG (typically along with neural stimulator implant 320).

Figure 15B:
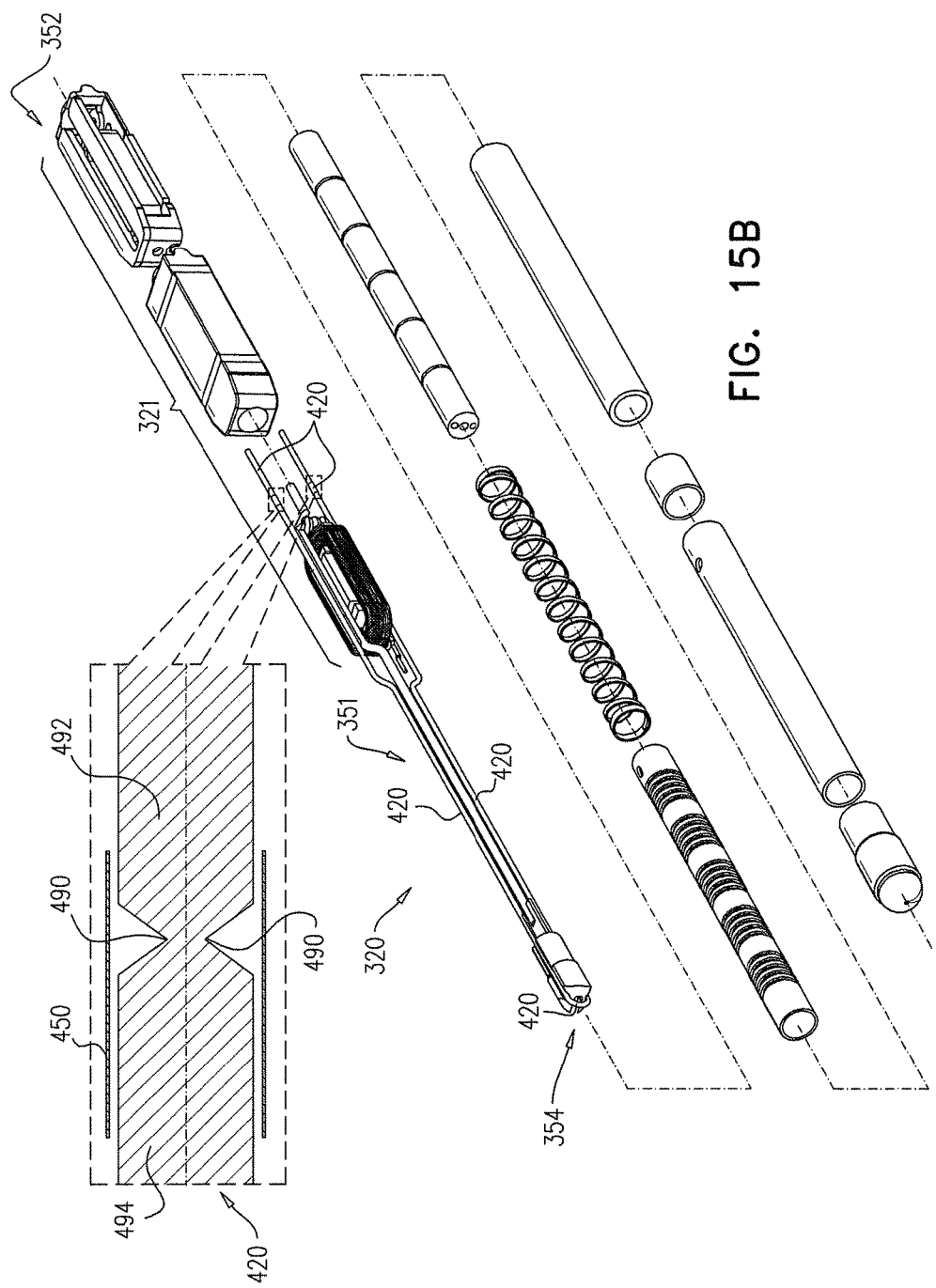

For some applications, optical fiber 420 is shaped to define more than one predetermined breaking point 490. For example, when optical fiber 420 is wrapped around a portion of neural stimulator implant 320, as shown in FIGS. 15A and 15B, optical fiber 420 may have a second predetermined breaking point 490 allowing removal of both proximal ends of optical fiber 420.

For some applications, optical fiber 420 is partly disposed within a sheath 450 such that predetermined breaking point 490 is disposed within sheath 450. Typically, some or all residue that may occur as a result of breaking of fiber 420 at predetermined breaking point 490 is contained in sheath 450.

Typically sheath 450 has a length of at least 2 mm and/or less than 15 mm, e.g., at least 5 mm and/or less than 10 mm. For some applications, as shown in FIG. 15B, only a small portion of proximal portion 492 is disposed in sheath 450, facilitating ease of removal of proximal portion 492 from the palatine canal.

Typically, sheath 450 stays in place after breaking of fiber 420 and removal of proximal portion 492 from the palatine canal. For some applications, sheath 450 is mechanically coupled to distal portion 494, e.g., glued to distal portion 494 or held by friction to distal portion 494, thus keeping sheath 450 in place after breaking of fiber 420.

Alternatively, sheath 450 may be pulled out of the palatine canal along with proximal portion 492. For example, the position of predetermined breaking point 490 within sheath 450 may define whether sheath 450 slides out of the palatine canal along with proximal portion 492 when proximal portion 492 is pulled proximally. For example, if most of the portion of fiber 420 that is disposed in sheath 450 is part of proximal portion 492, sheath 450 is likely to be pulled out of the palatine canal along with proximal portion 492.

Alternatively or additionally, for some applications, optical fiber 420 is coupled to tool 700 and is not in contact with implant 320, and is advanced distally in the greater palatine canal while coupled to tool 700. Applications in which optical fiber 420 is coupled to tool 700 and is advanced distally in the greater palatine canal in the absence of implant 320 are described hereinbelow with reference to FIG. 21.

FIGS. 15A and 15B show proximal, distal and middle portions of implant 320, in accordance with some applications of the present invention. Typically proximal portion 352 is more rigid than middle portion 351. Additionally, distal portion 354 is more rigid than middle portion 351 (middle portion 351 typically includes connecting element 328 described hereinabove with reference to FIG. 10).

Reference is again made to FIGS. 14A-B. Tool 700 is typically removably coupled to implant 320 and is configured to deliver the implant to the SPG through the greater palatine canal. Following deployment of implant 320 in the vicinity of the SPG, tool 700 detaches from implant 320. For some applications, tool 700 comprises a detachment mechanism configured to detach the delivery tool from implant 320 (e.g., a spring-based release mechanism, as is generally known in the art). For some applications, the cutting tool cuts fiber 420 without detaching implant 320 from tool 700, and typically after implant 320 has been detached from tool 700. For some applications, the detachment mechanism comprises a cutting tool, configured to detach tool 700 from the implant by cutting optical fiber 420.

For some applications, in which optical fiber 420 is not fixed to implant 320, optical fiber 420 is decoupled from the neural stimulator implant by pulling a proximal end of the optical fiber. Typically, while pulling optical fiber 420, implant 320 is maintained in place by tool 700 (or by additional mechanical elements). For example, a pusher may be used to maintain implant 320 in the vicinity of the SPG, while optical fiber 420 is being pulled and decoupled from implant 320. As shown for example in FIG. 15, optical fiber 420 wraps around the distal end of implant 320, such that by pulling optical fiber 420 while holding implant 320 in place, optical fiber 420 is entirely removed from contact with the implant.

It is noted that the scope of the present invention includes using optical fiber 420, even without an implant, to assess a shape of a bony canal (not necessarily the greater palatine canal), by assessing a shape of the optical fiber during advancement through the bony canal.

Figures 18A, 18B, 18C:
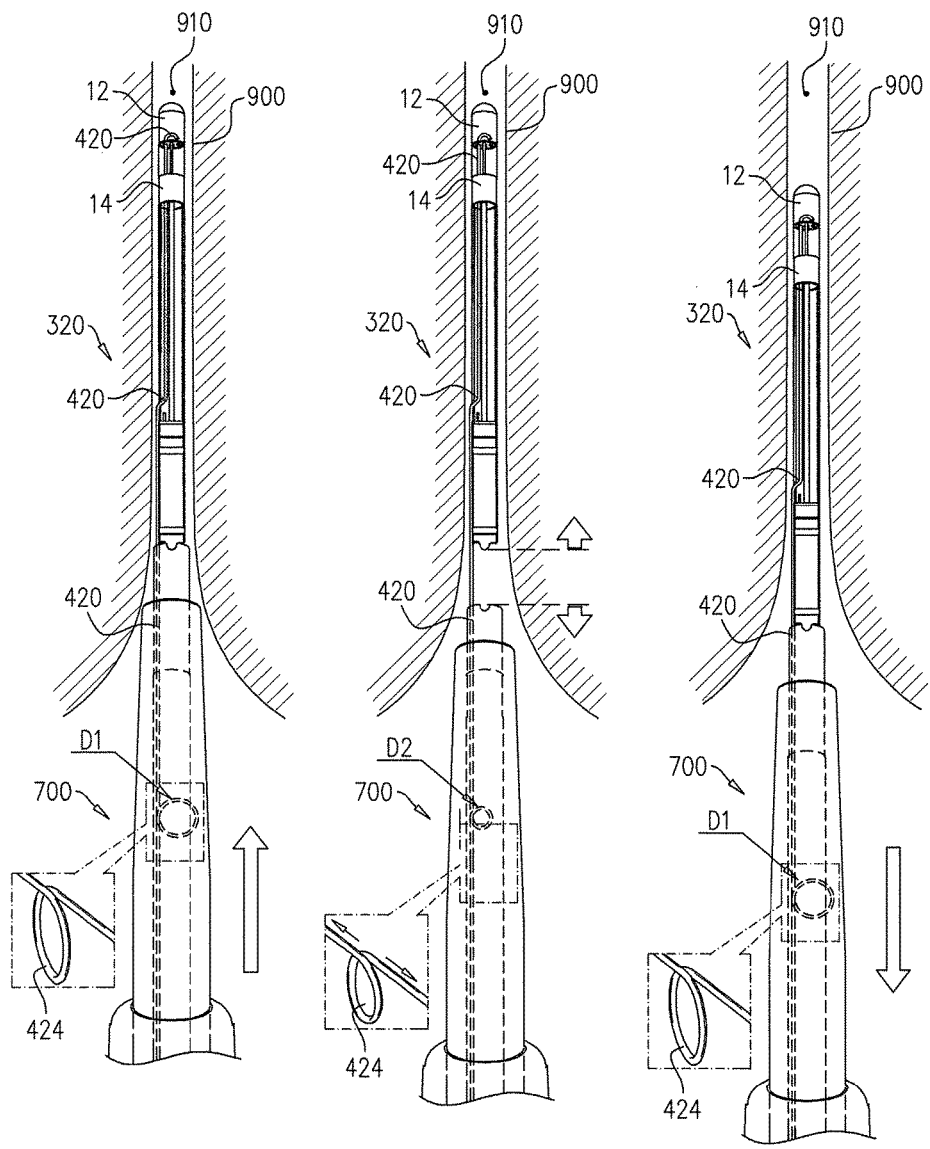
FIGS. 18A, 18B and 18C are schematic illustrations of apparatus comprising neural simulator, optical fiber and tool in accordance with some applications of the present invention.

Reference is now made to FIGS. 18A-C, which are schematic illustrations of apparatus 200 comprising neural simulator implant 320, optical fiber 420 (removably coupled or fixed to implant 320) and tool 700 in accordance with some applications of the present invention. As shown in FIGS. 18A-C, optical fiber 420 is used to assess proper detachment of implant 320 from tool 700. Typically, once delivery tool 700 reaches the implantation site (i.e., the vicinity of the SPG), implant 320 is deployed at the implantation site by detaching from tool 700. Tool 700 is subsequently pulled back through the greater palatine canal and removed from the body of the subject. In cases in which detachment of implant 320 from tool 700 is not complete, implant 320 may be (undesirably) pulled back proximally in the canal together with tool 700, instead of properly remaining at the implantation site. Thus, for some applications, optical fiber 420 is used to assess proper detachment of implant 320 from tool 700 by monitoring a change in a shape of fiber 420. For such applications, a portion of optical fiber 420 is disposed in tool 700 and is shaped within tool 700 such that relative motion between implant 320 and delivery tool 700 (e.g., distancing of tool 700 from implant 320) causes a change in the shape of the portion of the optical fiber in tool 700.

As shown in FIGS. 18A-C, for some applications, the portion of optical fiber 420 in tool 700 is shaped to define a loop 424, such that distancing of the delivery tool from the implant causes a reduction in a diameter of the loop. FIG. 18A shows implant 320 coupled to optical fiber 420 and mounted onto tool 700 while being distally advanced in canal 900. A portion of fiber 420 is additionally disposed in tool 700 and is shaped to define a loop 424 during distal advancement of tool 700. When proper detachment of implant 320 from tool 700 is achieved at implantation site 910, tool 700 is distanced from implant 320 by slightly pulling tool 700 back in the canal. Distancing of the tool from the implant naturally causes a reduction in a diameter of loop 424, e.g., from D1 to D2 (FIG. 18B), since fiber 420 is held on either end by tool 700 and implant 320 while they are separating. The reduction in the diameter of loop 424 typically indicates proper decoupling of tool 700 from implant 320. Once proper decoupling is indicated, fiber 420 is cut at the distal portion of tool 700, and tool 700 is removed from the body of the subject. When proper decoupling of tool 700 and implant 320 is not achieved (FIG. 18C), this is indicated by tool 700 being pulled proximally in the canal together with implant 320, and a diameter of loop 424 remaining generally unchanged, indicating insufficient detachment of implant 320 from tool 700.

It is noted that loop 424 is shown by way of illustration and not limitation. The scope of the present invention includes additional or alternative non-straight shapes of the portion of fiber 420 that is disposed in tool 700. For example, the portion of optical fiber 420 in delivery tool 700 may be shaped to define a curve, such that distancing of delivery tool 700 from implant 320 causes a straightening of the curve.

Additionally or alternatively, apparatus 200 further comprises a proximity sensor configured to indicate that tool 700 is detached from implant 320 by generating a signal that varies in response to relative motion (e.g., distancing) between delivery tool 700 and implant 320.

For some applications, the proximity sensor comprises at least one radiofrequency (RF) coil coupled to implant 320, and at least one RF coil coupled to delivery tool 700. For example, the RF coil coupled to tool 700 may transmit energy to the RF coil which is coupled to implant 320. Typically, the RF receiving coil which is coupled to the implant has a load modulation circuit which imposes changes in the transmission signal, which are detected by the transmitting coil coupled to tool 700. Thus, the RF coil coupled to tool 700, e.g., at a distal end of tool 700, receives a baseline level of feedback from the RF coil coupled to implant 320 when implant 320 is mounted onto tool 700. A difference in the feedback from the RF coil coupled to the implant and received by tool 700 typically indicates proper separation of implant 320 from tool 700. On the other hand, pulling back of tool 700 without a change (or without a sufficient change) in the feedback typically indicates insufficient detachment between implant 320 and tool 700.

For some applications, the proximity sensor comprises at least one magnetic element coupled to implant 320 and at least one magnetic element coupled to the delivery tool 700. A sufficient change in the magnetic force between the two elements indicates sufficient detachment.

It is noted that the proximity sensor can be used in combination with, or in the absence of, optical fiber 420. The proximity sensor is used to indicate that delivery tool 700 is detached from the implant by generating a signal in response to relative motion (e.g., distancing) between delivery tool 700 and implant 320. For such applications, and in general, implant 320 typically has a maximum length of 4 cm and/or a maximum diameter of 3 mm.

Figure 19:
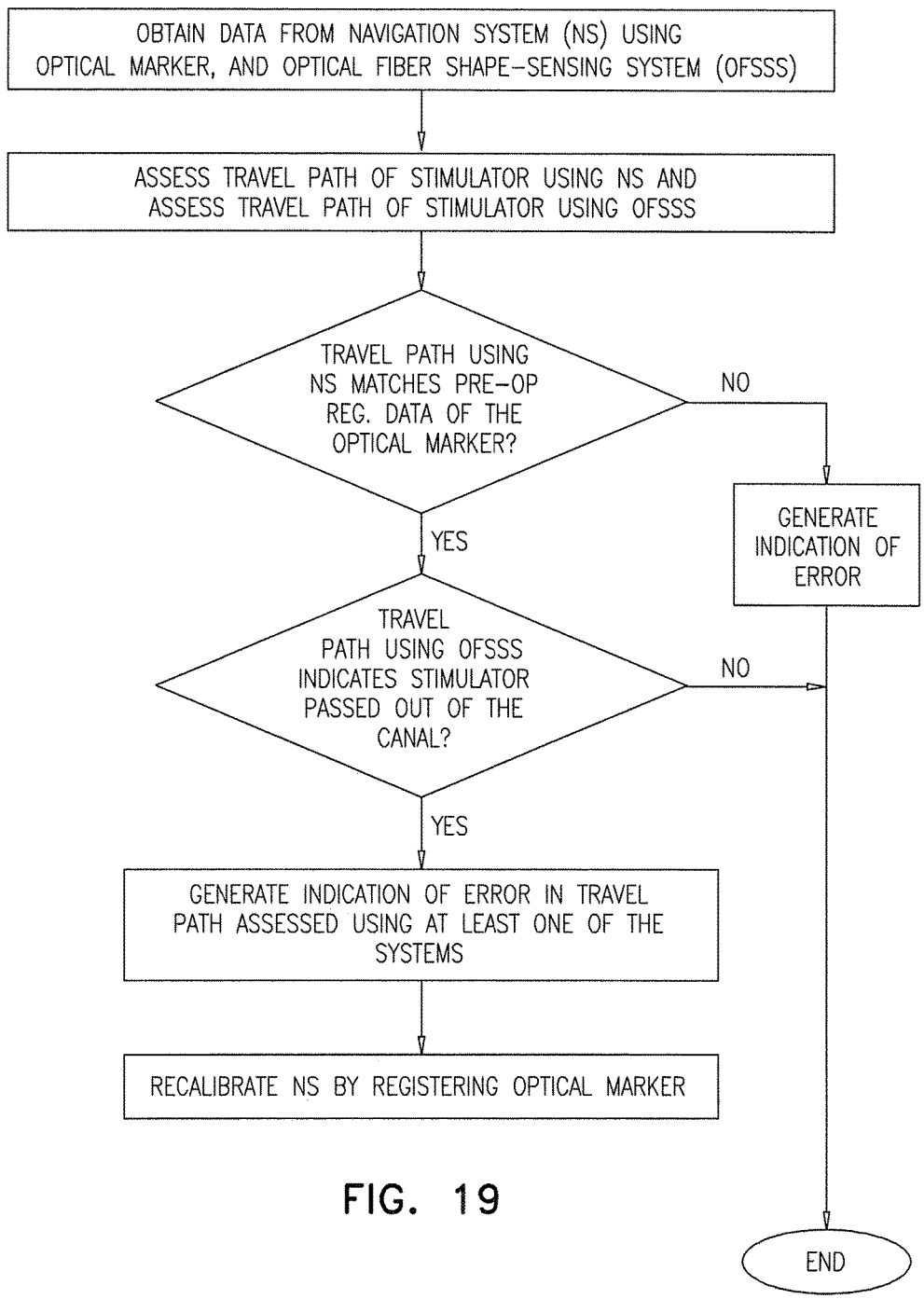
FIG. 19 is a flow chart showing a method for use in accordance with some applications of the present invention.
Figure 20:
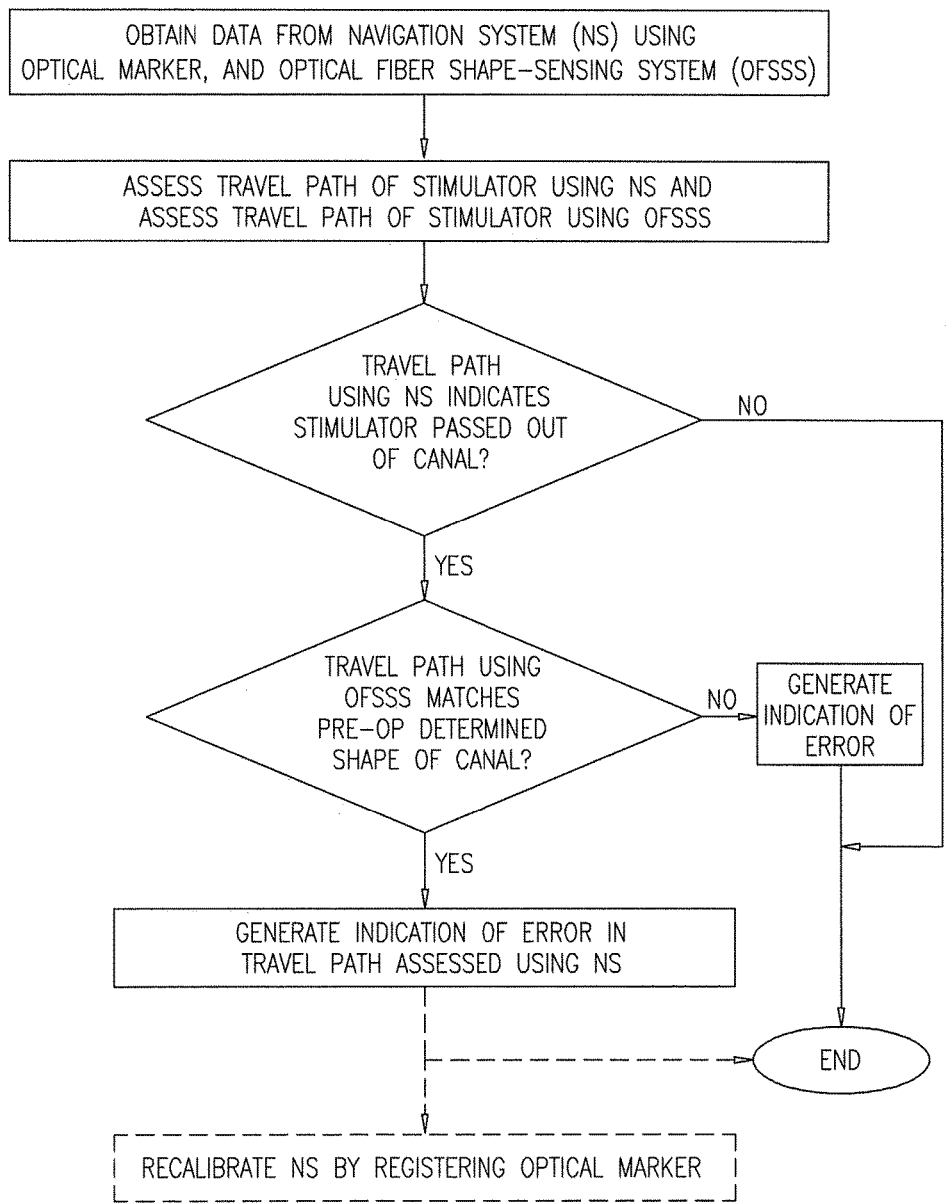
FIG. 20 is a flow chart showing a method for use in accordance with some applications of the present invention.

Reference is made to FIGS. 19 and 20, which are flow charts of steps for a method provided, in accordance with some applications of the present invention. For some applications, a travel path of implant 320 through the greater palatine canal is assessed by navigation system (NS), e.g., using optical markers 500, 510 and 520 on tool 700. Additionally, a travel path of implant 320 is assessed by the optical fiber shape sensing system (OFSSS) based on shape changes of the optical fiber during advancement to the SPG, as described herein. Typically it is possible to indicate whether there is an error in the travel path assessed using the navigation system if (a) the travel path detected using the optical fiber shape-sensing system matches a pre-operatively determined shape of the canal, typically obtained by CT-scan, and (b) the travel path assessed using the navigation system indicates that the neural stimulator has passed out of the canal. FIG. 20 is a flow chart showing the above described steps for indicating whether there is an error in the travel path assessed using the navigation system (NS), in accordance with some applications of the present invention.

Alternatively or additionally, the scope of the present invention includes indicating whether there is an error in the travel path assessed using at least one of the systems (i.e., NS and OFSSS) if (a) the travel path assessed using the navigation system matches pre-operative registration data of the optical marker, and (b) the travel path detected using the optical fiber shape-sensing system indicates that the neural stimulator has passed out of the canal. In cases in which an error is indicated, the navigation system is typically recalibrated by performing registration of the optical markers. FIG. 19 is a flow chart showing steps for indicating whether there is an error in the travel path assessed using at least one of the systems (i.e., NS and OFSSS).

Figure 21:
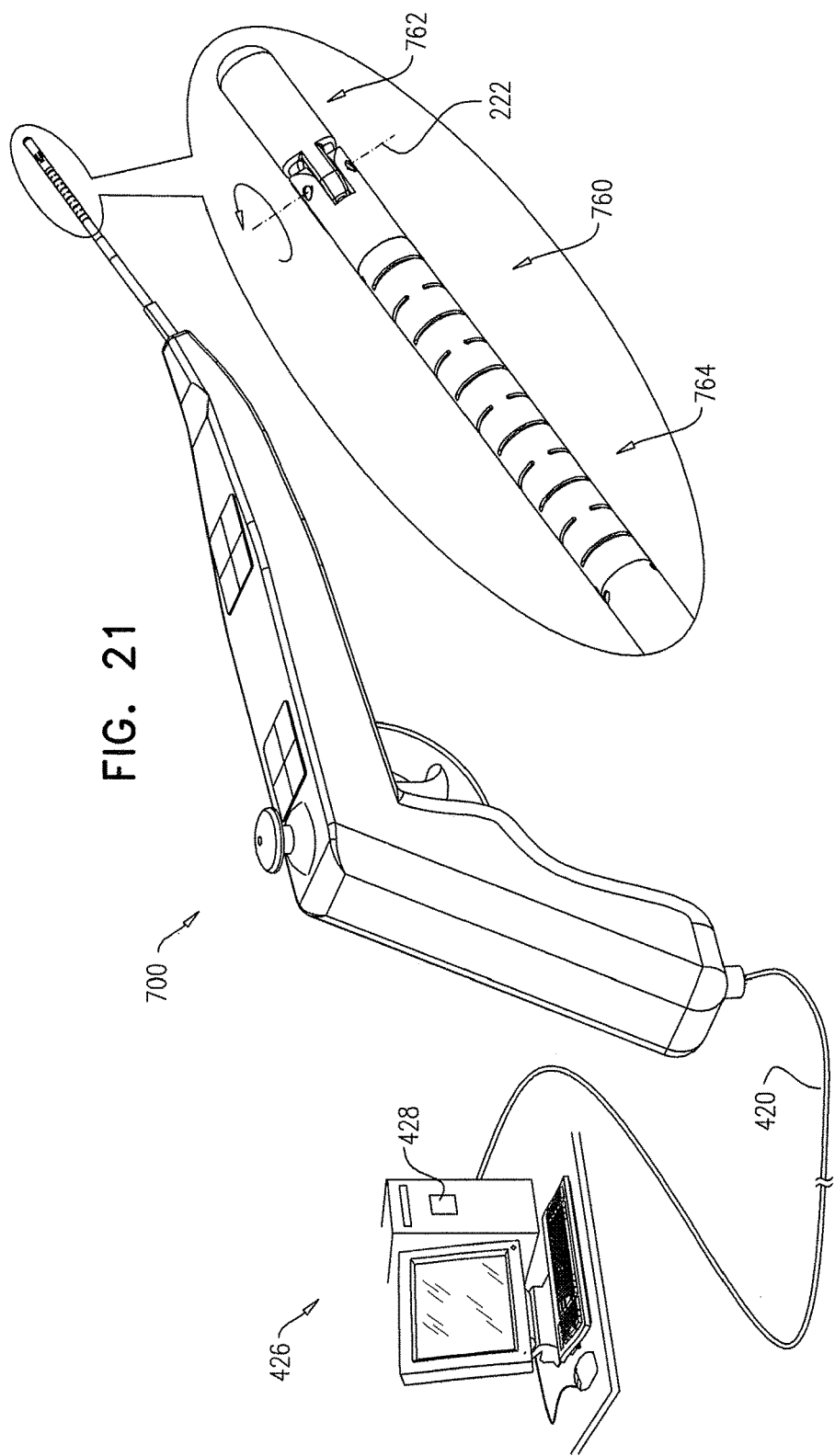
FIG. 21 is a schematic illustration of apparatus comprising an optical fiber and a delivery tool in accordance with some applications of the present invention.

Reference is now made to FIG. 21. For some applications, optical fiber 420 is distally advanced in the palatine canal without neural stimulator implant 320. For some such applications, delivery tool 700 comprises a steerable delivery device 760, e.g., a steerable trocar. As shown in FIG. 21, steerable delivery device 760 comprises axis 222 at a hinge of steerable delivery device 760, allowing steering of distal portion 762 of device 760. Portion 764 of steerable delivery device 760 is typically flexible, facilitating advancement through the palatine canal based on the steering of distal portion 762. Optical fiber 420 is typically distally advanced through the palatine canal using steerable delivery device 760 of tool 700.

A shape of the canal is assessed, e.g., mapped, using optical fiber shape-sensing system 426, based on a shape of optical fiber 420 during advancement through the palatine canal. Typically, steerable delivery device 760 is navigated in the palatine canal based on the assessing of the shape of the palatine canal. Accordingly, use of optical fiber 420 typically facilitates safe steering of delivery device 760 in the palatine canal, avoiding injuring to the palatine canal. Steerable delivery device 760 may be steered by deflection of a distal end of steerable delivery device 760.

Optical fiber 420 is then removed from the palatine canal and subsequently to removal of fiber 420, neural stimulator implant 320 is distally advanced using delivery tool 700, with or without delivery device 760, or using another delivery tool, through the palatine canal, and is implanted at a vicinity of the sphenopalatine ganglion (SPG) to apply electrical stimulation thereto. Typically, neural stimulator implant 320 is navigated through the palatine canal based on assessing of the shape of the palatine canal with optical fiber 420.

As described hereinabove, for some applications, a proximity sensor is configured to indicate that delivery tool 700 is detached from implant 320 by generating a signal that varies in response to relative motion (e.g., distancing) between delivery tool 700 and implant 320.

For some applications, prior to advancement of neural stimulator implant 320, delivery device 760 is advanced in the palatine canal together with fiber 420 and is used to prepare the palatine canal for subsequent advancement of neural stimulator implant 320, e.g., by widening the palatine canal. It is noted that preparation of the palatine canal with delivery device 760 and fiber 420 in the absence of neural stimulator implant 320 avoids forces of tissue clearance during preparation of the canal from being applied to neural stimulator implant 320. It is noted however, that for other applications as described for example in FIGS. 15A-B, neural stimulator implant 320 is advanced with fiber 420 and the delivery tool.

For some applications, for example, when a shape of the palatine canal is assessed by optical fiber 420 and/or by pre-operative CT as having many curves that would make advancing of neural stimulator implant 320 therethrough difficult, neural stimulator implant 320 may be advanced out of the palatine canal through a naturally-occurring or a surgically-made hole in the canal. In such cases, neural stimulator implant 320 is advanced out of the palatine canal, and for example, parallel to the canal, through the maxillary sinus which is located lateral to the palatine canal, toward the sphenopalatine ganglion (SPG).

Reference is again made to FIGS. 14-21. It is noted that shape sensing of the palatine canal with fiber 420 as described herein is performed on a sensing length of 4-6 cm (e.g., 5 cm) of fiber 420, which is the approximate length of the palatine canal. Thus, for example, the fiber Bragg gratings for use for these applications are typically positioned 2-5 mm apart.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with an optical fiber shape-sensing system, the apparatus comprising:
   an optical fiber, optically couplable to the optical fiber shape-sensing system, and configured to change shape during advancement through a greater palatine canal of a subject;
   a delivery tool configured to be removably coupled to the optical fiber and to distally advance the optical fiber through the greater palatine canal; and
   a neural stimulator implant, which is (a) shaped and sized to be delivered to a sphenopalatine ganglion (SPG) of the subject by the delivery tool, (b) configured to not be in contact with the optical fiber during delivery of the neural stimulator implant by the delivery tool, and (c) configured to apply electrical stimulation to the SPG.

2. The apparatus according to claim 1, wherein the neural stimulator implant is not disposed within the delivery tool.

3. The apparatus according to claim 1, wherein the optical fiber has a sensing length of 4-6 cm.

4. The apparatus according to claim 3, wherein the optical fiber has fiber Bragg gratings that are positioned 2-5 mm apart from each other.

5. The apparatus according to claim 1, wherein the optical fiber shape-sensing system includes optical fiber shape-sensing circuitry and wherein the optical fiber is optically couplable to the optical fiber shape-sensing circuitry.

6. The apparatus according to claim 1, wherein the neural stimulator has a proximal portion, a distal portion and a middle portion between the proximal and distal portions, and wherein the proximal portion is more rigid than the middle portion.

7. The apparatus according to claim 6, wherein the distal portion is more rigid than the middle portion.

8. The apparatus according to claim 1, wherein the optical fiber has fiber Bragg gratings.

9. A method comprising:
using a delivery tool, distally advancing, through a greater palatine canal of a subject, an optical fiber being configured to change shape during advancement through the greater palatine canal;
assessing a shape of the palatine canal using an optical fiber shape-sensing system, based on a shape of the optical fiber during advancement;
removing the optical fiber from the greater palatine canal; and
subsequently to removing the optical fiber, distally advancing through the greater palatine canal a neural stimulator that is configured to apply electrical stimulation to a sphenopalatine ganglion (SPG) of the subject.

10. The method according to claim 9, wherein distally advancing the neural stimulator comprises navigating the neural stimulator in the palatine canal based on the assessing of the shape of the palatine canal.

11. The method according to claim 9, wherein using the delivery tool comprises navigating the delivery tool in the palatine canal based on the assessing of the shape of the palatine canal.

12. The method according to claim 9, wherein assessing the shape of the palatine canal using the optical fiber shape-sensing system, comprises mapping the palatine canal based on a shape of the optical fiber during advancement.

13. The method according to claim 9, further comprising implanting the neural stimulator in a vicinity of the SPG.

14. The method according to claim 9, wherein the optical fiber shape-sensing system includes optical fiber shape-sensing circuitry and wherein assessing comprises assessing a shape of the palatine canal using the optical fiber shape-sensing circuitry.

15. The method according to claim 9, further comprising, using the delivery tool during the distal advancing thereof, widening the palatine canal in preparation for advancing of the neural stimulator.

16. Apparatus comprising:
an optical fiber shape-sensing system;
an optical fiber, optically couplable to the optical fiber shape-sensing system, and configured to change shape during advancement through a greater palatine canal of a subject;
a delivery tool configured to be removably coupled to the optical fiber and to distally advance the optical fiber through the greater palatine canal; and
a neural stimulator implant, which is (a) shaped and sized to be delivered to a sphenopalatine ganglion (SPG) of the subject by the delivery tool, (b) configured to not be in contact with the optical fiber during delivery of the neural stimulator implant by the delivery tool, and (c) configured to apply electrical stimulation to the SPG.

17. The apparatus according to claim 16, wherein the optical fiber has a sensing length of 4-6 cm.

18. The apparatus according to claim 17, wherein the optical fiber has fiber Bragg gratings that are positioned 2-5 mm apart from each other.

19. The apparatus according to claim 16, wherein the optical fiber shape-sensing system comprises optical fiber shape-sensing circuitry and wherein the optical fiber is optically couplable to the optical fiber shape-sensing circuitry.

20. The apparatus according to claim 16, wherein the neural stimulator has a proximal portion, a distal portion and a middle portion between the proximal and distal portions, and wherein the proximal portion is more rigid than the middle portion.

* * * * *